United States Patent
Greene et al.

(10) Patent No.: US 11,860,164 B2
(45) Date of Patent: Jan. 2, 2024

(54) MARKERS, METHODS AND SYSTEMS FOR IDENTIFYING CELL POPULATIONS, DIAGNOSING, MONITORING, PREDICTING AND TREATING CONDITIONS

(71) Applicant: FRED HUTCHINSON CANCER CENTER, Seattle, WA (US)

(72) Inventors: Evan Greene, Seattle, WA (US); Greg Finak, Lake Forest Park, WA (US); Raphael Gottardo, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 633 days.

(21) Appl. No.: 16/899,476

(22) Filed: Jun. 11, 2020

(65) Prior Publication Data

US 2020/0393465 A1 Dec. 17, 2020

Related U.S. Application Data

(60) Provisional application No. 62/860,649, filed on Jun. 12, 2019.

(51) Int. Cl.
*G16B 5/00* (2019.01)
*G16B 25/10* (2019.01)
*G01N 33/574* (2006.01)

(52) U.S. Cl.
CPC .......... *G01N 33/5743* (2013.01); *G16B 5/00* (2019.02); *G16B 25/10* (2019.02)

(58) Field of Classification Search
None
See application file for complete search history.

(56) References Cited

PUBLICATIONS

Greene et al (Patterns, 2021, 2:100372).*

* cited by examiner

*Primary Examiner* — Laura B Goddard
(74) *Attorney, Agent, or Firm* — Schwabe, Williamson & Wyatt P.C.

(57) ABSTRACT

Disclosed herein are to markers, methods and systems for identifying cell populations, diagnosing, monitoring and treating cancer, including biomarkers predictive of response to immunotherapy treatment in Merkel cell carcinoma.

9 Claims, 42 Drawing Sheets

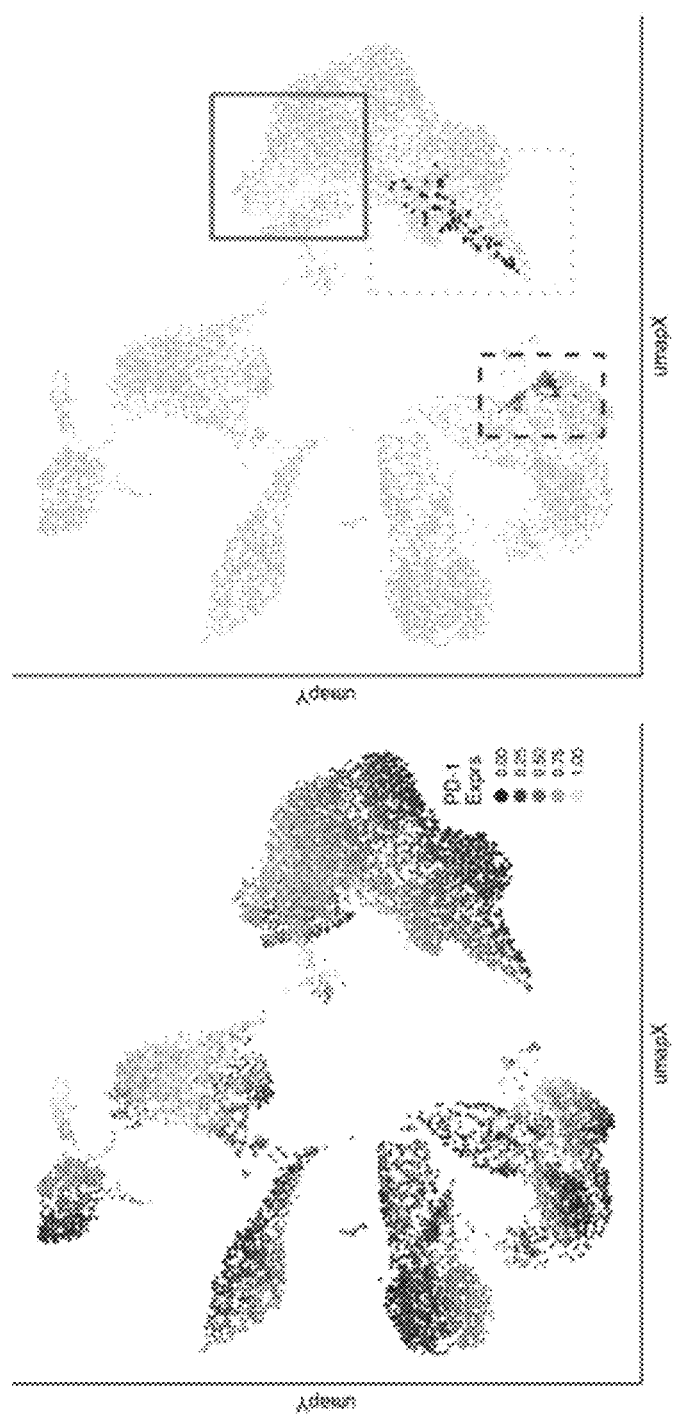

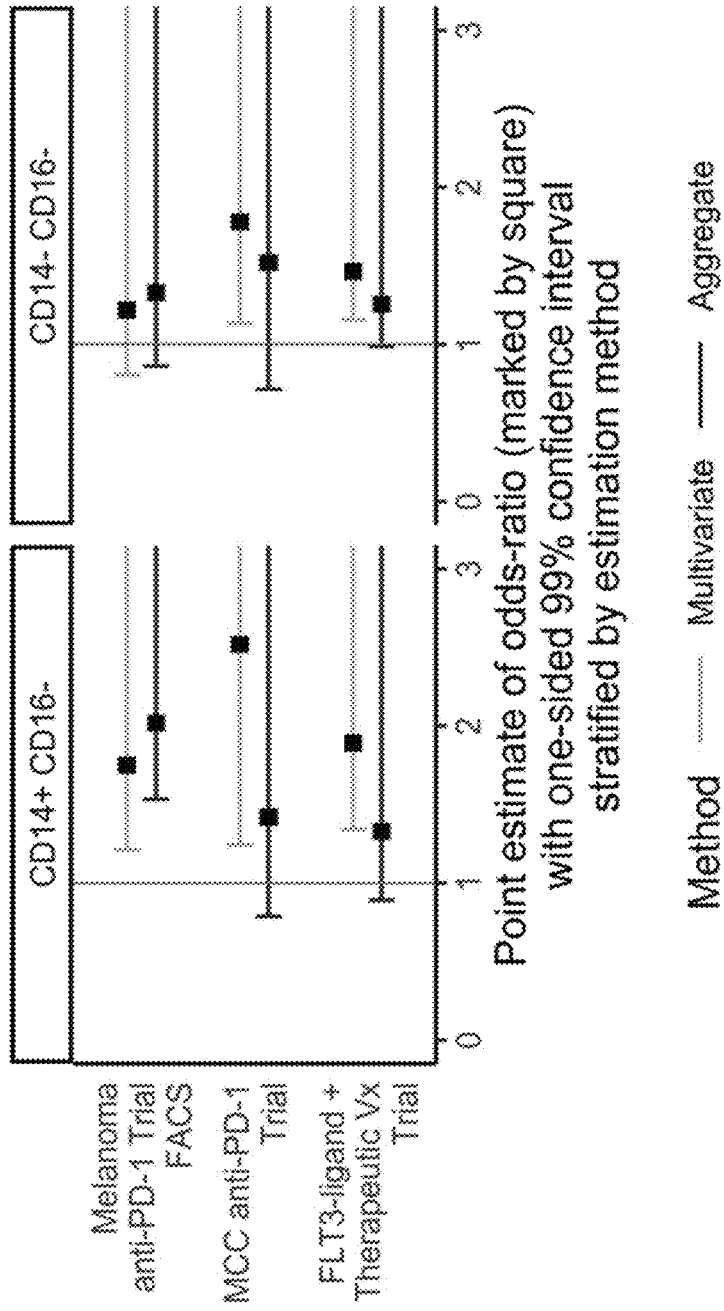

Fig. 12A
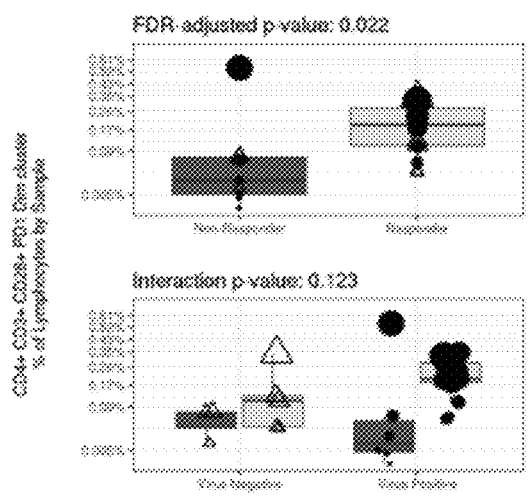
Fig. 12B
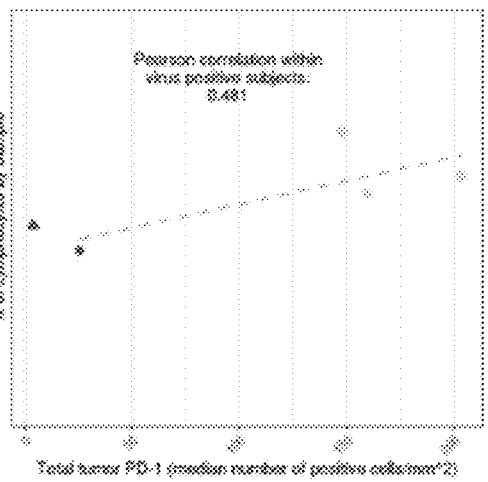
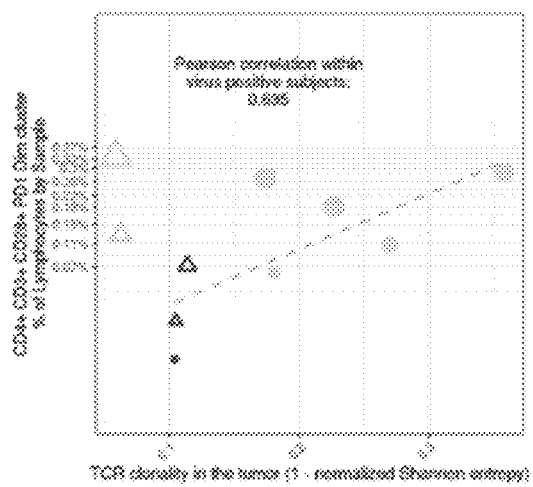
Fig. 12C

Fig. 13A
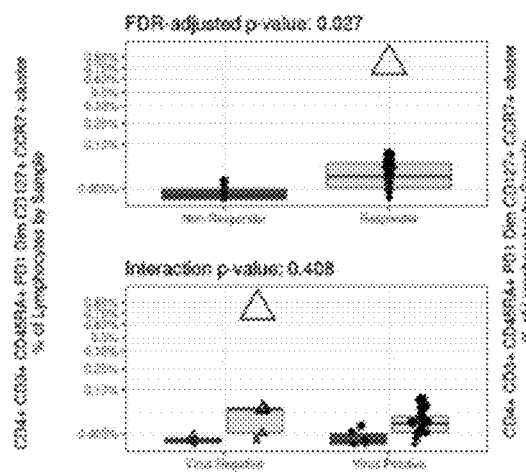
Fig. 13B
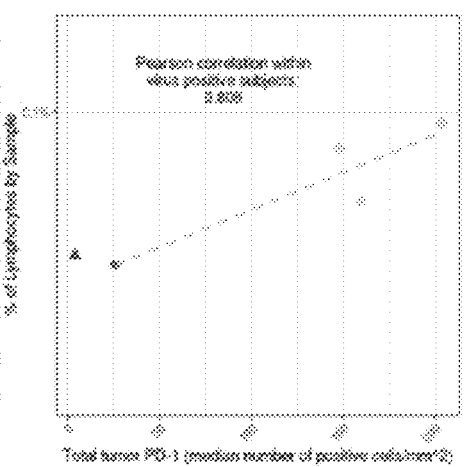
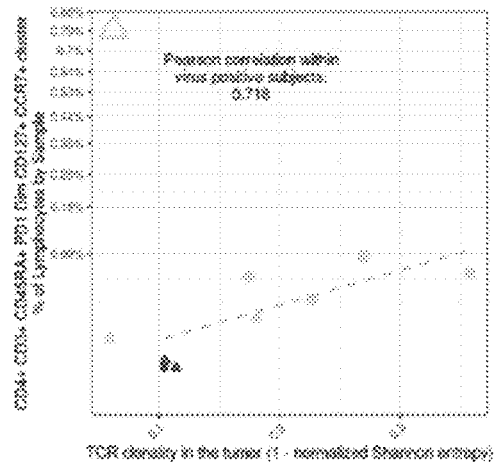
Fig. 13C

Fig. 15A Pre-Change

Fig. 15B Post-Change

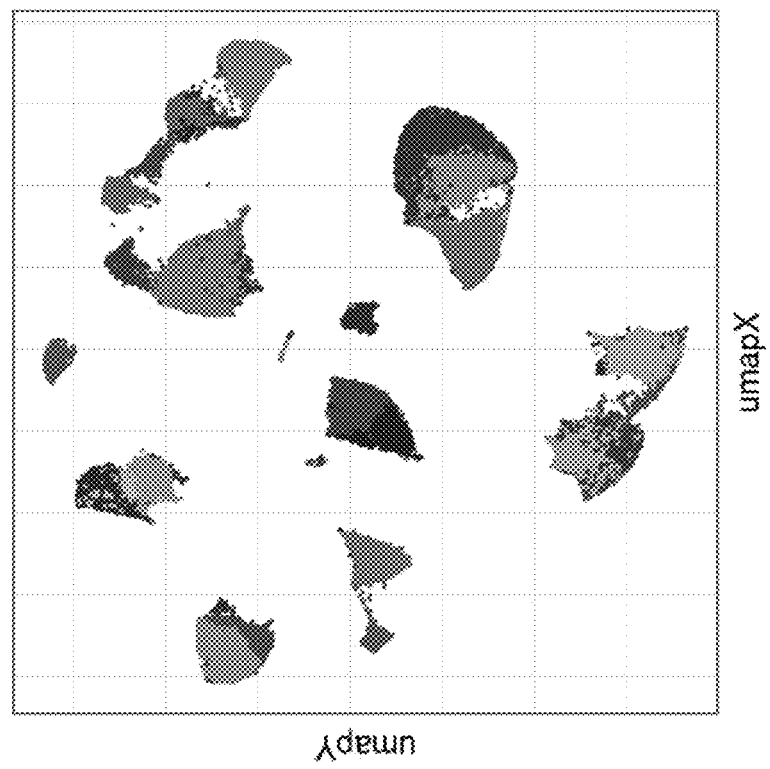
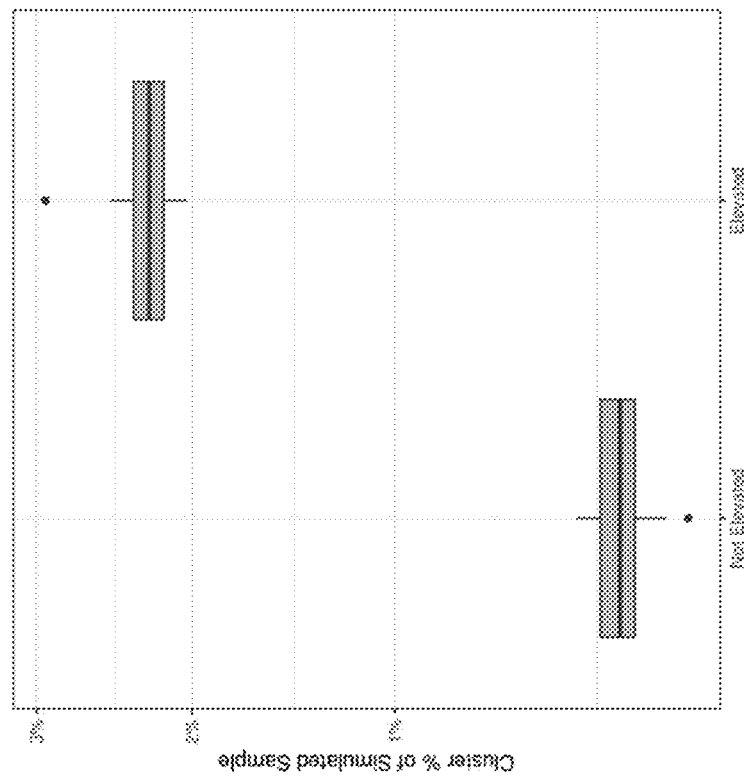
Fig. 23B
Fig. 23C

MARKERS, METHODS AND SYSTEMS FOR IDENTIFYING CELL POPULATIONS, DIAGNOSING, MONITORING, PREDICTING AND TREATING CONDITIONS

CROSS REFERENCE TO RELATED APPLICATION

This application claims the benefit of priority to U.S. Provisional No. 62/860,649, filed on Jun. 12, 2019, which is hereby incorporated by reference in its entirety.

ACKNOWLEDGMENT OF GOVERNMENT SUPPORT

This invention was made with government support under Grant Nos. EB008400 and GM118417 awarded by the National Institutes of Health. The government has certain rights in the invention.

FIELD

This disclosure relates to methods, markers and systems for identifying cell populations, diagnosing, monitoring and treating cancer, including biomarkers predictive of response to immunotherapy treatment in Merkel cell carcinoma subjects.

BACKGROUND

Cytometry is a standard technology used to measure the cellular composition of biological samples. Modern instruments can measure up to thirty (via fluorescence) or forty (via mass) protein markers per individual cell and increasing throughput can quantify millions of cells per sample. Clinical trials often use cytometry to profile the state of the immune system of each subject. A typical trial will measure many biological samples per subject, often in a longitudinal design. As a result, a single clinical trial generates many high-dimensional samples that together can produce measurements for hundreds of millions of cells. After measurements are collected, cell sub-populations of interest must be identified within each sample in order to analyze these data.

Identifying cell sub-populations is usually done via a manual process called "gating". An investigator gates a single sample by sequentially inspecting two-dimensional dot plots of protein expression and grouping cells with similar expression profiles together. Each sample is gated according to the same scheme, and the frequencies of cells found in each manually-identified cell sub-population are used to compare samples.

Manual gating is known to be biased in high-dimensional experiments and hard-to-reproduce (Finak et al., Standardizing flow cytometry immunophenotyping analysis from the human ImmunoPhenotyping consortium. Sci. Rep., 6:20686, February 2016). Manual gating only identifies cell populations targeted by the investigator. Hence manual identification cannot be used to perform unbiased discovery and analysis on high-dimensional cytometry data, since the number of potential populations measured in such datasets grows exponentially with the number of measured protein markers. This implies that modern platforms are already producing data sets whose information content has outpaced the ability to analyze the data, and as a result clinically relevant cell sub-populations potentially remain undiscovered.

A variety of computational methods have been developed over the last decade to identify cell populations in cytometry data have helped researchers interrogate the immune system clinical settings (Aghaeepour et al., Critical assessment of automated flow cytometry data analysis techniques. Nature methods, 10(3):228, 2013); (Lukas M Weber and Mark D Robinson. Comparison of clustering methods for high-dimensional single-cell flow and mass cytometry data. Cytometry Part A, 89(12):1084-1096, 2016). Despite these successes, methods for computational cell population identification still face significant challenges. Methods often require that analysts specify the number of clusters (i.e., cell sub-populations) in a sample (Aghaeepour et al., Rapid cell population identification in flow cytometry data. Cytometry Part A, 79(1):6-13, 2011), or that they know which clusters are of interest beforehand (Lux et al., Flowlearn: Fast and precise identification and quality checking of cell populations in flow cytometry. Bioinformatics, 1:9, 2018). Such information is generally not available in the discovery context. To over-come this lack of information, one analysis approach is to over-partition data into a very large number of clusters (though this still requires the ability to place an upper bound). However, when methods make strong assumptions about the distribution that generated the observed dataset, the structure captured by over-partitioning can reflect parametric assumptions rather than the underlying biology (Guenther Walther et al., Automatic clustering of flow cytometry data with density-based merging. Advances in bioinformatics, 2009). Another challenge for many methods is that biologically equivalent clusters are usually given different, uninformative labels when samples are analyzed independently. Because of this, methods must provide some mechanism to match clusters across samples. One solution is to define a metric on the space of protein measurements in an attempt to quantify cluster similarities across samples (Orlova et al., PloS one, 11(3):e0151859, 2016; Orlova et al., Scientific reports, 8(1):3291, 2018). However, choosing an appropriate metric to quantify similarity becomes increasingly difficult as the dimension of the dataset grows due to sparsity (Saeys et al., Science not art: statistically sound methods for identifying subsets in multi-dimensional flow and mass cytometry data sets". Nature Reviews Immunology, 18(1):78, 2018). Alternatively, investigators often combine experimental samples and then cluster the resulting dataset (Weber et al., Diffcyt: Differential discovery in high-dimensional cytometry via high-resolution clustering. Nature Communications Biology, 2019), (Hu et al., Metacyto: A tool for automated meta-analysis of mass and flow cytometry data. Cell Reports, 24(5):1377-1388, 2018). This solution can mask biological signal when batch effects or other non-biological sources of variation systematically affect the expression of one or more measured proteins. Methods using this approach can also fail to identify small but biologically relevant clusters since computational limitations cause many methods to recommend sub-sampling cells from each sample before combining the samples for analysis.

Accordingly, there exists the need for improved methods for identifying cell populations associated with certain conditions.

SUMMARY

Disclosed herein is a non-parametric method for automated unbiased cell population discovery in single-cell flow and mass cytometry that fully annotates cell populations with biologically interpretable phenotypes through a novel procedure called full annotation using shape-constrained trees (FAUST). FAUST was applied to data from four cancer immunotherapy trials, discovering cell populations associated with treatment outcome across trials. In a Merkel cell carcinoma anti-PD-1 trial, the method detected a programmed cell death receptor 1 (PD-1) expressing CD8+ T cell population in blood at baseline that predicted outcome and correlated with PD-1 IHC and T cell clonality in the tumor, while existing computational discovery approaches failed to identify any significant T cell correlates. Additionally, the method validated a cellular correlate in a melanoma trial, and independently detected it de-novo in two additional independent trials. FAUST's phenotypic annotations enable cross-study data integration and multivariate analysis in the presence of heterogeneous data and even diverse staining panels, demonstrating FAUST is a powerful new method for unbiased discovery in single-cell data.

As such, also disclosed herein are markers identified by FAUST which are associated with particular conditions. In one example, candidate biomarkers were found in baseline fresh blood samples from patients with Merkel cell carcinoma. For example, the phenotypes of T cell candidate biomarkers included one or more of the follow combinations:

1. CD4− CD3+ CD8+ CD45RA− HLADR+ CD28+ PD1 Dim CD25−CD127− CCR7−
2. CD4+ CD3+ CD8− CD45RA− HLADR− CD28+ PD1 Dim CD25−CD127− CCR7−
3. CD4+ CD3+ CD8− CD45RA+ HLADR− CD28− PD1 Dim CD25− CD127+ CCR7+
4. CD4− CD3+ CD8+ CD45RA− HLADR+ CD28+ PD1 Bright CD25− CD127− CCR7−
5. CD4+ CD3+ CD8− CD45RA− HLADR+ CD28+ PD1 Dim CD25− CD127− CCR7−
6. CD4+ CD3+ CD8− CD45RA+ HLADR− CD28+ PD1− CD25− CD127+ CCR7−
7. CD4− CD3+ CD8+ CD45RA− HLADR− CD28+ PD1 Dim CD25− CD127− CCR7−
8. CD4− CD3+ CD8+ CD45RA+ HLADR− CD28− PD1 Bright CD25− CD127− CCR7−
9. CD4+ CD3+ CD8− CD45RA+ HLADR− CD28+ PD1 Dim CD25− CD127+ CCR7−
10. CD4− CD3+ CD8+ CD45RA+ HLADR− CD28− PD1 Dim CD25− CD127− CCR7−
11. CD4− CD3+ CD8+ CD45RA+ HLADR− CD28− PD1 Dim CD25+CD127− CCR7−
12. CD4+ CD3+ CD8− CD45RA− HLADR− CD28+ PD1 Dim CD25− CD127− CCR7+
13. CD4+ CD3+ CD8− CD45RA− HLADR+ CD28+ PD1 Dim CD25− CD127− CCR7+
14. CD4− CD3+ CD8+ CD45RA− HLADR− CD28+ PD1 Bright CD25− CD127− CCR7−
15. CD4− CD3+ CD8− CD45RA+ HLADR+ CD28+ PD1 Dim CD25− CD127− CCR7−
16. CD4+ CD3+ CD8− CD45RA+ HLADR− CD28− PD1 Dim CD25− CD127− CCR7−
17. CD4+ CD3+ CD8− CD45RA+ HLADR− CD28+ PD1 Dim CD25− CD127− CCR7+. In the aforementioned listing, the phenotypes of T cell candidate biomarkers are listed in ranked order, from strongest association with immunotherapy treatment to weakest (but still statistically significant at FDR-adjusted 0.20 level).

Additionally, phenotypes of myeloid candidate biomarkers were discovered and annotated by the FAUST method, and were associated with patient response to immunotherapy. These candidate biomarkers were also found in baseline fresh blood samples from patients with Merkel cell carcinoma. For example, in some embodiments, one of more of the following combinations of candidate biomarkers were discovered to be associated with response to immunotherapy in Merkel cell carcinoma:

1. CD33 Bright CD16− CD15− HLADR Bright CD14+ CD3− CD11B+CD20− CD19− CD56− CD11C+
2. CD33 Bright CD16− CD15− HLADR Bright CD14− CD3− CD11B+CD20− CD19− CD56− CD11C+
3. CD33 Bright CD16− CD15+ HLADR Bright CD14+ CD3− CD11B+CD20− CD19− CD56− CD11C+
4. CD33 Bright CD16+ CD15+ HLADR Bright CD14+ CD3− CD11B+CD20− CD19− CD56− CD11C+
5. CD33 Bright CD16− CD15− HLADR Bright CD14− CD3− CD11B−CD20− CD19− CD56− CD11C+
6. CD33 Dim CD16+ CD15+ HLADR Bright CD14+ CD3− CD11B+CD20− CD19− CD56− CD11C+
7. CD33− CD16− CD15− HLADR Dim CD14+ CD3− CD11B+ CD20− CD19− CD56− CD11C+
8. CD33 Dim CD16− CD15+ HLADR Dim CD14− CD3− CD11B+CD20− CD19− CD56− CD11C−
9. CD33 Dim CD16+ CD15+ HLADR Bright CD14− CD3− CD11B+CD20+ CD19+ CD56− CD11C−
10. CD33 Bright CD16− CD15− HLADR Dim CD14+ CD3− CD11B+CD20− CD19− CD56− CD11C+
11. CD33 Dim CD16− CD15+ HLADR Bright CD14+ CD3− CD11B+CD20− CD19− CD56− CD11C+
12. CD33 Dim CD16+ CD15+ HLADR Dim CD14− CD3+ CD11B+CD20− CD19− CD56− CD11C−
13. CD33 Dim CD16− CD15− HLADR Bright CD14− CD3− CD11B+CD20− CD19− CD56− CD11C+
14. CD33 Dim CD16− CD15+ HLADR− CD14− CD3− CD11B+ CD20− CD19− CD56− CD11C−
15. CD33 Bright CD16− CD15− HLADR Dim CD14+ CD3− CD11B+CD20− CD19− CD56− CD11C−
16. CD33 Dim CD16− CD15+ HLADR− CD14− CD3− CD11B− CD20− CD19− CD56− CD11C−
17. CD33 Dim CD16− CD15− HLADR Dim CD14− CD3− CD11B− CD20− CD19− CD56− CD11C+
18. CD33− CD16− CD15− HLADR Bright CD14− CD3− CD11B+ CD20− CD19− CD56+ CD11C+
19. CD33 Dim CD16− CD15− HLADR Dim CD14− CD3− CD11B− CD20− CD19− CD56− CD11C−. In the aforementioned listing, the phenotypes are listed in ranked order, from strongest association with treatment to weakest (but still statistically significant at FDR-adjusted 0.20 level).

The disclosed markers can be used to diagnosis, monitor, and/or treat particular conditions and diseases, including predicting patient response to anti-PD-1 immunotherapy in Merkel cell carcinoma subjects. In some particular examples, the disclosed markers are used to diagnosis, monitor and/or treat Merkel cell carcinoma of viral origin. Assays and kits for measuring the disclosed biomarkers are also disclosed.

The foregoing and other features and advantages of the disclosure will become more apparent from the following detailed description, which proceeds with reference to the accompanying figures.

BRIEF DESCRIPTION OF DRAWINGS

FIGS. 2A-2C illustrate FAUST annotations reflect underlying protein expression not captured by dimensionality reduction. 2A) In a baseline responder's sample, the densities of per-marker fluorescence intensity for cells in the four correlates as well as the entire collection of live lymphocytes in the sample are compared. Cells used in density calculations are marked by tick marks and demonstrate that differences in cluster annotations reflect strict expression differences in the underlying data. 2B) A UMAP embedding computed from the same sample as FIG. 2A using the ten stated protein markers. All cells in the sample were used to compute the embedding. The embedding is colored by the relative intensity of observed PD-1 expression, windsorized at the 1st and 99th percentile, and scaled to the unit interval. A random subset of 10,000 cells is displayed from 233,736 cells in the sample together with the complete set of 61 CD8+ PD-1 dim cells, 176 CD8+ PD-1 bright cells, 450 CD45RA− CD4+ PD-1 dim cells, and 76 CD45RA+CD4+ PD-1 dim cells. 2C) The same UMAP embedding highlighting the location of the cells from the four discovered correlates. The correlates are annotated by FAUST as: CD4 bright CD3+ CD8− CD45RA− HLA-DR− CD28+ PD-1 dim CD25− CD127− CCR7−; CD4− CD3+ CD8+ CD45RA− HLA-DR+ CD28+ PD-1 bright CD25− CD127− CCR7−; CD4− CD3+ CD8+ CD45RA− HLA-DR+ CD28+ PD-1 dim CD25− CD127− CCR7−; CD4 bright CD3+ CD8− CD45RA+ HLA-DR− CCR7+.

FIGS. 6A and 6B show standardized annotation of clusters enables cross-study meta-analysis of data sets stained with disparate marker panels. Differential abundance between responders and non-responders across the different sub-compartments was tested by aggregating model coefficients (analogous to meta-analysis over cell sub-populations in a sub-compartment) from a multivariate GLMM and by univariate modeling of aggregated cell counts. One-sided, 99% (Bonferroni-adjusted) confidence intervals for increased abundance in responders vs. non-responders are displayed for each sub-compartment in each data set. In all modeling scenarios, when the whisker of a forest-plot line crosses the vertical red-line at 1, this indicates the increased odds in the responders vs non-responders are not statistically significant at the Bonferroni-adjusted level. 6A) Cells in the CD14+CD16− HLA-DR+ sub-compartment were found to be significantly more abundant in responders than non-responders in all data sets tested using the multivariate modeling approach. In the univariate modeling of aggregate cell counts, the CD14+ CD16− HLA–DR+ sub-compartment was only significant in the melanoma anti-PD-1 FACS data set, consistent with the authors' published findings. The x-axis can be interpreted as the odds increase in the probability of observing more cells in the responders than the non-responders in the compartment. 6B) Cells in the CD14− CD16− HLA-DR+ sub-compartment were found to be significantly more abundant in responders than non-responders in the two CITN data sets tested using the multivariate modeling approach. It is believed that the observed difference between the CITN trials and the melanoma anti-PD-1 trial is explained by cryopreservation in the latter trial.

FIGS. 12A-12C provide the FAUST sub-population annotated CD4 bright CD3+CD8− CD45RA− HLA-DR− CD28+ PD-1 dim CD25− CD127− CCR7− that is associated with clinical outcome at the FDR-adjusted 5% level, with tumor measurements in FIGS. 12B and 12C.

FIGS. 13A-13C provide the FAUST sub-population annotated CD4 bright CD3+CD8− CD45RA+ HLA-DR− CD28− PD-1 dim CD25− CD127+ CCR7+ that is associated with clinical outcome at the FDR-adjusted 5% level, with tumor measurements in FIGS. 13B and 13C.

FIG. 15A shows the initial manual gating strategy for the Lymphocytes of a sample. FIG. 15B shows the same sample with the modified gate.

FIG. 21A shows the best separated variable (V1), worst separated (V10), and their concatenation across 10 samples. FIG. 21B shows the elevated population across the entire 100 sample experiment.

FIG. 21C shows the umap generated from the 10 concatenated samples.

FIGS. 22A-22C provide a visual summary of simulation modified from baseline with 50 mixture components and a batch effect turned on. FIG. 22A shows the best separated variable (V1), worst separated (V10), and their concatenation across 10 samples. FIG. 22B shows the elevated population across the entire 100 sample experiment. FIG. 22C shows the umap generated from the 10 concatenated samples.

FIGS. 23A-23C provide a visual summary of simulation modified from baseline with 25 mixture components, batch effect turned on, nuisance variable turned on, and data transformed coordinate-wise by the map $g(x)=\Gamma(1+(x/4))$ after generation. FIG. 23A shows the best separated variable (V1), worst separated (V10), and their concatenation across 10 samples. FIG. 23B shows the elevated population across the entire 100 sample experiment. FIG. 23C shows the umap generated from the 10 concatenated samples.

FIG. 30A) Boxplots of the abundances of effector memory CD8 T cells co-expressing CD28, HLA-DR, and PD-1 in unstimulated baseline samples for subjects that were treated with pembrolizumab. FIG. 30B) Boxplots of the abundances of effector memory CD4 T cells co-expressing PD-1 and CD28. All FAUST phenotypes matched the phenotypes from the MCC trial, up to the number of annotation boundaries for each marker.

DETAILED DESCRIPTION OF SEVERAL EMBODIMENTS

Figures 1A, 1B:
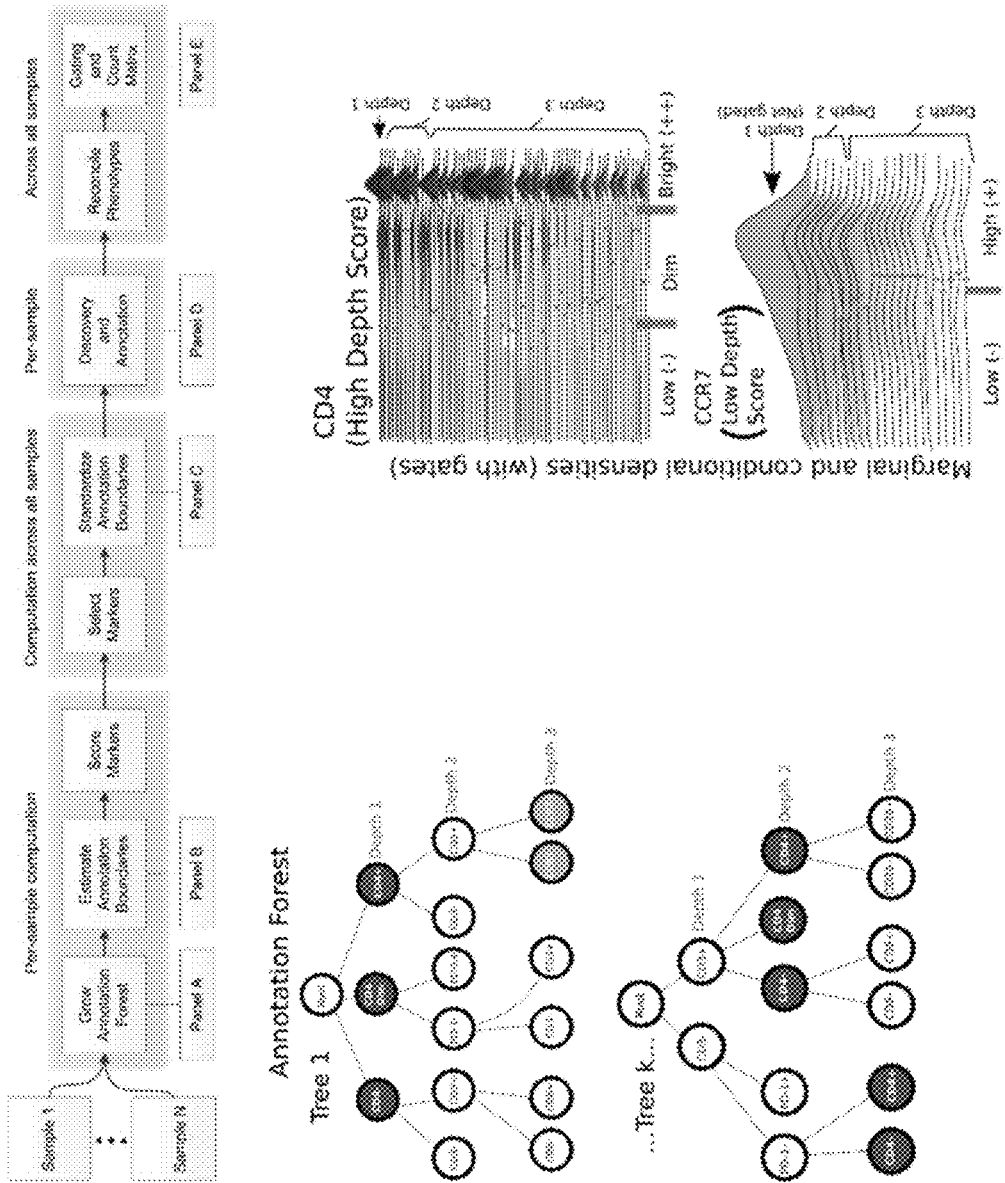
FIGS. 1A-1E is a schematic illustrating FAUST in accordance with an exemplary embodiment of the disclosure.
Figure 1C:
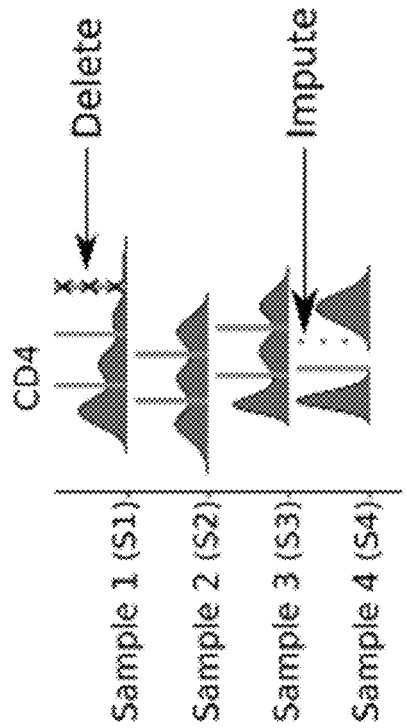
Figure 1D:
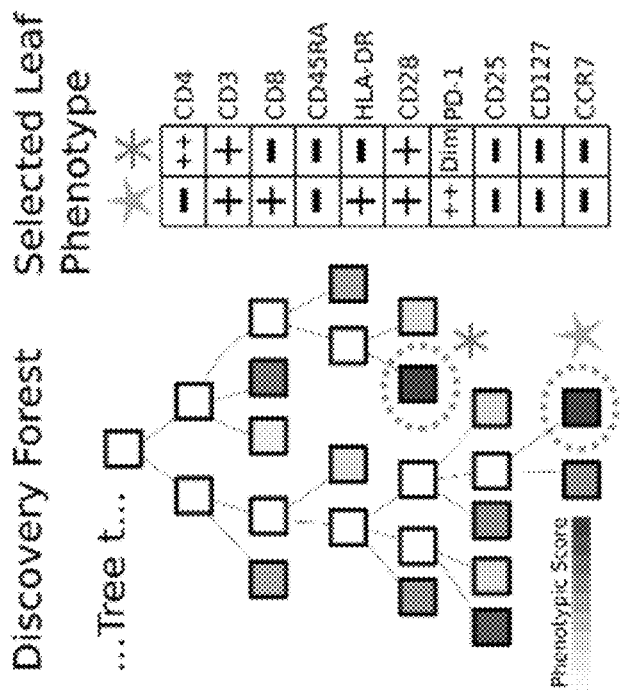
Figure 1E:
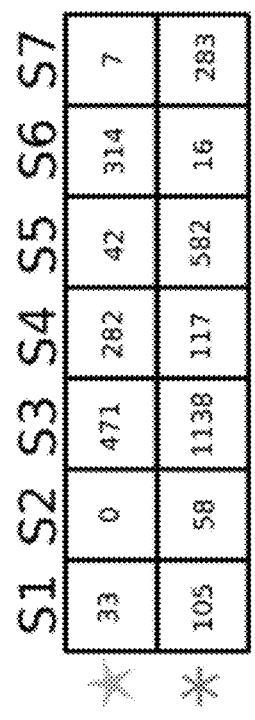

This technology disclosed herein is described in one or more exemplary embodiments in the following description with reference to the Figures. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Various operations may be described as multiple discrete operations in turn, in a manner that may be helpful in understanding embodiments; however, the order of description should not be construed to imply that these operations are order dependent.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B. It is further to be understood that all base sizes and all molecular weight or molecular mass values given for peptides and nucleic acids are approximate and are provided for description.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Although methods and materials similar or equivalent to those described herein can be used in the practice or testing of the present disclosure, suitable methods and materials are described below. All publications, patent applications, patents, and other references mentioned herein are incorporated by reference in their entirety. Unless otherwise defined, all technical terms used herein have the same meaning as commonly understood. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999. In addition, the materials, methods, and examples are illustrative only and not intended to be limiting.

Also, it is noted that embodiments may be described as a process depicted as a flowchart, a flow diagram, a dataflow diagram, a structure diagram, or a block diagram. Although a flowchart may describe the operations as a sequential process, many of the operations may be performed in parallel, concurrently, or simultaneously. In addition, the order of the operations may be re-arranged. A process may be terminated when its operations are completed, but may also have additional steps not included in the figure(s). A process may correspond to a method, a function, a procedure, a subroutine, a subprogram, and the like. When a process corresponds to a function, its termination may correspond to a return of the function to the calling function and/or the main function. Furthermore, a process may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

As used hereinafter, including the claims, the term "circuitry" may refer to, be part of, or include an Application Specific Integrated Circuit (ASIC), an electronic circuit, a processor (shared, dedicated, or group), and/or memory (shared, dedicated, or group) that execute one or more software or firmware programs, a combinational logic circuit, and/or other suitable hardware components that provide the described functionality. In some embodiments, the circuitry may implement, or functions associated with the circuitry may be implemented by, one or more software or firmware modules.

As used hereinafter, including the claims, the term "memory" may represent one or more hardware devices for storing data, including random access memory (RAM), magnetic RAM, core memory, read only memory (ROM), magnetic disk storage mediums, optical storage mediums, flash memory devices and/or other machine readable mediums for storing data. The term "computer-readable medium" may include, but is not limited to, memory, portable or fixed storage devices, optical storage devices, wireless channels, and various other mediums capable of storing, containing or carrying instruction(s) and/or data.

As used hereinafter, including the claims, the term "computing platform" may be considered synonymous to, and may hereafter be occasionally referred to, as a computer device, computing device, client device or client, mobile, mobile unit, mobile terminal, mobile station, mobile user, mobile equipment, user equipment (UE), user terminal, machine-type communication (MTC) device, machine-to-machine (M2M) device, M2M equipment (M2ME), Internet of Things (IoT) device, subscriber, user, receiver, etc., and may describe any physical hardware device capable of sequentially and automatically carrying out a sequence of arithmetic or logical operations, equipped to record/store data on a machine readable medium, and transmit and receive data from one or more other devices in a communications network. Furthermore, the term "computing platform" may include any type of electronic device, such as a cellular phone or smartphone, a tablet personal computer, a wearable computing device, an autonomous sensor, personal digital assistants (PDAs), a laptop computer, a desktop personal computer, a video game console, a digital media player, an in-vehicle infotainment (IVI) and/or an in-car entertainment (ICE) device, an in-vehicle computing system, a navigation system, an autonomous driving system, a vehicle-to-vehicle (V2V) communication system, a vehicle-to-everything (V2X) communication system, a handheld messaging device, a personal data assistant, an electronic book reader, an augmented reality device, and/or any other like electronic device.

As used hereinafter, including the claims, the term "link" or "communications link" may refer to any transmission medium, either tangible or intangible, which is used to communicate data or a data stream. Additionally, the term "link" may be synonymous with and/or equivalent to "communications channel," "data communications channel," "transmission channel," "data transmission channel," "access channel," "data access channel," "channel," "data link," "radio link," "carrier," "radiofrequency carrier," and/or any other like term denoting a pathway or medium through which data is communicated.

As used hereinafter, including the claims, the terms "module", "input interface", "converter", "analyzer", "artificial neural network", "trained neural network", "partially retrained artificial neural network", or "retrained artificial neural network" may refer to, be part of, or include one or more Application Specific Integrated Circuits (ASIC), electronic circuits, programmable combinational logic circuits (such as field programmable gate arrays (FPGA)) programmed with logic to perform operations described herein, a processor (shared, dedicated, or group) and/or memory (shared, dedicated, or group) that execute one or more software or firmware programs generated from a plurality of programming instructions with logic to perform operations described herein, and/or other suitable components that provide the described functionality In order to facilitate review of the various embodiments of this disclosure, the following explanations of specific terms are provided:

Administration: To provide or give a subject an agent by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Alteration or difference: An increase or decrease in the amount of something, such as a cell surface molecule expression. In some examples, the difference is relative to a control or reference value or range of values, such as an amount of a protein that is expected in a subject who does not have a particular condition or disease being evaluated. Detecting an alteration or differential expression/activity can include measuring a change in expression, concentration or activity, such as by ELISA, Western blot and/or mass spectrometry.

"Analysis" or "analyzing," as used herein, are used interchangeably and refer to any of the various methods of separating, detecting, isolating, purifying, solubilizing, detecting and/or characterizing molecules of interest. Examples include, but are not limited to, solid phase extraction, solid phase micro extraction, electrophoresis, mass spectrometry, e.g., Multiplexed targeted selected ion monitoring (SIM)-MS followed by iterative MS2 DDA, ESI-MS, SPE HILIC, or MALDI-MS, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

Antibody: An immunoglobulin, antigen-binding fragment, or derivative thereof, that specifically binds and recognizes an analyte (antigen). The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the VH and VL domains of one or more antibody(ies) linked by a suitable polypeptide linker as a genetically fused single chain molecule (see, for example, Bird et al, Science, 242:423-426, 1988; Huston et al, Proc. Natl. Acad. Sci., 85:5879-5883, 1988; Ahmad et al, Clin. Dev. Immunol, 2012, doi: 10.1 155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the VH and VL have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et ai, Proc. Natl. Acad. ScL, 90:6444-6448, 1993; Poljak of ai, Structure, 2: 1121-1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ed., W.H. Freeman and Co., page 91 (2007).) In several embodiments, the VH and VL combine to specifically bind the antigen. In additional embodiments, only the VH is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). Any of the disclosed antibodies can include a heterologous constant domain. For example the antibody can include constant domain that is different from a native constant domain, such as a constant domain including one or more modifications (such as the "LS" mutations) to increase half-life.

References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

The VH and VL contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Al-Lazikani et al, (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the VL of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples, monoclonal antibodies are isolated from a subject. Monoclonal antibodies can have conservative amino acid substitutions which have substantially no effect on antigen binding or other immunoglobulin functions. (See, for example, Harlow & Lane, Antibodies, A Laboratory Manual, $2^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas of aZ. Phage display: A Laboratory Manuel. $1^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. Methods of determining spatial conformation of epitopes include, for example, x-ray crystallography and multi-dimensional nuclear magnetic resonance spectroscopy. The term "antigen" denotes both subunit antigens, (for example, antigens which are separate and discrete from a whole organism with which the antigen is associated in nature), as well as killed, attenuated or inactivated bacteria, viruses, fungi, parasites or other microbes. An "antigen," when referring to a protein, includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens.

B-cell: One of the two major types of lymphocytes. B-cells arise from bone marrow progenitor cells, which progress through multiple stages such as the pro-, pre- and transitional stages into the naive B-cell. The antigen receptor on B lymphocytes is a cell-surface immunoglobulin molecule. Upon activation by an antigen, B-cells differentiate into cells producing antibody of the same specificity as their initial receptor.

An "immature B cell" is a cell that can develop into a mature B cell. Generally, pro-B cells (that express, for example, CD10) undergo immunoglobulin heavy chain rearrangement to become pro B pre B cells, and further undergo immunoglobulin light chain rearrangement to become an immature B cells. Immature B cells include T1 and T2 B cells. Thus, one example of an immature B cell is a T1 B that is an AA41$^{hi}$CD23$^{lo}$ cell. Another example of an immature B cell is a T2 B that is an AA41$^{hi}$CD23$^{hi}$ cell. Thus, immature B cells include B220 expressing cells wherein the light and the heavy chain immunoglobulin genes are rearranged, and that express AA41. Immature B cells can develop into mature B cells, which can produce immunoglobulins (e.g., IgA, IgG or IgM). Mature B cells express characteristic markers such as CD21 and CD23 (CD23$^{hi}$CD21$^{hi}$ cells), but do not express AA41. In some examples, a B cell is one that expresses CD179$^{hi}$, CD24, CD38 or a combination thereof. B cells can be activated by agents such as lippopolysaccharide (ITS) or IL-4 and antibodies to IgM.

B-cells have many functions. For example, a B-cell can serve as an antigen presenting cell (APC) (which activates T-cytotoxic cells toward effector function), activate naive or memory Th1 cells, or evolve into long-lived memory cell and transform into an antibody secreting plasma cell with T-cell help, and perpetuate antibody responses to autoantigens. Antigen is sensed by the B-cell via the B-cell receptor, or the immunoglobulin molecule.

Chromatography: A process of separating a mixture, for example a mixture containing peptides, proteins, polypeptides and/or antibodies. It involves passing a mixture through a stationary phase, which separates molecules of interest from other molecules in the mixture and allows one or more molecules of interest to be isolated.

Contacting: "Contacting" includes in solution and solid phase. "Contacting" can occur in vitro with, e.g., samples, such as biological samples containing a target biomolecule. "Contacting" can also occur in vivo.

Control: A reference standard. A control can be a known value or range of values indicative of basal levels or amounts or present in a tissue or a cell or populations thereof. A control can also be a cellular or tissue control, for example a tissue from a non-diseased state. A difference between a test sample and a control can be an increase or conversely a decrease. The difference can be a qualitative difference or a quantitative difference, for example a statistically significant difference.

Detecting: Identifying the presence, absence or relative or absolute amount of the object to be detected.

Diagnosis: The process of identifying a condition or disease by its signs, symptoms, results of various tests and presence of diagnostic indicators. The conclusion reached through that process is also called "a diagnosis."

Immunoassay: A biochemical test that measures the presence or concentration of a substance in a sample, such as a biological sample, using the reaction of an antibody to its cognate antigen, for example the specific binding of an antibody to a protein. Both the presence of antigen and the amount of antigen present can be measured. For measuring proteins, for each the antigen and the presence and amount (abundance) of the protein can be determined or measured. Measuring the quantity of antigen can be achieved by a variety of methods. One of the most common is to label either the antigen or antibody with a detectable label.

An "enzyme linked immunosorbent assay (ELISA)" is type of immunoassay used to test for antigens (for example, proteins present in a sample, such as a biological sample). A "competitive radioimmunoassay (RIA)" is another type of immunoassay used to test for antigens. A "lateral flow immunochromatographic (LFI)" assay is another type of immunoassay used to test for antigens.

Label: A detectable compound or composition that is conjugated directly or indirectly to another molecule, such as an antibody or a protein, to facilitate detection of that molecule. Specific, non-limiting examples of labels include fluorescent tags, enzymatic linkages (such as horseradish peroxidase), radioactive isotopes (for example $^{14}$C, $^{32}$P, $^{125}$I, $^{3}$H isotopes and the like) and particles such as colloidal gold. In some examples a protein, such as a protein associated with a particular infection, is labeled with a radioactive isotope, such as $^{14}$C, $^{32}$P, $^{125}$I, $^{3}$H isotope. In some examples an antibody that specifically binds the protein is labeled. Methods for labeling and guidance in the choice of labels appropriate for various purposes are discussed for example in Sambrook et al. (Molecular Cloning: A Laboratory Manual, Cold Spring Harbor, N. Y., 1989) and Ausubel et al. (In Current Protocols in Molecular Biology, John Wiley & Sons, New York, 1998), Harlow & Lane (Antibodies, A Laboratory Manual, Cold Spring Harbor Publications, New York, 1988).

Liquid chromatography: A process in which a chemical mixture carried by a liquid can be separated into components as a result of differential distribution of the chemical entities as they flow around or over a stationary liquid or solid phase. Non-limiting examples of liquid chromatography include reverse phase liquid chromatography, ion-exchange chromatography, size exclusion chromatography, affinity chromatography, and hydrophobic chromatography.

Mass spectrometer: A device capable of detecting specific molecular species and accurately measuring their masses. The term can be meant to include any molecular detector into which a polypeptide or peptide may be eluted for detection and/or characterization. A mass spectrometer consists of three major parts: the ion source, the mass analyzer, and the detector. The role of the ion source is to create gas phase ions. Analyte atoms, molecules, or clusters can be transferred into gas phase and ionized either concurrently (such as in electrospray ionization). The choice of ion source depends on the application.

Measure: To detect, quantify or qualify the amount (including molar amount), concentration or mass of a physical entity or chemical composition either in absolute terms in the case of quantifying, or in terms relative to a comparable physical entity or chemical composition.

Merkel Cell Carcinoma: A rare form of skin cancer that originates in Merkel cells. Merkel cells are found at the base of the epidermis. Some forms of Merkel cell carcinoma are caused by the virus, Merkel cell polyomavirus, which lives on the surface of the skin. Merkel cell carcinoma usually appears as a flesh-colored or bluish-red nodule, often on the face, head or neck. Merkel cell carcinoma is also known as neuroendocrine carcinoma of the skin.

Prognosis: A prediction of the course of a condition or disease. The prediction can include determining the likelihood of a subject to develop aggressive, recurrent disease, to survive a particular amount of time (e.g., determine the likelihood that a subject will survive 1, 2, 3 or 5 years), to respond to a particular therapy or combinations thereof.

Protein: The terms "protein," "peptide," "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I He; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr.

Sample: A sample, such as a biological sample, includes biological materials (such as nucleic acids) obtained from an organism or a part thereof, such as a plant, or animal, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated). For example, a biological sample can be bone marrow, tissue biopsies, whole blood, serum, plasma, blood cells, endothelial cells, circulating tumor cells, lymphatic fluid, ascites fluid, interstitial fluid (also known as "extracellular fluid" and encompasses the fluid found in spaces between cells, including, inter alia, gingival cervicular fluid), cerebrospinal fluid (CSF), saliva, mucous, sputum, sweat, urine, or any other secretion, excretion, or other bodily fluids.

Sensitivity: The percent of diseased individuals (individuals with prostate cancer) in which the biomarker of interest is detected (true positive number/total number of diseased× 100). Non-diseased individuals diagnosed by the test as diseased are "false positives".

Sequence identity: As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease.

Specificity: The percent of non-diseased individuals for which the biomarker of interest is not detected (true negative/total number without disease×100). Diseased individuals not detected by the assay are "false negatives." Subjects who are not diseased and who test negative in the assay, are termed "true negatives."

Standard: A substance or solution of a substance of known amount, purity or concentration. A standard can be compared (such as by spectrometric, chromatographic, or spectrophotometric analysis) to an unknown sample (of the same or similar substance) to determine the presence of the substance in the sample and/or determine the amount, purity or concentration of the unknown sample. In one embodiment, a standard is a peptide standard. An internal standard is a compound that is added in a known amount to a sample prior to sample preparation and/or analysis and serves as a reference for calculating the concentrations of the components of the sample. In one example, nucleic acid standards serve as reference values for tumor or non-tumor expression levels of specific nucleic acids. In some examples, peptide standards serve as reference values for tumor or non-tumor expression levels of specific peptides. Isotopically-labeled peptides are particularly useful as internal standards for peptide analysis since the chemical properties of the labeled peptide standards are almost identical to their non-labeled counterparts. Thus, during chemical sample preparation steps (such as chromatography, for example, HPLC) any loss of the non-labeled peptides is reflected in a similar loss of the labeled peptides.

T-Cell: A white blood cell critical to the immune response. T cells include, but are not limited to, CD4+ T cells and CD8+ T cells. A CD4+T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, a CD8 T cells is a cytotoxic T lymphocytes. In another embodiment, a CD8 cell is a suppressor T cell.

Variants: sequences derived by deletion (so-called truncation) or addition of one or more amino acids to the N-terminal and/or C-terminal end, and/or addition of one or more bases to the 5' or 3' end of the nucleic acid sequence; deletion or addition of one or more amino acids/nucleic acids at one or more sites in the sequence; or substitution of one or more amino acids/nucleic acids at one or more sites in the sequence. The antibodies and antibody fragments described herein may be altered in various ways including amino acid substitutions, deletions, truncations, and insertions. Methods for such manipulations are generally known in the art. For example, amino acid sequence variants of the enzyme can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall enzyme retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

General Description

The inventors developed a non-parametric gating method for cytometry experiments named full annotation using shaped-constrained trees (FAUST, FIGS. 1A-1E). FAUST defines cell sub-populations as modes of the joint-distribution of protein expression within each sample. Due to its dimensionality and throughput, direct non-parametric estimation of the joint distribution is infeasible for cytometry data. Instead, FAUST selects a subset of consistently well-separated protein markers using a novel depth score, bounds a standardized set of phenotypic regions containing modes of interest for the selected markers alone, and annotates those regions relative to data-derived annotation boundaries. Standardization means that the number of regions is fixed across samples but the location of the boundaries of those regions can vary from sample to sample. Consequently, FAUST clusters are annotated with biologically interpretable labels and each represents a cell sub-population with a homogeneous phenotype.

FAUST's standardization of phenotypic regions provides a common solution to three major challenges posed by sample- and batch-heterogeneity in cytometry experiments: cluster discovery, cluster matching, and cluster labeling. Since each discovered cluster is merely a collection of cells falling within a phenotypic region, clusters can have distributions whose shape varies broadly across samples. Consequently, FAUST can accommodate significant sample-to-sample heterogeneity. Similarly, since each region (and therefore each cluster) is assigned exactly one phenotypic label, the labels can be used to match clusters across samples and interpret the cell type of each cluster. An additional benefit of matching regions by phenotypic labels is robustness to sparsity since cell counts within a region can vary by orders of magnitude across samples. Here, an unbiased FAUST procedure was applied to analyze data generated from four cancer immunotherapy clinical trials and demonstrate how the disclosed approach can be used to discover candidate biomarkers correlated with outcome and perform cross-study analyses in the presence of heterogeneous marker panels.

Referring to FIGS. 1A-1E, FAUST estimates annotation boundaries for an experimental unit. An experimental unit is user defined and can be a sample, stimulation condition, subject, batch, or site. This schematic overview of FAUST provided in FIG. 1A assumes the experimental unit is an individual sample. Panel A) To estimate annotation boundaries, FAUST grows an exhaustive forest of 1-dimensional, depth-3 gating strategies, constrained by shape: if, prior to depth-3, the cells in a node of the gating strategy have unimodal expression along all markers, the gating strategy along that path terminates. Panel B) Annotation boundaries are estimated for markers within an experimental unit by averaging over gates drawn for that marker over the entire annotation forest. A "depth score" is derived for each marker and it quantifies how well-gated the marker is in each experimental unit. The distribution of scores across experimental units is used to determine whether a marker should be included in the discovery process and to determine the number of annotation boundaries a marker should receive. Panel C) This procedure ensures that FAUST selects a standard set of markers for discovery and annotation as well as a standard number of annotation boundaries per selected marker. Panel D) For each experimental unit, FAUST then relaxes the depth-3 constraint and conducts a search of 1-dimensional gating strategies in order to discover and select phenotypes present in the experimental unit. Each discovered phenotype is given a score that quantifies the homogeneity of cells in an experimental unit with that phenotype; high-scoring phenotypes are then selected for annotation. Each selected phenotype is annotated using all selected markers from Panel C), regardless of the specific gating strategy that led to the phenotype's discovery. Panel E) FAUST returns an annotated count matrix with counts of cells in each phenotypic region discovered and selected in Panel D) that also survives down-selection by frequency of occurrence across experimental units.

Figure 7:
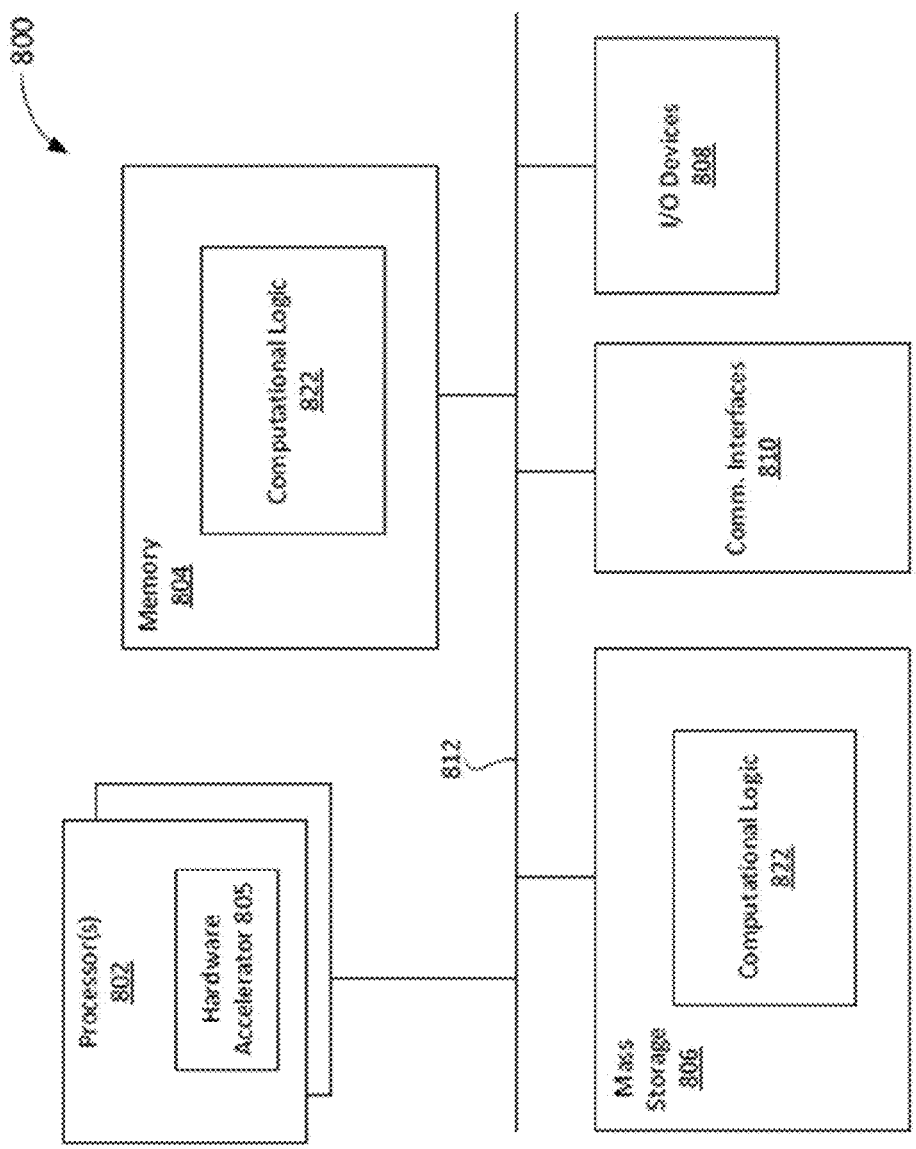
FIG. 7 illustrates a block diagram of a computer device suitable for practicing the present disclosure, in accordance with various embodiments.

In some embodiments, the disclosed method utilizes a computer device. FIG. 7 provides a block diagram of a computer device suitable for practicing the present disclosure, in accordance with various embodiments. As shown, computer device 800 can include one or more processors 802, memory controller 803, and system memory 804. Each processor 802 can include one or more processor cores, and hardware accelerator 805. An example of hardware accelerator 805 can include, but is not limited to, programmed field programmable gate arrays (FPGA). In embodiments, processor 802 can also include a memory controller (not shown). In embodiments, system memory 804 can include any known volatile or non-volatile memory.

Additionally, computer device 800 can include mass storage device(s) 806 (such as solid state drives), input/output device interface 808 (to interface with various input/output devices, such as, mouse, cursor control, display device (including touch sensitive screen), and so forth) and communication interfaces 810 (such as network interface cards, modems and so forth). In embodiments, communication interfaces 810 can support wired or wireless communication, including near field communication. The elements can be coupled to each other via system bus 812, which can represent one or more buses. In the case of multiple buses, they can be bridged by one or more bus bridges.

Each of these elements may perform its conventional functions known in the art. In particular, system memory 804 and mass storage device(s) 806 can be employed to store a working copy and a permanent copy of the executable code of the programming instructions of an operating system, one or more applications, and/or various software implemented components of a converter, binary file input interface, binary to 8-bit vector conversion, 2D array conversion, array resize, analyzer, partially retrained neural network, training, retrain and validation and classification, and computing logic 822. The programming instructions implementing computing logic 822 can comprise assembler instructions supported by processor(s) 802 or high-level languages, such as, for example, C, that can be compiled into such instructions. In embodiments, some of computing logic can be implemented in hardware accelerator 805. In embodiments, part of computational logic 822, e.g., a portion of the computational logic 822 associated with the runtime environment of the compiler may be implemented in hardware accelerator 805.

The permanent copy of the executable code of the programming instructions or the bit streams for configuring hardware accelerator 805 can be placed into permanent mass storage device(s) 806 and/or hardware accelerator 805 in the factory, or in the field, through, for example, a distribution medium (not shown), such as a compact disc (CD), or through communication interface 810 (from a distribution server (not shown)). While for ease of understanding, the compiler and the hardware accelerator that executes the generated code that incorporate the predicate computation teaching of the present disclosure to increase the pipelining and/or parallel execution of nested loops are shown as being located on the same computing device, in alternate embodiments, the compiler and the hardware accelerator can be located on different computing devices.

The number, capability and/or capacity of these elements 810-812 can vary, depending on the intended use of example computer device 800. The constitutions of these elements 810-812 are otherwise known, and accordingly will not be further described.

Figure 8:
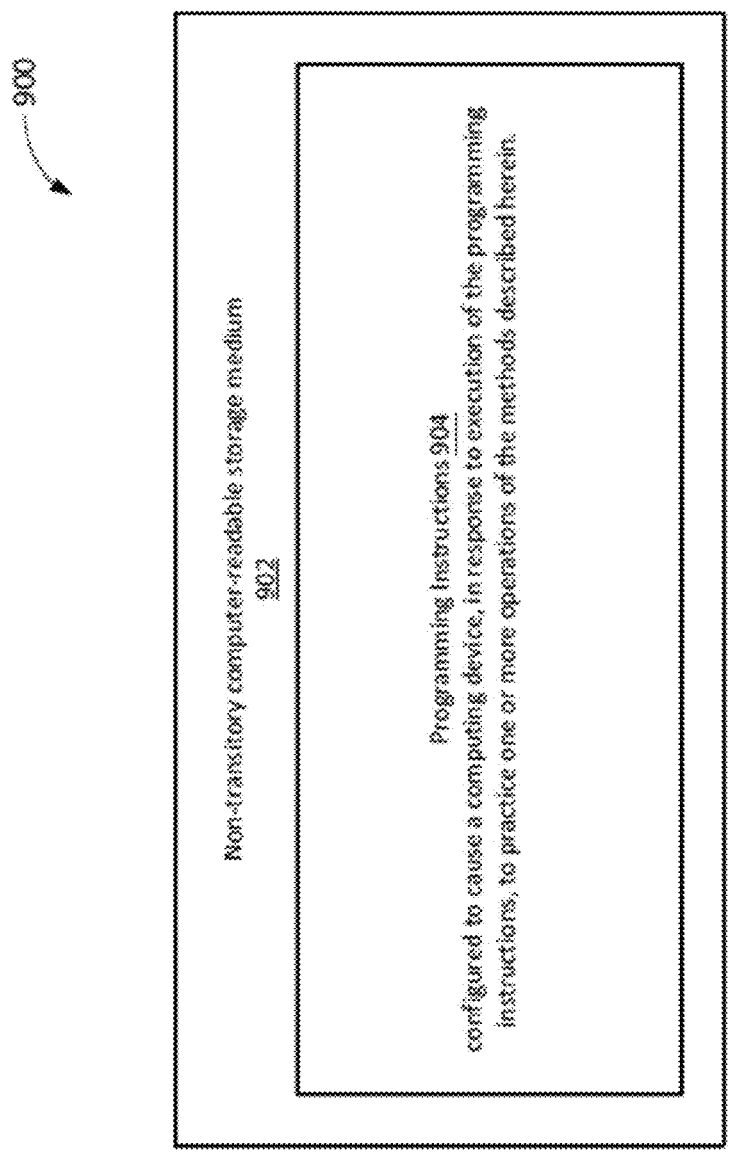
FIG. 8 illustrates an example computer-readable storage medium having instructions configured to practice aspects of the processes disclosed herein, in accordance with various embodiments.
Figure 9A:
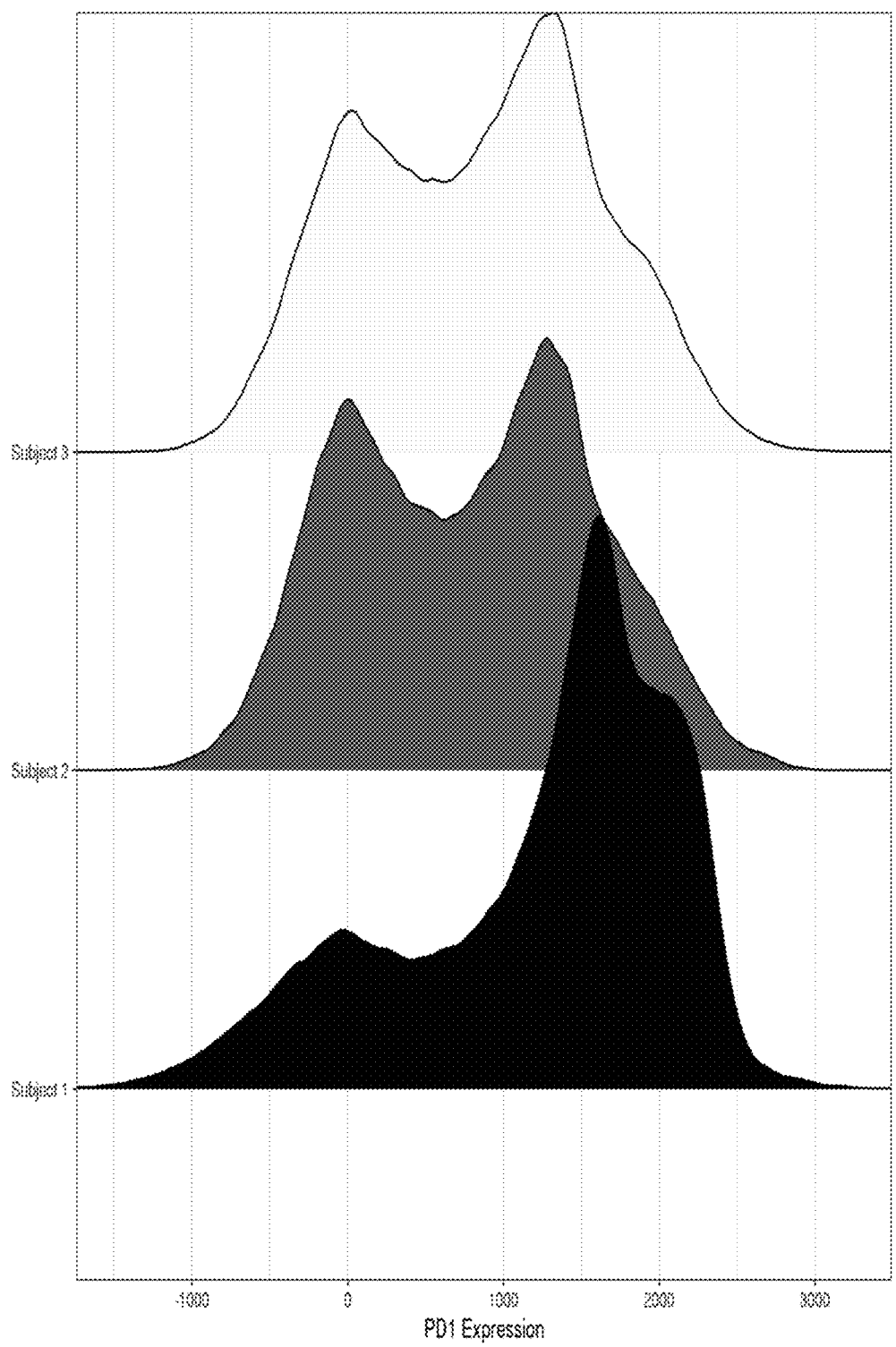
FIGS. 9A-9D show four common types of variability present in real-world cytometry experiments from clinical trials. Each panel depicts the distribution of PD-1 expression on pre-gated live lymphocytes from subjects in study CITN-09, an anti-PD-1 immunotherapy trial in Merkel Cell Carcinoma. Different types of heterogeneity in the signal can be observed. 9A) depicts biological heterogeneity across several subjects within a single time point, 9B) depicts within-subject heterogeneity across multiple time points 9C) depicts heterogeneity between two subjects with progressive disease from different cohorts, and 9D) depicts heterogeneity in a single sample associated with a chosen gating strategy, where the distribution of PD-1 is shown conditional on different upstream gating strategies.
Figure 9B:
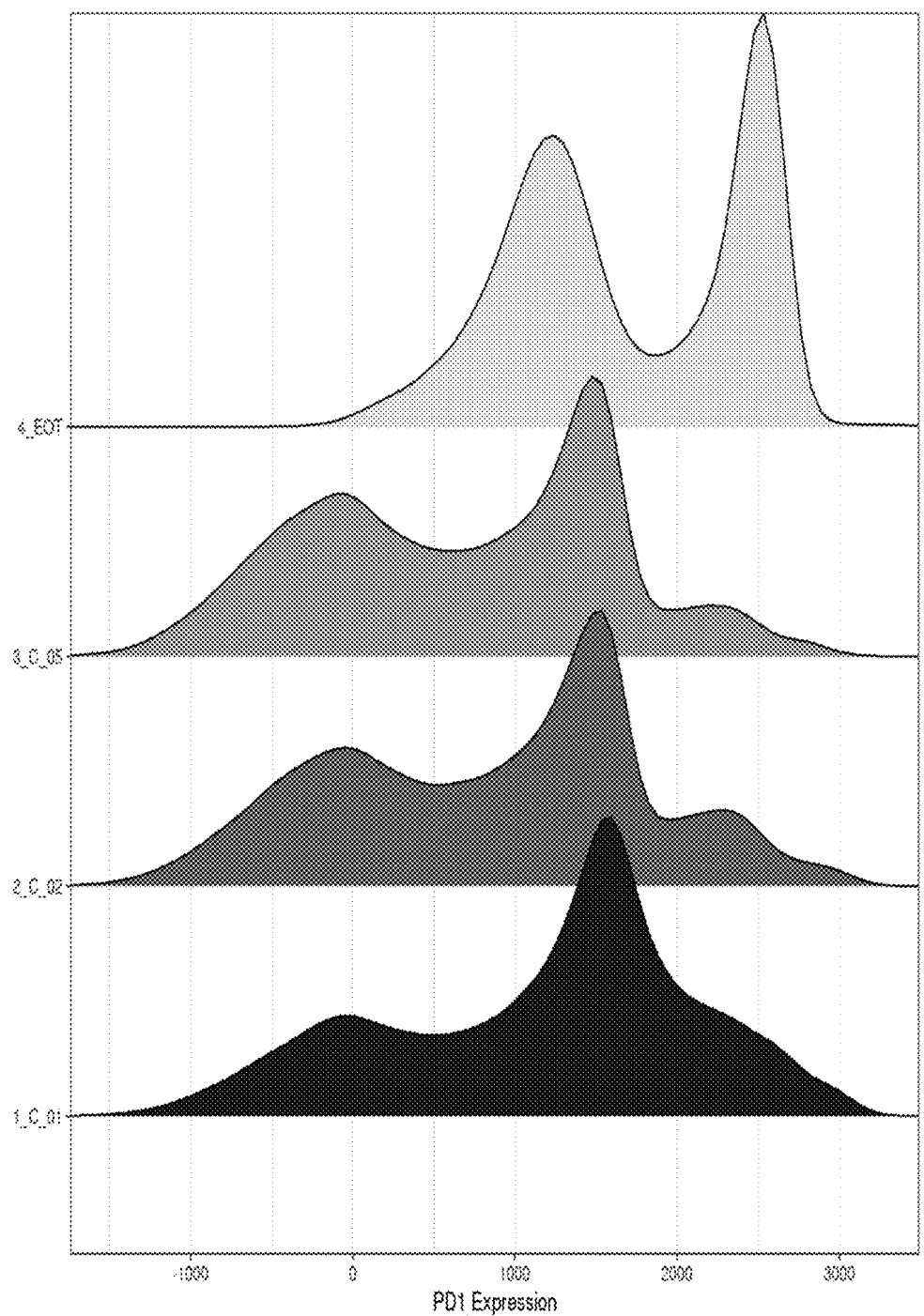
Figure 9C:
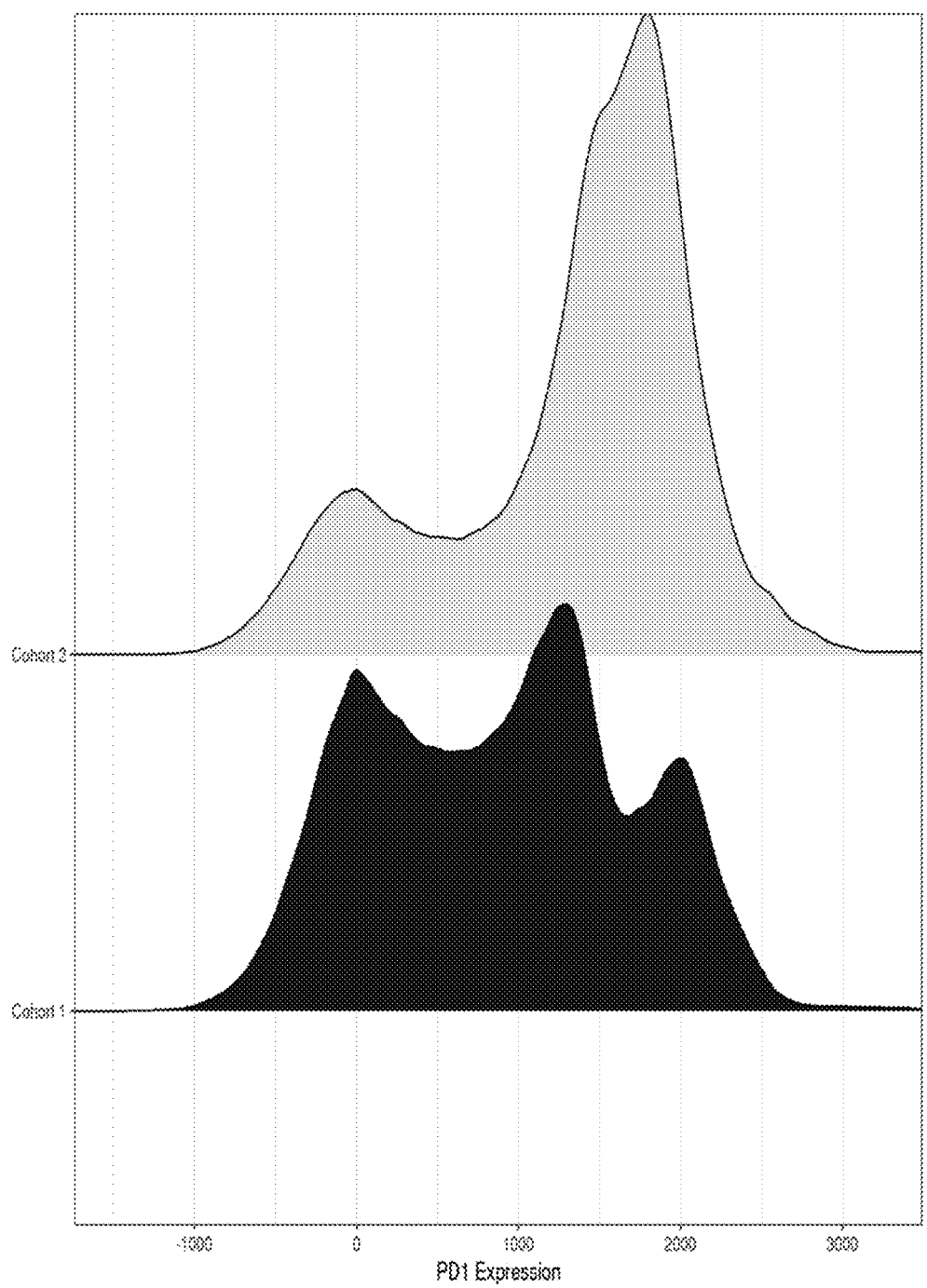
Figure 9D:
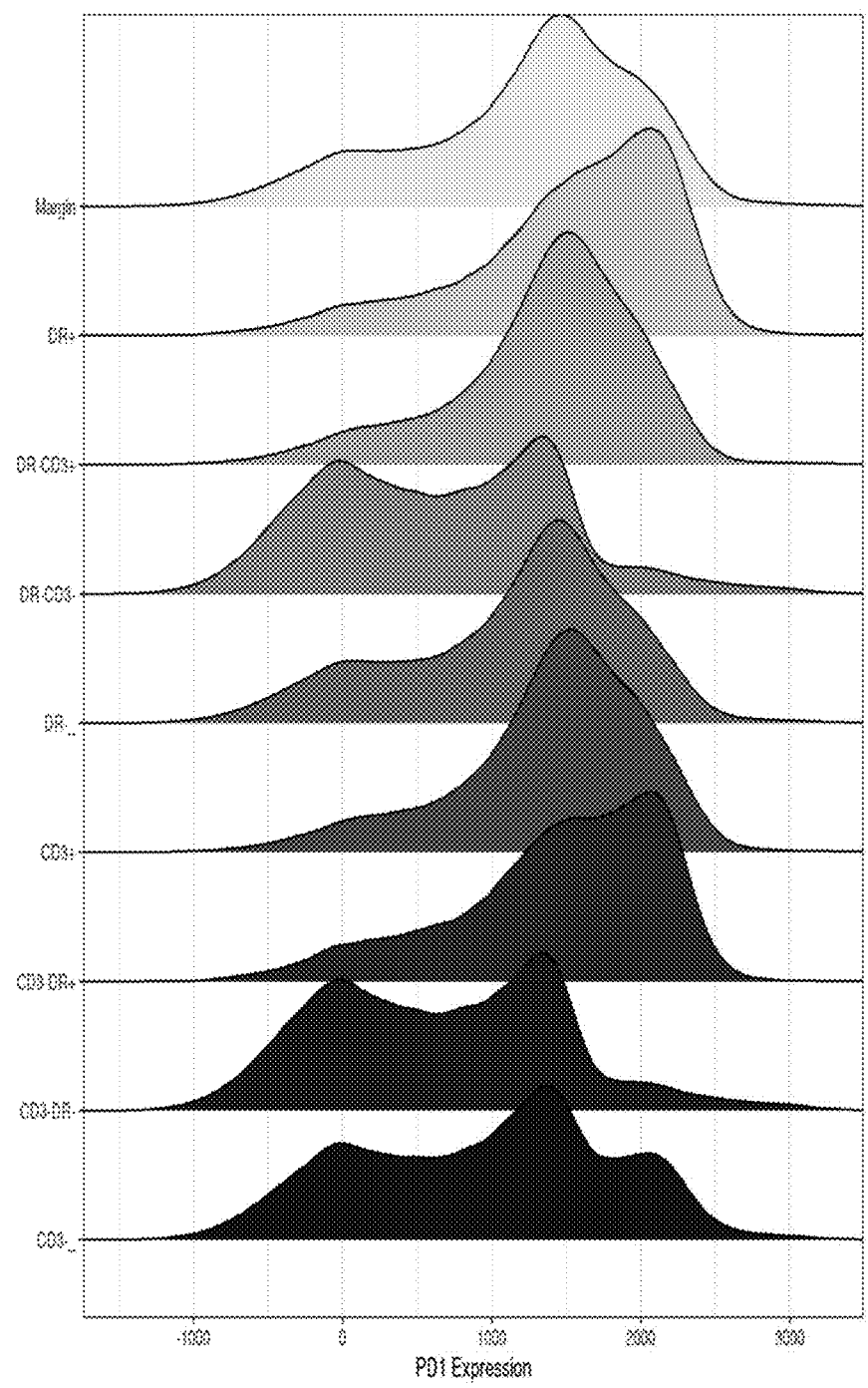

FIG. 8 illustrates an example computer-readable storage medium having instructions configured to implement all (or portion of) software implementations. As illustrated, computer-readable storage medium can include the executable code of a number of programming instructions or bit streams. Executable code of programming instructions (or bit streams) can be configured to enable a device, e.g., computer device 800, in response to execution of the executable code/programming instructions (or operation of an encoded hardware accelerator 875), to perform (aspects of) various processes. In alternate embodiments, executable code/programming instructions/bit streams 904 can be disposed on multiple non-transitory computer-readable storage medium 902 instead. In embodiments, computer-readable storage medium 902 can be non-transitory. In still other embodiments, executable code/programming instructions 904 can be encoded in transitory computer readable medium, such as signals.

Referring back to FIG. 7, for one embodiment, at least one of processors 802 can be packaged together with a computer-readable storage medium having some or all of computing logic 822 (in lieu of storing in system memory 804 and/or mass storage device 806) configured to practice all or selected ones of the operations. For one embodiment, at least one of processors 802 is packaged together with a computer-readable storage medium having some or all of computing logic 822 to form a System in Package (SiP). For one embodiment, at least one of processors 802 can be integrated on the same die with a computer-readable storage medium having some or all of computing logic 822. For one embodiment, at least one of processors 802 can be packaged together with a computer-readable storage medium having some or all of computing logic 822 to form a System on Chip (SoC). For at least one embodiment, the SoC can be utilized in, e.g., but not limited to, a hybrid computing tablet/laptop.

The disclosed methods can be used to identify cell populations by identifying candidate biomarkers associated with specific cell populations. In some examples, the markers, such as sets of markers, are used for monitoring disease states, such as cancer, in an organism, such as a mammalian subject, for example a human subject. In some examples, the method can be used to monitor the response to a therapy, disease progression and/or make treatment decisions for subjects. In some particular examples, the disclosed markers are used to monitor therapy response to immunotherapy treatment in Merkel cell carcinoma. In some examples, the disclosed markers are used to predict responsiveness to immunotherapy treatment in Merkel cell carcinoma which is virus mediated (Merkel cell polyomavirus).

In particular embodiments, disclosed are candidate biomarkers discovered and annotated by the FAUST method, and associated with patient response to immunotherapy, such as anti-PD-1 therapy, for Merkel cell carcinoma, and in particular, Merkel cell carcinoma of viral origin.

In one example, candidate biomarkers were found in baseline fresh blood samples from patients with Merkel cell carcinoma. In some examples, the phenotypes of T cell biomarkers include one or more of the follow combinations:

1. CD4− CD3+ CD8+ CD45RA− HLADR+ CD28+ PD1 Dim CD25− CD127− CCR7−
2. CD4+ CD3+ CD8− CD45RA− HLADR− CD28+ PD1 Dim CD25− CD127− CCR7−
3. CD4+ CD3+ CD8− CD45RA+ HLADR− CD28− PD1 Dim CD25− CD127+ CCR7+
4. CD4− CD3+ CD8+ CD45RA− HLADR+ CD28+ PD1 Bright CD25− CD127− CCR7−
5. CD4+ CD3+ CD8− CD45RA− HLADR+ CD28+ PD1 Dim CD25− CD127− CCR7−
6. CD4+ CD3+ CD8− CD45RA+ HLADR− CD28+ PD1− CD25− CD127+ CCR7−
7. CD4− CD3+ CD8+ CD45RA− HLADR− CD28+ PD1 Dim CD25− CD127− CCR7−
8. CD4− CD3+ CD8+ CD45RA+ HLADR− CD28− PD1 Bright CD25− CD127− CCR7−
9. CD4+ CD3+ CD8− CD45RA+ HLADR− CD28+ PD1 Dim CD25− CD127+ CCR7−
10. CD4− CD3+ CD8+ CD45RA+ HLADR− CD28− PD1 Dim CD25− CD127− CCR7−
11. CD4− CD3+ CD8+ CD45RA+ HLADR− CD28− PD1 Dim CD25+ CD127− CCR7−
12. CD4+ CD3+ CD8− CD45RA− HLADR− CD28+ PD1 Dim CD25− CD127− CCR7+
13. CD4+ CD3+ CD8− CD45RA− HLADR+ CD28+ PD1 Dim CD25− CD127− CCR7+
14. CD4− CD3+ CD8+ CD45RA− HLADR− CD28+ PD1 Bright CD25− CD127− CCR7−
15. CD4− CD3+ CD8− CD45RA+ HLADR+ CD28+ PD1 Dim CD25− CD127− CCR7−
16. CD4+ CD3+ CD8− CD45RA+ HLADR− CD28− PD1 Dim CD25− CD127− CCR7−
17. CD4+ CD3+ CD8− CD45RA+ HLADR− CD28+ PD1 Dim CD25− CD127− CCR7+. In the aforementioned listing, the phenotypes of T cell candidate biomarkers are listed in ranked order, from strongest association with responsiveness to treatment to weakest (but still statistically significant at FDR-adjusted 0.20 level).

In some examples, phenotypes of myeloid candidate biomarkers were discovered and annotated by the FAUST method, and were associated with patient response to immunotherapy. These candidate biomarkers were also found in baseline fresh blood samples from patients with Merkel cell carcinoma. For example, in some embodiments, one of more of the following combinations of candidate biomarkers were discovered to be associated with response to immunotherapy in Merkel cell carcinoma:

1. CD33 Bright CD16− CD15− HLADR Bright CD14+ CD3− CD11B+ CD20− CD19− CD56− CD11C+

2. CD33 Bright CD16− CD15− HLADR Bright CD14− CD3− CD11B+ CD20− CD19− CD56− CD11C+
3. CD33 Bright CD16− CD15+ HLADR Bright CD14+ CD3− CD11B+ CD20− CD19− CD56− CD11C+
4. CD33 Bright CD16+ CD15+ HLADR Bright CD14+ CD3− CD11B+ CD20− CD19− CD56− CD11C+
5. CD33 Bright CD16− CD15− HLADR Bright CD14− CD3− CD11B− CD20− CD19− CD56− CD11C+
6. CD33 Dim CD16+ CD15+ HLADR Bright CD14+ CD3− CD11B+ CD20− CD19− CD56− CD11C+
7. CD33− CD16− CD15− HLADR Dim CD14+ CD3− CD11B+ CD20− CD19− CD56− CD11C+
8. CD33 Dim CD16− CD15+ HLADR Dim CD14− CD3− CD11B+ CD20− CD19− CD56− CD11C−
9. CD33 Dim CD16+ CD15+ HLADR Bright CD14− CD3− CD11B+ CD20+CD19+ CD56− CD11C−
10. CD33 Bright CD16− CD15− HLADR Dim CD14+ CD3− CD11B+ CD20− CD19− CD56− CD11C+
11. CD33 Dim CD16− CD15+ HLADR Bright CD14+ CD3− CD11B+ CD20− CD19− CD56− CD11C+
12. CD33 Dim CD16+ CD15+ HLADR Dim CD14− CD3+ CD11B+ CD20− CD19− CD56− CD11C−
13. CD33 Dim CD16− CD15− HLADR Bright CD14− CD3− CD11B+ CD20− CD19− CD56− CD11C+
14. CD33 Dim CD16− CD15+ HLADR− CD14− CD3− CD11B+ CD20− CD19− CD56− CD11C−
15. CD33 Bright CD16− CD15− HLADR Dim CD14+ CD3− CD11B+ CD20− CD19− CD56− CD11C−
16. CD33 Dim CD16− CD15+ HLADR− CD14− CD3− CD11B− CD20− CD19− CD56− CD11C−
17. CD33 Dim CD16− CD15− HLADR Dim CD14− CD3− CD11B− CD20− CD19− CD56− CD11C+
18. CD33− CD16− CD15− HLADR Bright CD14− CD3− CD11B+ CD20− CD19− CD56+ CD11C+
19. CD33 Dim CD16− CD15− HLADR Dim CD14− CD3− CD11B− CD20− CD19− CD56− CD11C−.

In the aforementioned listing, the phenotypes are listed in ranked order, from strongest association with responsiveness to treatment to weakest (but still statistically significant at FDR-adjusted 0.20 level).

Appropriate samples for use in the methods disclosed herein include any conventional biological sample obtained from an organism (including samples from a healthy or apparently healthy human subject or a human patient affected by a condition or disease to be diagnosed or investigated, such as cancer). In some particular examples, the biological sample is blood sample. The biological sample may be examined using any assay format that is capable of detecting desired molecules including immunohistology techniques, ELISA, Western Blotting, and the like.

The disclosed markers may be used to identify as well predict a subject's responsiveness to immunotherapy treatment of Merkel cell carcinoma and in particular, Merkel cell carcinoma of viral origin. Changes in the profile can also represent the progression (or regression) of the disease process. Methods for monitoring the efficacy of therapeutic agents are described herein. The diagnostic methods of the present disclosure are valuable tools for practicing physicians including for monitoring a subject for onset and/or advancement of a particular condition and/or disease, including Merkel cell carcinoma. The methods disclosed herein can also be used to monitor the effectiveness of a therapy. Following the measurement of the expression levels of one or more of the molecules identified herein, the assay results, findings, diagnoses, predictions and/or treatment recommendations can be recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the Merkel cell carcinoma biomarkers disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283, 761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having Merkel cell carcinoma results in the physician treating the subject, such as prescribing one or more therapeutic agents for inhibiting or delaying one or more signs and symptoms associated with Merkel cell carcinoma, including use of anti-PD-1 therapy. In additional embodiments, the dose or dosing regimen is modified based on the information obtained using the methods disclosed herein.

The subject can be monitored while undergoing treatment using the methods described herein in order to assess the efficacy of the treatment protocol. In this manner, the length of time or the amount give to the subject can be modified based on the results obtained using the methods disclosed herein.

The following examples are provided to illustrate certain particular features and/or embodiments. These examples should not be construed to limit the disclosure to the particular features or embodiments described.

EXAMPLE

A Method for Unbiased Cell Population Discovery and Annotation Reveals Correlates of Clinical Response to Cancer Immunotherapy FAUST identifies baseline CD8+ T cells in blood that correlate with outcome in CITN-09, a Merkel cell carcinoma anti-PD-1 trial. FAUST was used to perform cell subpopulation discovery in cytometry data generated by the Cancer Immunotherapy Trials Network (CITN) from study CITN-09, a phase 2 clinical trial of the Pembrolizumab anti-PD-1 therapy in Merkel cell carcinoma (MCC), with the goal of identifying baseline correlates of response to treatment (Nghiem et al., Durable tumor regression and overall survival in patients with advanced merkel cell carcinoma receiving pembrolizumab as first-line therapy. Journal of Clinical Oncology, 37(9):693-702, 2019. PMID: 30726175). Seventy-eight stained samples were analyzed to identify T cells. FAUST selected 10 markers for discovery and annotation, including the marker CD3. Since the panel was designed to investigate T cells, only these CD3+ sub-populations were used for downstream correlates analysis.

Binomial generalized linear mixed models (GLMMs) (Nowicka et al., Cytof workflow: differential discovery in high-throughput high-dimensional cytometry datasets. F1000Research, 6, 2017, which is hereby incorporated by reference in its entirety) were used to test each sub-population for differential abundance between responders and non-responders in the 27 subjects at the baseline time point, prior to receiving anti-PD-1 therapy (equation (4.5) specifies the model). Responders were defined as subjects that exhibited either a complete (CR) or partial (PR) response (per RECIST1.1 (Eisenhauer et al., New response evaluation criteria in solid tumours: Revised (RECIST) guideline (version 1.1). European Journal of Cancer, 45(2):228-247, 2009. Response assessment in solid tumours (RECIST): Version 1.1 a), and non-responders as subjects exhibiting progressive (PD) or stable (SD) disease. At a false discovery rate (FDR)-adjusted 5% level (Yoav Benjamini and Yosef Hochberg. Controlling the false discovery rate: a practical and powerful approach to multiple testing. Journal of the royal statistical society. Series B (Methodological), pages 289-300, 1995), four FAUST phenotypes were associated with response to therapy. Two had a CD28+ HLA-DR+ CD8+ annotation, with PD-1 dim or PD-1 bright, respectively. The third had an HLA-DR− CD28+ CD4+ PD-1 dim annotation, while the fourth had an HLA-DR− CD28− CD4+ PD-1 dim annotation. Effect sizes with 95% confidence intervals for the correlates are reported in Table 6. Three of the four correlates were annotated CD45RA− and CCR7−, indicating they represented effector-memory T cells. The complete phenotypes are described in FIGS. 2A-2C.

Figure 2A:
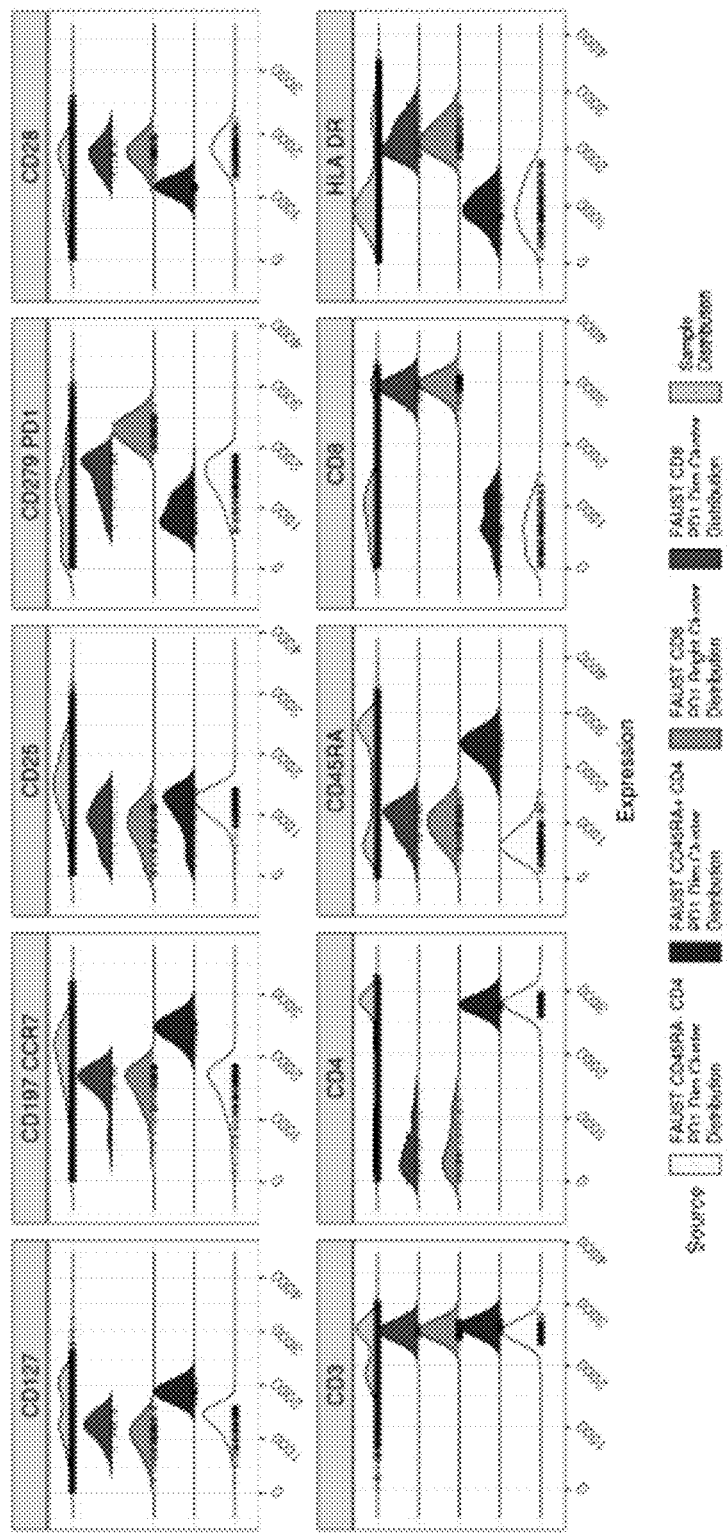

The primary flow cytometry data was inspected to confirm that the discovered population phenotypes matched the underlying protein expression. By plotting cluster densities against samples (FIG. 2A), the FAUST annotations accurately described the observed cellular phenotypes in these sub-populations. These data were also visualized using UMAP embeddings (McInnes et al., UMAP: Uniform Manifold Approximation and Projection for Dimension Reduction. ArXiv e-prints, February 2018) with "qualitative" parameter settings (Becht et al., Dimensionality reduction for visualizing single-cell data using umap. Nature biotechnology, 37(1):38, 2019) (FIGS. 2B, 2C). FAUST clusters were not typically separated into disjoint "islands" in the UMAP embedding (FIG. 2C), and that single UMAP "islands" contained significant variation in expression of some of the measured protein markers (FIG. 2B). Taken together, these observations demonstrate that dimensionality reduction does not necessarily reflect all variation measured in the underlying proteins, and that any method that relies on UMAP for population discovery would likely miss these candidate biomarkers.

Figure 3A:
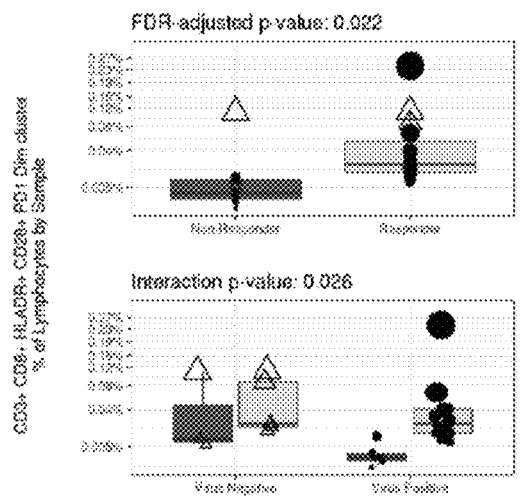
FIGS. 3A-3C show a CD8+ PD-1 dim CD28+ HLADR+ T cell sub-population discovered by FAUST is associated with outcome in virus positive subjects and with independent measurements of PD1 and T cell clonality in the tumor. 3A) Boxplots of the abundance of the CD8+ PD-1 dim CD28+ HLADR+ T cell outcome correlate discovered by FAUST, stratified by subjects' response to therapy (FDR adjusted p-value contrasting all responders vs all non-responders: 0.022) and their viral status (unadjusted p-value of interaction: 0.026). 3B) The abundance of the CD8+ PD-1 dim CD28+ HLADR+ T cell correlate among virus positive subjects against total PD-1 expression measured by IHC from tumor biopsies, with observed correlation in virus positive subjects of 0.942. 3C) The abundance of the CD8+ PD-1 dim CD28+ HLADR+ T cell correlate among virus positive subjects plotted against productive clonality (1—normalized entropy) from tumor samples, with observed correlation in virus positive subjects of 0.959.
Figure 3B:
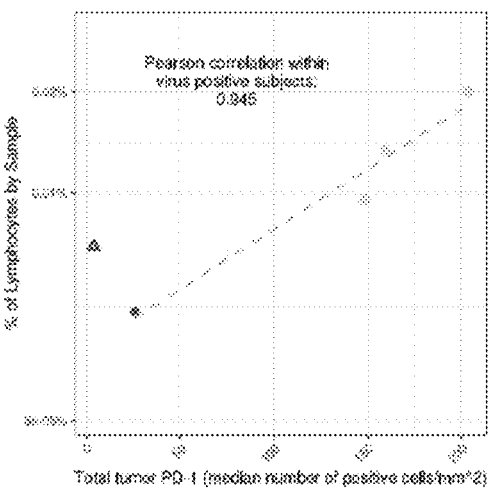
Figure 3C:
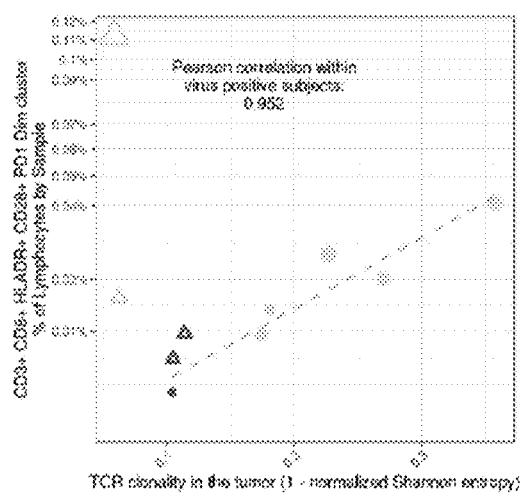
Figure 10A:
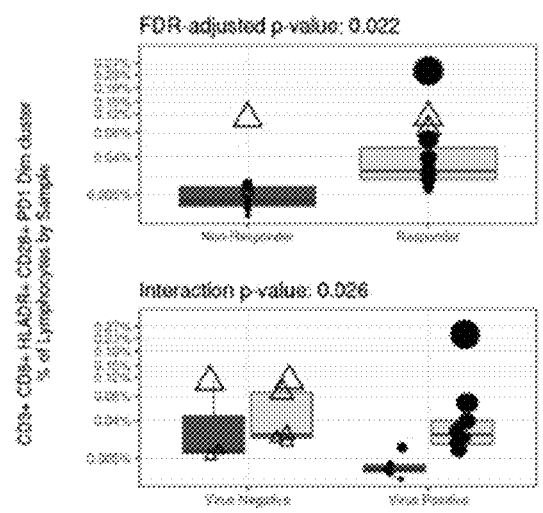
FIGS. 10A-C provide the same FAUST subpopulation reported in FIGS. 3A-3C—CD4− CD3+ CD8+ CD45RA− HLA-DR+ CD28+ PD-1 dim CD25− CD127− CCR7-—normalized by the total count of CD3+ FAUST sub-populations by sample in panel 3C.
Figure 10B:
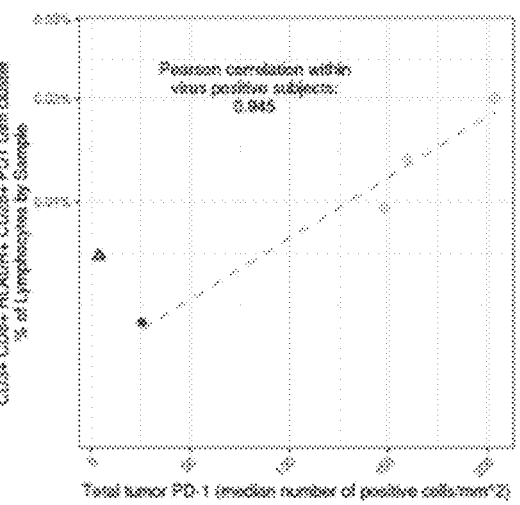
Figure 10C:
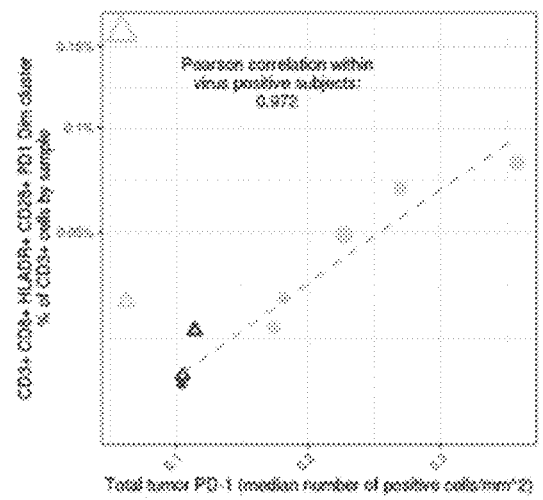

The association between the abundance of the discovered correlates and tumor viral status of each subject was next investigated. The differential abundance GLMM were adapted to test for an interaction between response to therapy and tumor viral status. This interaction was statistically significant for both CD8+ correlates (FIG. 3A), indicating that these T cells are particularly relevant in subjects with virus-positive tumors. In order to further investigate the relevance of these T cells measured in blood, data on PD-1 immunohistochemistry (IHC) staining in tumor biopsies from the same patients was acquired (Miller et al., Merkel cell polyomavirus-specific immune responses in patients with merkel cell carcinoma receiving anti-pd-1 therapy. Journal for immunotherapy of cancer, 6(1):131, 2018). Importantly, the in-tumor PD-1 measurement is a known outcome correlate in MCC (Giraldo et al., Multidimensional, quantitative assessment of pd-1/pd-l1 expression in patients with merkel cell carcinoma and association with response to pembrolizumab. Journal for immunotherapy of cancer, 6(1):99, 2018). Limited overlap between the assays resulted in only five subjects where both flow cytometry and tumor biopsy anti-PD-1 IHC staining were available, and only four of these were virus-positive. Nonetheless, the frequencies of the CD8+ PD-1 dim T cells were strongly correlated ($\rho=0.945$) with the PD-1 total IHC measurements within the four virus-positive subjects (FIG. 3B). TCR clonality data generated from patient tumor samples was obtained (Miller et al., Merkel cell polyomavirus-specific immune responses in patients with merkel cell carcinoma receiving anti-pd-1 therapy. Journal for immunotherapy of cancer, 6(1):131, 2018). Ten subjects passing clonality QC were common to the two data sets, six of which were virus positive. Frequencies of the FAUST populations within these six subjects were strongly correlated ($\rho=0.952$) with the measurement of productive clonality (FIG. 3C). Normalizing the correlate cell counts by the total number of CD3+ annotated FAUST sub-populations (i.e., total T cells, the recommended normalization constant for T cell clonality) instead of total lymphocyte count improved the observed correlation to $\rho=0.972$ (FIGS. 10A-C).

Figure 11A:
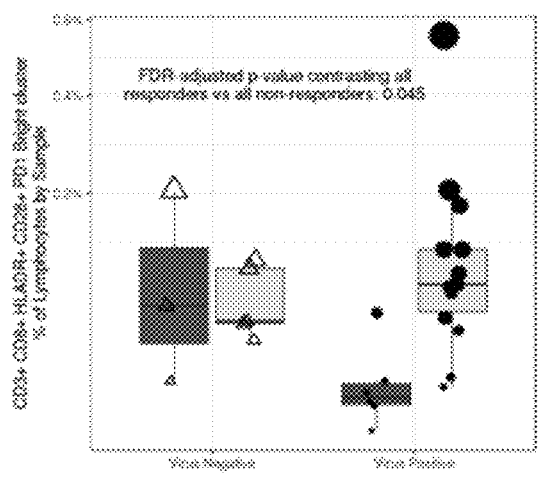
FIGS. 11A-11C provide the FAUST sub-population annotated CD4− CD3+ CD8+CD45RA− HLA-DR+ CD28+ PD-1 bright CD25− CD127− CCR7− that is associated with clinical outcome at the FDR-adjusted 5% level, with tumor measurements in FIGS. 11B and 11C.
Figure 11B:
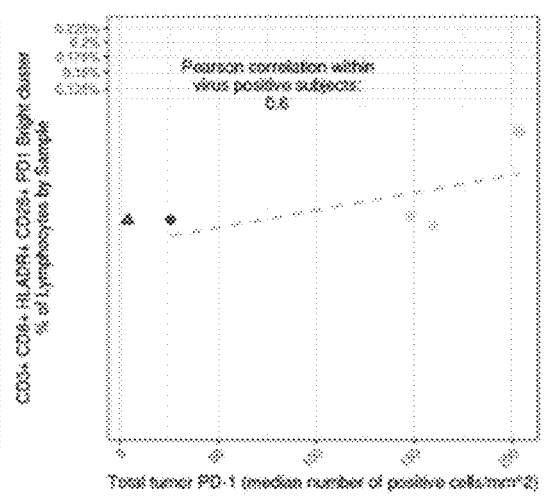
Figure 11C:
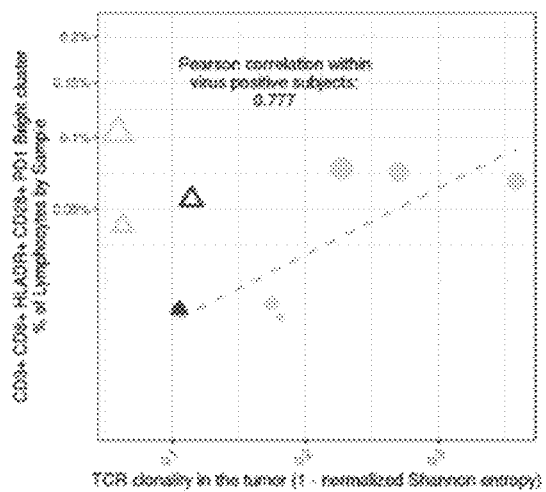

FIGS. 11A-11C provide the FAUST sub-population annotated CD4− CD3+CD8+ CD45RA− HLA-DR+ CD28+ PD-1 bright CD25− CD127− CCR7− that is associated with clinical outcome at the FDR-adjusted 5% level, with tumor measurements in FIGS. 11B and 11C. FIGS. 12A-12C provide the FAUST sub-population annotated CD4 bright CD3+ CD8− CD45RA− HLA-DR− CD28+ PD-1 dim CD25− CD127− CCR7− that is associated with clinical outcome at the FDR-adjusted 5% level, with tumor measurements in FIGS. 12B and 12C. FIGS. 13A-13C provide the FAUST sub-population annotated CD4 bright CD3+ CD8− CD45RA+ HLA-DR− CD28− PD-1 dim CD25− CD127+ CCR7+ that is associated with clinical outcome at the FDR-adjusted 5% level, with tumor measurements in FIGS. 13B and 13C.

Together, these results suggest that the CD8+ T cell correlate discovered by FAUST in blood may represent a circulating population of tumor-associated virus-specific T cells that are also detectable in the tumor.

Subsequent to this initial analysis, FAUST was used to test the hypothesis that the increased pre-treatment abundance of the top CD8+ correlate and top CD4+ correlate discovered by FAUST in the MCC trial are associated with positive response to pembrolizumab treatment by applying FAUST to the public dataset described in Subramanyam et al. (Distinct predictive biomarker candidates for response to anti-ctla-4 andanti-pd-1 immunotherapy in melanoma patients. Journal for immunotherapy of cancer, 6(1):18, 2018). FAUST was applied only to unstimulated baseline PBMC samples.

Before applying FAUST to the public dataset, the pre-gating strategy reported by Subramanyam et al. was replicated using the computational package openCyto (Finak et al., Opencyto: an open source infrastructure for scalable, robust, reproducible, and automated, end-to-end flow cytometrydata analysis. PLoS computational biology, 10(8):

e1003806, 2014). FAUST was used to estimate data-driven annotation threshold for the 10 annotating markers selected in the unbiased MCC analysis. These thresholds were used to extract per-sample counts of the top CD8+ and CD4+ phenotypes matching those produced by FAUST in the MCC analysis. In the CyTOF dataset of Subramanyam et al., FAUST defined one standardized annotation threshold for all ten markers (including CD4 and PD-1). On the other hand, in the MCC study FAUST defined two thresholds for CD4 and PD-1, and one threshold for the other markers. Therefore, to extract corresponding counts in the CyTOF dataset, PD-1+ cells were treated as comparable to the FAUST phenotypes PD-1 dim and PD-1 bright in the MCC study; the same map was used for CD4+ cells in the CyTOF dataset.

Figure 30:
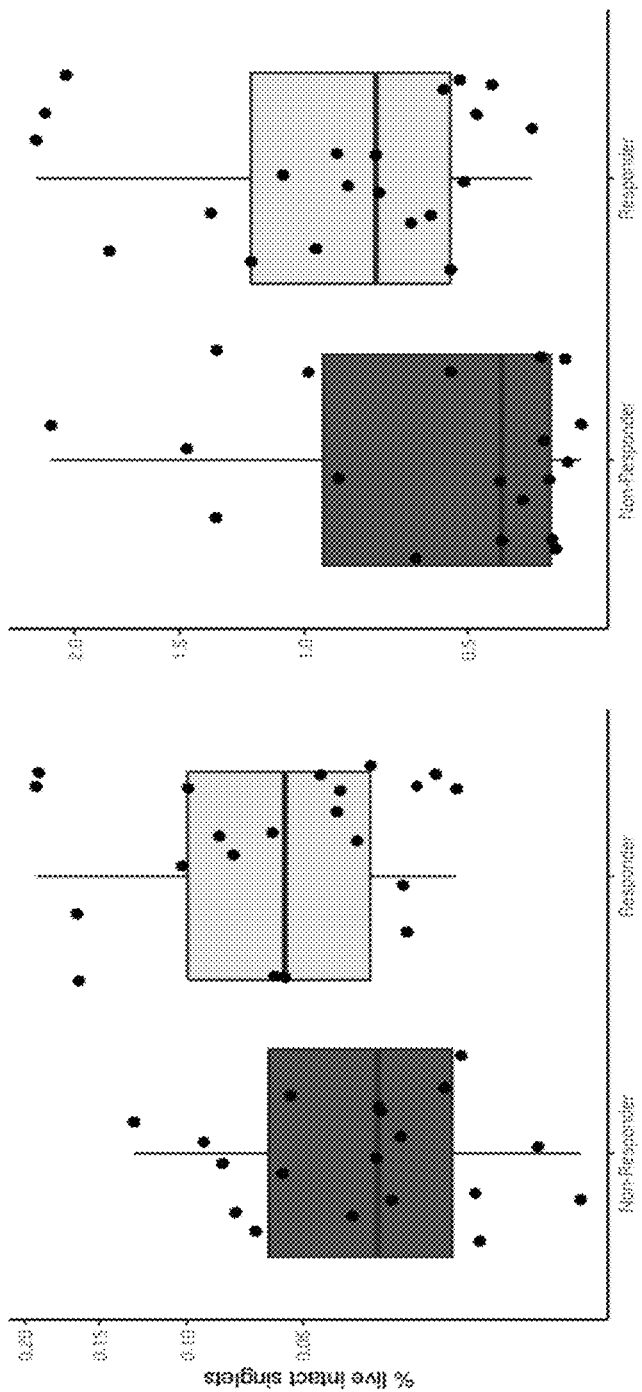
FIGS. 30A and 30B showTop FAUST phenotypes validated in an independent melanoma trial.

The extracted counts for the top CD8+ phenotype and top CD4+ phenotype were then tested for differential abundance between responders and non-responders in pre-treatment samples from subjects that went on to receive the anti-PD-1 therapy pembrolizumab. Subjects in the CyTOF dataset were defined as subjects that exhibited progression-free survival for at least 180 days. Increased abundance was observed in responding subjects for the top CD8+ phenotype and top CD4+ phenotype defined by FAUST (FIGS. 30A-30B), validating the associations detected by FAUST in the MCC analysis, and demonstrating that FAUST can be used to perform targeted validation across studies and technologies.

Figures 4A, 4B:
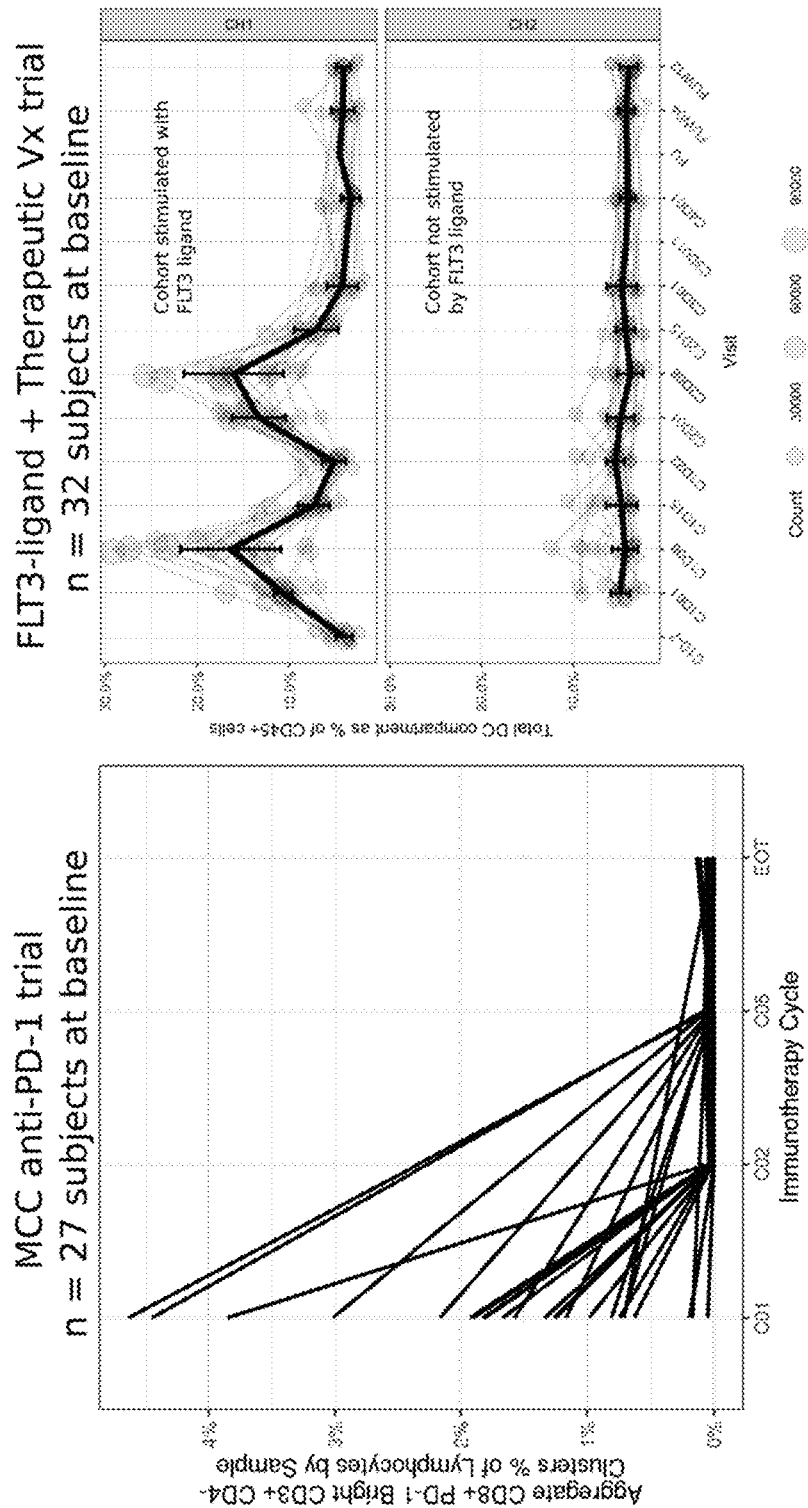
FIGS. 4A and 4B provide the longitudinal profiles of aggregated FAUST cell populations in a pembrolizumab therapy trial and a FLT3-L+ CDX-1401 trial. 4A) The frequency of all CD8+ PD-1-bright T-cell populations found by FAUST across all time points. 4B) The longitudinal profiles of all cell sub-populations with phenotypes consistent with the DC compartment: CD19−, CD3−, CD56−, HLA-DR+, CD14− CD16− and CD11C+/−. Light colored lines show individual subjects. The dark line shows the median across subjects over time. Error bars show the 95% confidence intervals of median estimate at each time point. Cohort 1 (n=16 subjects), cohort 2 (n=16 subjects).
Figures 5A, 5B:
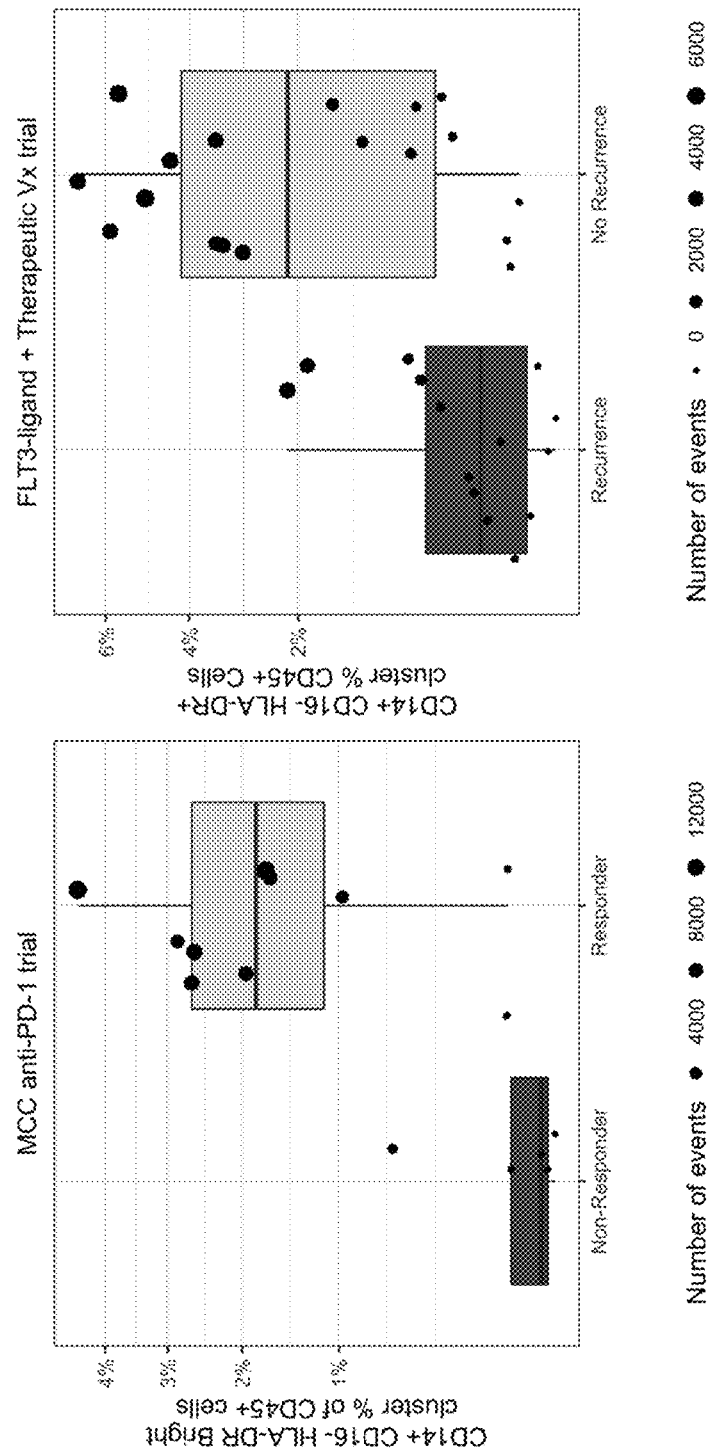
FIGS. 5A-5D demonstrate FAUST consistently discovers CD14+ CD16-HLADR+ monocytes associated with outcome at baseline across immunotherapy trials. 5A) The baseline correlate of outcome discovered by FAUST in the MCC anti-PD-1 trial myeloid data. The full FAUST annotation for the correlate was CD33 bright CD16− CD15− HLA–DR bright CD14+ CD3− CD11B+ CD20− CD19− CD56− CD11C+. 5B) The baseline correlate discovered by FAUST in the FLT3-L therapeutic Vx trial myeloid data. The full FAUST annotation for the correlate was CD8− CD3− HLA-DR+ CD4− CD19− CD14+CD11C+ CD123− CD16− CD56−. 5C) The baseline correlate found by FAUST from the re-analysis of the Krieg CyTOF panel 03 (stratified by batch). The full FAUST annotation for the correlate was CD16− CD14+ CD11B+ CD11C+ ICAM1+ CD62L− CD33+ PDL1+ CD7− CD56− HLA-DR+. 5D) The baseline correlate found by FAUST from the re-analysis of the Krieg FACS validation data. The full FAUST annotation for the correlate was CD3− CD4+ HLA-DR+ CD19− CD14+ CD11B+ CD56− CD16− CD45RO+.
Figures 5C, 5D:
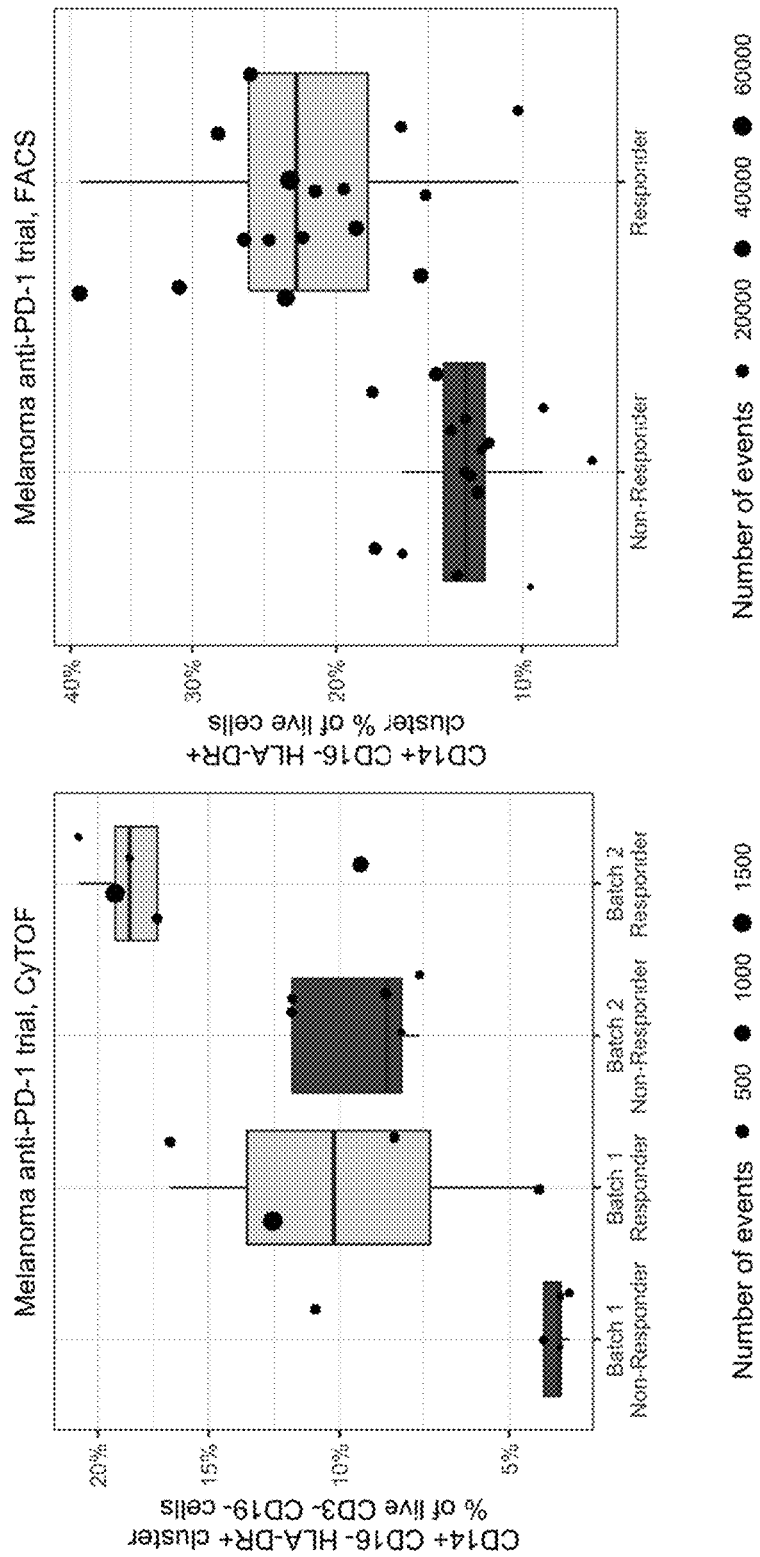

FAUST Sub-Populations Capture Underlying Biological and Technical Signals in Longitudinal Studies FAUST's sample-specific processing and phenotypic standardization enables the identification of cell sub-populations whose abundances differ or may be absent across different subsets of experimental samples. In the MCC anti-PD-1 trial, all CD8+ T cells with the PD-1-bright phenotype were examined. The temporal abundance of these cells is shown in (FIG. 4A) and reveals that these cells are not detectable in most samples after subjects have received pembrolizumab therapy. The absence of these phenotypes post-therapy is hypothesized to occur due to pembrolizumab blocking the detecting antibody. FAUST was also applied to data generated from CITN-07, a randomized phase II trial studying how a DEC-205/NY-ESO-1 fusion protein (CDX-1401) and a neoantigen-based melanoma poly-ICLC vaccine (poly-ICLC) therapy work when given with or without recombinant FLT3 ligand (CDX-301) in treating patient with stage IIB to stage IV melanoma. The cytometry data consisted of fresh PBMCs stained for myeloid cell phenotyping.

Examination of the longitudinal profile of clusters with phenotypic annotations consistent with dendritic cells (FIG. 4B) revealed dynamic expansion and contraction of the total DC compartment in the FLT3-L stimulated cohort but not in the unstimulated-by-FLT3-L-pre-treatment cohort. The expansion peaked at day 8 after FLT3-L simulation in cycles 1 and 2. This dynamic is consistent with observations from manual gating of the DC population (Bhardwaj et al., A phase ii randomized study of cdx-1401, a dendritic cell targeting ny-eso-1 vaccine, in patients with malignant melanoma pre-treated with recombinant cdx-301, a recombinant human flt3 ligand. Journal of Clinical Oncology, 34(15): 9589, 2016) and consistent with the expected biological effect of FLT3-L (Fong et al., Altered peptide ligand vaccination with flt3 ligand expanded dendritic cells for tumor immunotherapy. Proc. Natl. Acad. Sci. U.S.A., 98(15):8809-8814, July 2001) as well as the timing of FLT3 administration.

These results demonstrate that FAUST is able to detect, annotate, and correctly assign abundance to cell sub-populations, including those that are missing in some samples. The longitudinal behavior of PD-1 bright T cell populations in the MCC anti-PD-1 trial and the dendritic cells in the FLT3 ligand+CDX-1401 trial serve as an internal validation of the methodology.

FAUST Identifies Phenotypically Similar Myeloid Sub-Populations Associated with Clinical Response Across Multiple Cancer Immunotherapy Trials.

Both the MCC anti-PD-1 and FLT3-L+therapeutic Vx trials had data sets stained with a myeloid phenotyping panel. FAUST was applied to two additional myeloid phenotyping data sets (one CyTOF discovery and one FACS validation assay) from an anti-PD-1 trial in metastatic melanoma (Krieg et al., High-dimensional single-cell analysis predicts response to anti-pd-1 immunotherapy. Nature medicine, 24(2):144, 2018). In the following, these are referred to as the melanoma anti-PD-1 FACS and melanoma anti-PD-1 CyTOF data sets. In each study, a different staining panel was used to interrogate the myeloid compartment. A principal finding of the melanoma anti-PD-1 trial was that the frequency of CD14+ CD16− HLA-DRhi cells associated with response to therapy. In all four data sets FAUST identified cell sub-populations associated with clinical outcome (FDR-adjusted 5% level, using binomial GLMMs to test for differential abundance) whose phenotype was consistent with the previously-published CD14+ CD16− HLA-DRhi phenotype (FIGS. 5A-5D). Complete phenotypes, effect sizes and confidence intervals for the myeloid baseline predictors discovered in the MCC anti-PD-1 myeloid phenotyping data are in Table 1; those discovered in the FLT3-L+therapeutic Vx trial are in Table 2. These results demonstrate the power of the disclosed method to detect candidate biomarkers in a robust manner across different platforms, staining panels, and experimental designs.

TABLE 1

All statistically significant (Bonferroni adjusted significance threshold of 5%) from the MCC anti-PD-1 trial.

| Population | Effect Size | Lower 2.5% | Upper 97.5% | BonferroniP |
|---|---|---|---|---|
| CD33 Bright CD16− CD15− HLADR Bright CD14− CD3− CD11B− CD20− CD19− CD56− CD11C+ | 2.611 | 1.073 | 4.162 | 0.041 |
| CD33 Bright CD16− CD15− HLADR Bright CD14− CD3− CD11B+ CD20− CD19− CD56− CD11C+ | 2.776 | 1.316 | 4.274 | 0.009 |
| CD33 Bright CD16− CD15− HLADR Bright CD14+ CD3− CD11B+ CD20− CD19− CD56− CD11C+ | 3.558 | 1.837 | 5.284 | 0.002 |

TABLE 1-continued

All statistically significant (Bonferroni adjusted significance threshold of 5%) from the MCC anti-PD-1 trial.

| Population | Effect Size | Lower 2.5% | Upper 97.5% | BonferroniP |
|---|---|---|---|---|
| CD33 Bright CD16− CD15+ HLADR Bright CD14+ CD3− CD11B+ CD20− CD19− CD56 − CD11C+ | 3.689 | 1.859 | 5.823 | 0.007 |
| CD33 Bright CD16+ CD15+ HLADR Bright CD14+ CD3− CD11B+ CD20− CD19− CD56− CD11C+ | 4.754 | 2.353 | 7.578 | 0.011 |

The complete set of baseline predictors from the FLT3-L+therapeutic Vx trial are listed in Table 2. The top populations, by magnitude, were CD14+CD16-monocyte populations.

TABLE 2

All statistically significant (Bonferroni adjusted significance threshold of 5%) from the FLT3-L + therapeutic Vx trial.

| Population | estimate | lower | upper | std. error | statistic | p. value | adjusted. p. value |
|---|---|---|---|---|---|---|---|
| CD8−CD3−HLA DRbright CD4−CD19−CD14+CD11C+CD123−CD16−CD56− | 2.44 | 1.16 | 3.73 | 0.66 | 3.73 | 9.70e−05 | 0.01 |
| CD8−CD3−HLA DRdimCD4−CD19−CD14+CD11C+CD123−CD16−CD56− | 2.26 | 1.22 | 3.31 | 0.54 | 4.23 | 1.17e−05 | 0.00 |
| CD8dim CD3−HLA DRbright CD4−CD19−CD14+CD11C+CD123−CD16−CD56− | 2.14 | 0.98 | 3.29 | 0.59 | 3.62 | 1.46e−04 | 0.02 |
| CD8dim CD3−HLA DRdim CD4−CD19−CD14−CD11C−CD123−CD16+CD56+ | 1.91 | 0.93 | 2.89 | 0.50 | 3.82 | 6.67e−05 | 0.01 |
| CD8dim CD3−HLA DR−CD4−CD19−CD14−CD11C−CD123−CD16+CD56+ | 1.60 | 0.73 | 2.47 | 0.44 | 3.59 | 1.64e−04 | 0.02 |
| CD8−CD3−HLA DRdim CD4−CD19−CD14−CD11C−CD123−CD16+CD56+ | 1.60 | 0.69 | 2.50 | 0.46 | 3.47 | 2.65e−04 | 0.03 |
| CD8bright CD3+HLA DRbright CD4−CD19−CD14−CD11C−CD123−CD16−CD56− | 1.50 | 0.71 | 2.29 | 0.40 | 3.72 | 1.01e−04 | 0.01 |
| CD8dim CD3−HLA DRdim CD4−CD19−CD14−CD11C−CD123−CD16−CD56− | 1.23 | 0.75 | 1.70 | 0.24 | 5.07 | 2.01e−07 | 0.00 |
| CD8−CD3−HLA DRbright CD4−CD19−CD14−CD11C−CD123−CD16−CD56− | 1.22 | 0.60 | 1.83 | 0.32 | 3.85 | 5.90e−05 | 0.01 |
| CD8−CD3−HLA DRdimCD4−CD19−CD14−CD11C−CD123−CD16+CD56− | 1.12 | 0.68 | 1.56 | 0.22 | 5.02 | 2.64e−07 | 0.00 |
| CD8dim CD3−HLA DR−CD4−CD19−CD14−CD11C−CD123−CD16+CD56− | 0.97 | 0.58 | 1.35 | 0.20 | 4.92 | 4.34e−07 | 0.00 |
| CD8−CD3−HLA DR−CD4−CD19−CD14−CD11C−CD123−CD16+CD56− | 0.92 | 0.53 | 1.30 | 0.20 | 4.67 | 1.49e−06 | 0.00 |
| CD8−CD3−HLA DRdim CD4−CD19−CD14−CD11C−CD123−CD16−CD56− | 0.75 | 0.31 | 1.19 | 0.22 | 3.38 | 3.64e−04 | 0.05 |

FAUST Enables Cross-Study Comparisons Between Different Marker Panels

FAUST annotations enable the use of prior biological knowledge of hierarchical relationships among cell types to test hypotheses that cannot immediately be tested in the absence of cluster labels. By jointly modeling the annotated populations related through biological hierarchy, FAUST can be used to account for this dependence structure when conducting secondary tests of interests. This is analogous to the techniques used to perform gene set enrichment analysis in gene expression data (Weimar et al., Peripheral blood manipulation significantly affects the result of dendritic cell monitoring. Transplant immunology, 17(3):169-177, 2007). This approach is contrasted against aggregating (i.e., summing) cell sub-population counts on the basis of their common annotations to derive ancestral populations that resemble those obtained by manual gating.

To demonstrate this FAUST was used to test each of four different myeloid sub-compartments for association with outcome at baseline in each of the three trials with heterogeneous marker panels. FAUST annotations were used to define membership in the myeloid compartment (described below). All FAUST sub-populations that were annotated as lineage negative (CD3−, CD56−, CD19−) and expressing HLA-DR (either dim or bright) were selected as part of the myeloid compartment. Myeloid sub-compartments were defined in terms of a sub-population's CD14 and CD16 expression, with CD14− CD16− cells defined as dendritic cells, and other combinations as double-positive, CD14+, or CD16+ monocytes, respectively.

Two models were fit to each data set. First, a multivariate model of all candidate cell sub-populations was fit, and the cell sub-populations' model coefficients were aggregated over each sub-compartment to test for increased abundance in responders vs. non-responders at baseline. This model represents the cell population analog of gene set enrichment analysis. Second, a univariate model was fit to cell counts derived by summing over each myeloid sub-compartment, producing a single coefficient to test for increased abundance in responders vs. non-responders at baseline. This represents the modeling approach one would undertake if the myeloid sub-compartments were defined using a manual gating strategy. 95% confidence intervals were adjusted to 99% to account for multiple comparisons (Bonferroni correction for five tests). Details of both models are provided in the Methods disclosed herein.

Figure 20:
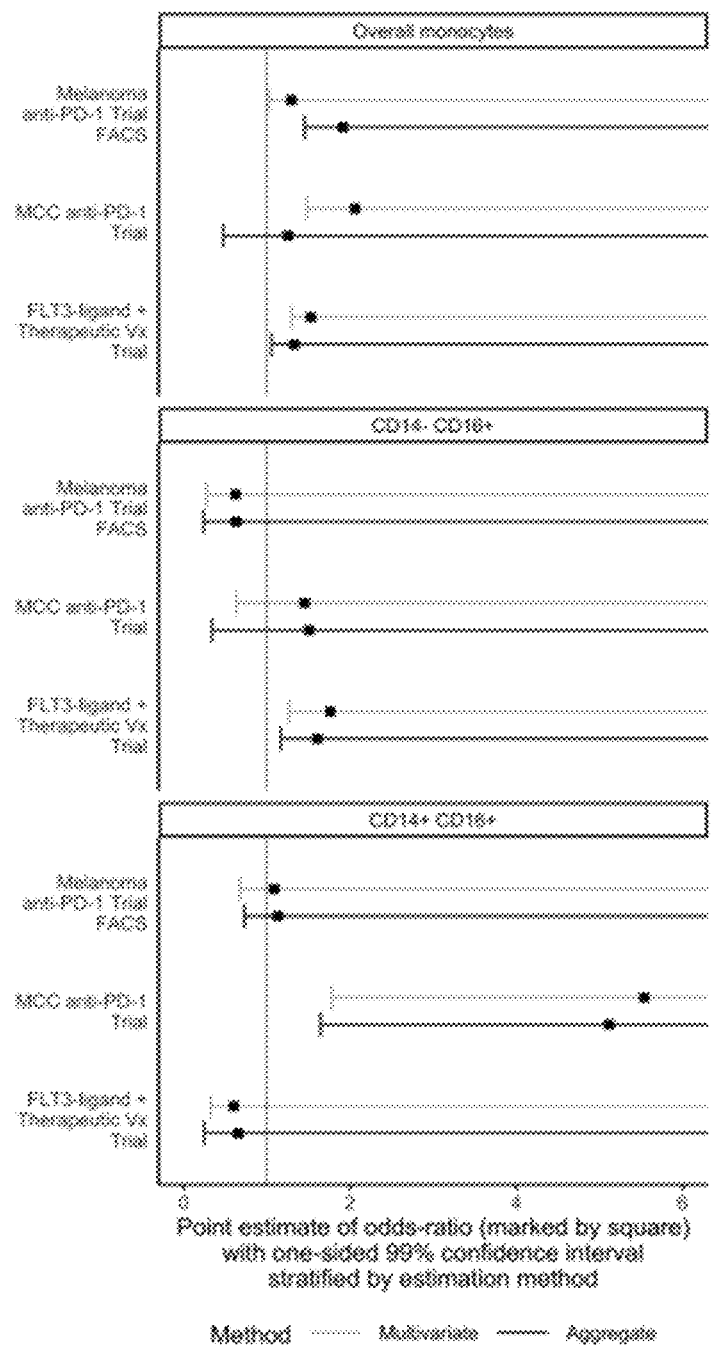
FIG. 20 provides results for the remaining compartments from the multivariate and aggregate myeloid compartment analysis described herein showing the multivariate modeling also reveals evidence of increased abundance in responders across the entire myeloid compartment.

In the aggregate model, significantly increased abundance of the CD14+ CD16− sub-compartment among responders (FIG. 6A) was observed only in the melanoma anti-PD-1 trial FACS data set, consistent with the validation analysis where they manually gated monocytes. Statistically significant differential abundance was not detected in either CITN trial data set using the aggregate model. In contrast, when differential abundance tests were performed by aggregating model coefficients over homogeneous sub-populations (thereby accounting for dependence structure), significantly increased abundance was observed in the CD14+ CD16− monocyte sub-compartment across all data sets. These results highlight that sub-populations defined by manual gating may not exhibit differential abundance when they don't capture all the heterogeneity in a cell population. The multivariate modeling strategy also detected a significant association between outcome and differential abundance in the CD14− CD16− dendritic cell sub-compartment (FIG. 6B) in the two CITN trials, consistent with the analysis of baseline predictors in those trials. Such an association was not detected in the DC sub-compartment in the Melanoma anti-PD1 trial. The latter used frozen PBMC samples while both the CITN trials used fresh blood samples for analysis. Reports have shown that the functional characteristics of monocytes are not adversely affected by cryopreservation, while the relative abundance of pDCs and mDCs can be affected. Difference in cryopreservation status could provide an explanation for the observed differences in modeling outcomes for the DC sub-compartment (Pardali et al., Cryopreservation of primary human monocytes does not negatively affect their functionality or their ability to be labelled with radionuclides: basis for molecular imaging and cell therapy. EJNMMI research, 6(1):77, 2016); Gerrits et al., Peripheral blood manipulation significantly affects the result of dendritic cell monitoring. Transplant immunology, 17(3):169-177, 2007). This multivariate modeling approach demonstrates how FAUST can enable cross-study data integration and analysis even in the presence of heterogeneous staining panels. FIG. 20 provides results for the remaining compartments from the multivariate and aggregate myeloid compartment analysis described herein showing the multivariate modeling also reveals evidence of increased abundance in responders across the entire myeloid compartment.

FAUST is Robust to Different Data Generating Processes

Figure 14:
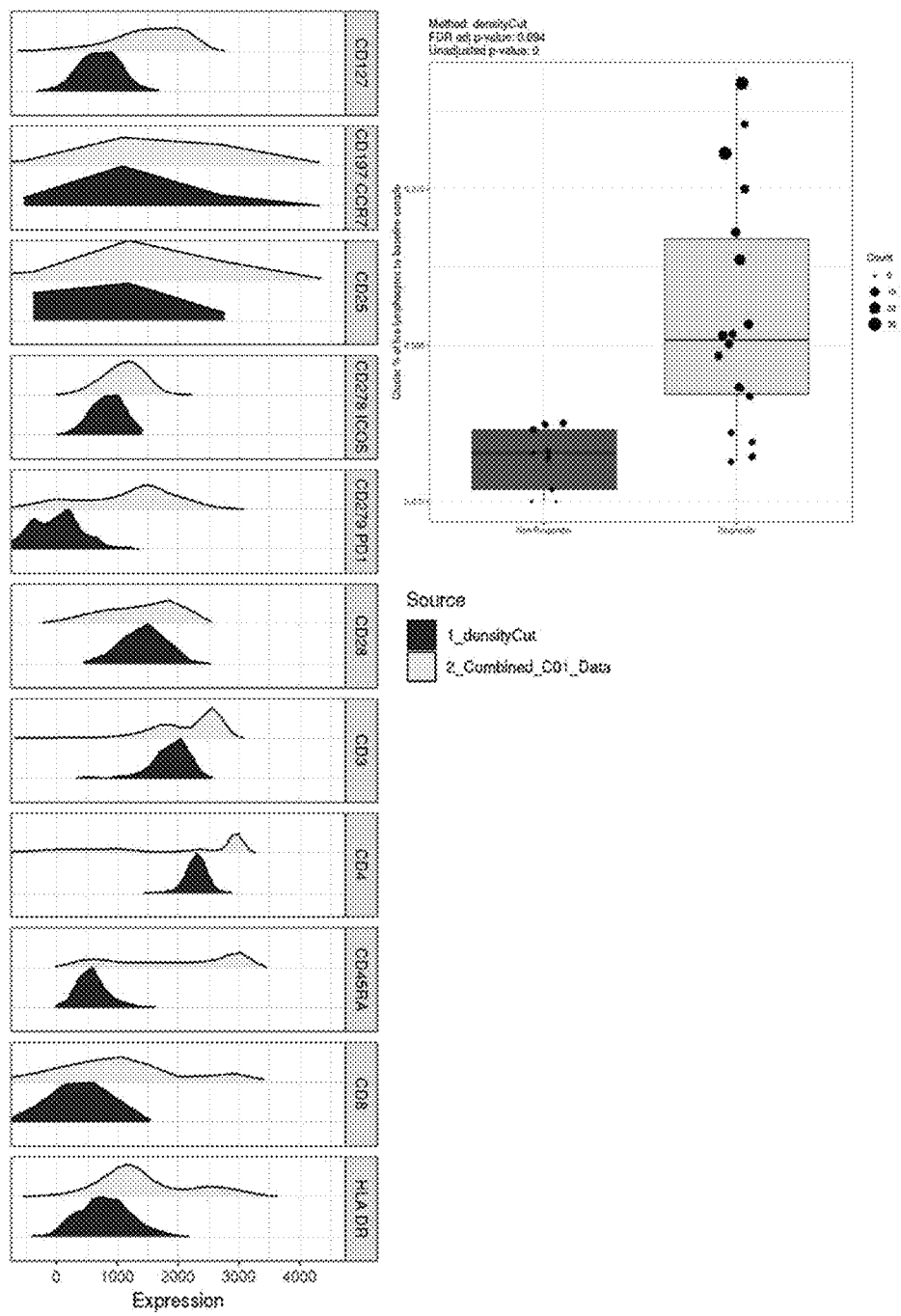
FIG. 14 shows the statistically significant correlate determined by running DensityCut on the baseline CITN-09 samples. DensityCut was installed using the command devtools::install_bitbucket("jerry00/densitycut_dev") in R 3.5.0, to install version 0.0.1 of the package. DensityCut was run unsupervised: the K parameter is set to its default value log 2(N). Two of the correlating densityCut clusters contained 2 and 20 cells in total across baseline samples, and were only measured in 1 and 2 of the 27 baseline subjects, respectively. The observed correlation for these clusters were viewed as artifactual. Plots of the third cluster's expression relative to the baseline samples (displayed in this figure) indicated that the cluster was CD3−, and so is not a T cell subset.

The clustering methods densityCut (Ding et al., densitycut: An efficient and versatile topological approach for automatic clustering of biological data. Bioinformatics, 32(17):2567-2576, 2016, which is hereby incorporated by reference in its entirety), FlowSOM (Van Gassen et al., Flowsom: Using self-organizing maps for visualization and interpretation of cytometry data. Cytometry Part A, 87(7):636-645, 2015, which is hereby incorporated by reference), Phenograph (Levine et al., Data-driven phenotypic dissection of aml reveals progenitor-like cells that correlate with prognosis. Cell, 162(1):184-197, 2015) and FAUST were applied to live lymphocytes from all 78 experimental samples as well as from the 27 baseline samples alone in the MCC anti-PD-1 T cell dataset, transforming samples using both the biexponential as well as the hyperbolic arcsine. For all non-FAUST methods, samples were combined before clustering in all scenarios. Tuning parameters were set to the settings reported in (Lukas M Weber and Mark D Robinson. Comparison of clustering methods for high-dimensional single-cell flow and mass cytometry data. Cytometry Part A, 89(12):1084-1096, 2016, which is hereby incorporated by reference] when possible. After testing for differential abundance between responders and non-responders using counts derived from each method's clusterings, three clusters defined by densityCut were significantly associated with response to therapy at the FDR-adjusted 0.20 level, but none of these represented T cells (FIG. 14). No other clusters produced by densityCut, FlowSOM, or Phenograph were associated with response to therapy at this level of significance. On the other hand, FAUST repeatedly found that CD28+ HLA-DR+ PD-1 expressing effector-memory CD8 T cells as well as CD28+ PD-1 expressing CD4 T cells were associated with response to therapy at baseline across all tested conditions at the FDR-adjusted 5% level.

Simulate studies that generated data according to FAUST's methodological assumptions were conducted. The study generated data sets from a variety mixture models incorporating different combinations of assumptions detailed in the methods disclosed herein. These assumptions are quite general, so the study begins by simulating data from multivariate gaussian distributions (data sets which are favorable to many existing methods) and progressively simulates data that more closely represents flow cytometry and CyTOF data sets. In the study, FAUST is compared to FlowSOM since FlowSOM is computationally efficient. Each simulated mixture component (representing a cell sub-population) is partially parameterized by a mean vector and is given a phenotypic label that describes the phenotype of the component. By treating these phenotypic labels as ground-truth, it is possible to measure how well the count matrix produced by FAUST agrees with the simulated count matrix, matching discovered and simulated cell populations based on their phenotypes.

Figure 25:
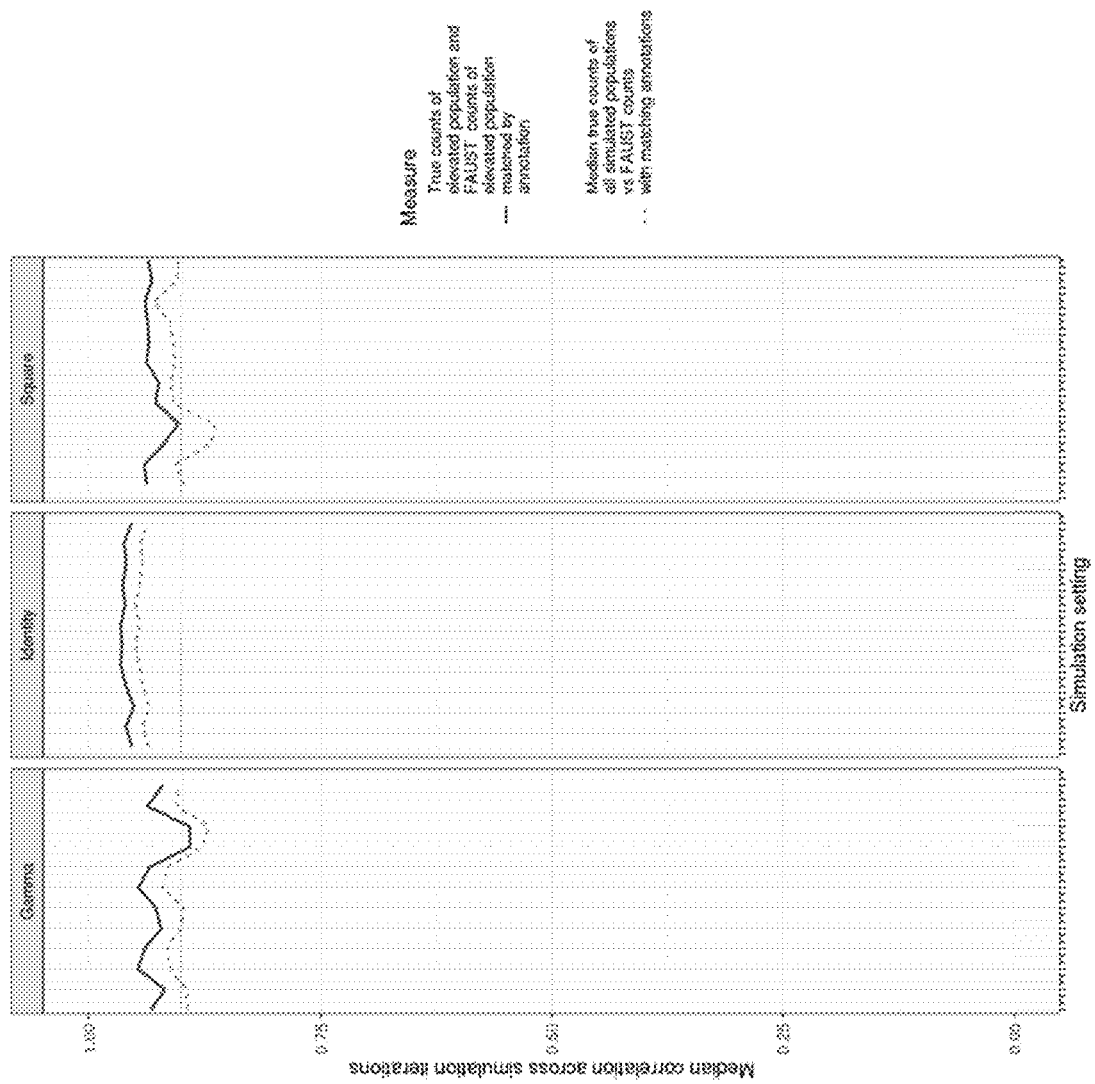
FIG. 25 provides a dashed line: median correlation across 50 simulation between all FAUST clusters and all simulated true populations Solid line: median correlation across 50 simulations between FAUST cluster with differential abundant population and simulated differentially abundant cluster. Correlations are determined only using annotations.
Figure 26:
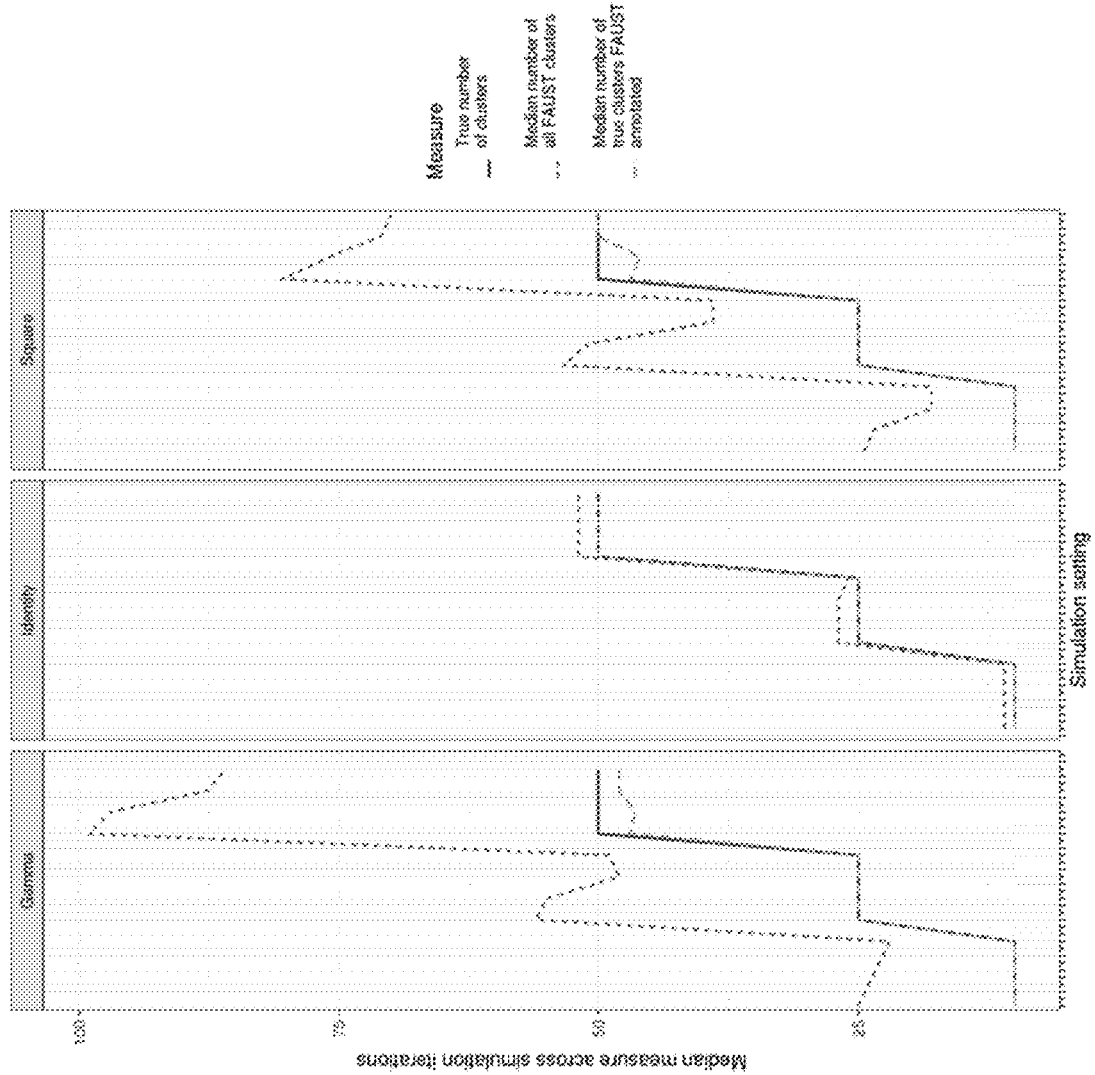
FIG. 26 provides the true number of clusters by simulation setting is the solid purple line. The dashed line shows the median number of clusters matching the true annotations produced by FAUST across simulation settings. The dot-dashed line shows the median number of total annotated clusters produced by FAUST across simulation settings.

The simulation studies demonstrate that FAUST's discovery and annotation strategy does not severely over partition the data under a variety of generative regimes (FIG. 26). Results also show that the cell counts derived from FAUST's discovered clusters strongly correlate with the underlying true counts across all simulation settings. A median correlation of 0.91 was observed between FAUST and the simulated truth, when cluster counts are correlated between FAUST clusters and the ground truth using only cluster annotations to perform the comparison (FIG. 25).

Figure 27:
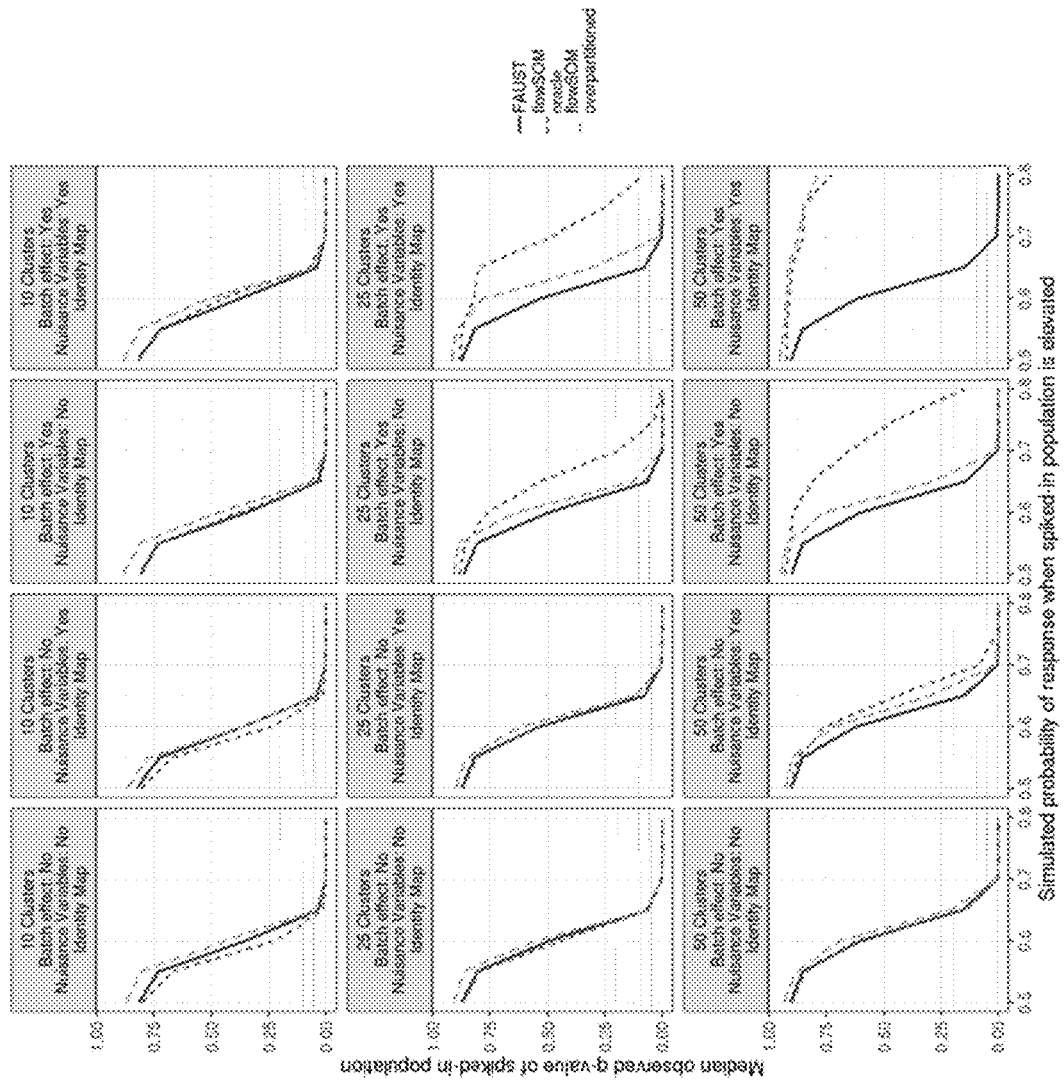
FIG. 27 illustrates in each simulation, a differentially abundant sub-population is always simulated: 50 subjects have increased abundance relative to the other 50 subjects. For subjects with increased abundance, a stochastic response to therapy is then 50 times, with the response rate for subjects with increased abundance varying along the x-axis. Median FDR-adjusted p-value of FAUST cluster annotated with the differentially abundant population, and median FDR-adjusted for FlowSOM clusters identified as the true clusters are reported across 50 iterations. This plot reports performance when data are generated from a multivariate normal mixture, with different simulation settings.
Figure 28:
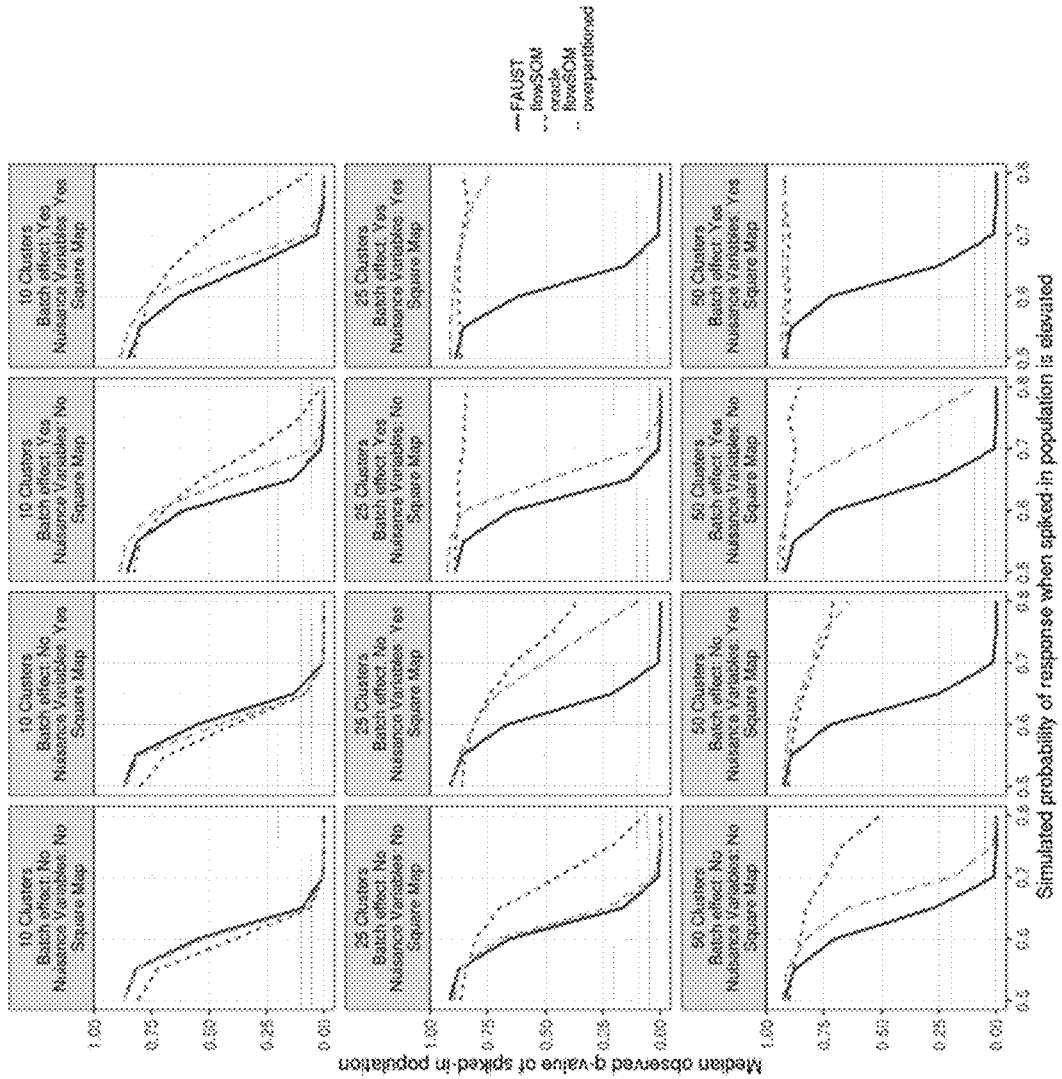
FIG. 28 illustrates in each simulation, a differentially abundant sub-population is always simulated: 50 subjects have increased abundance relative to the other 50 subjects. For subjects with increased abundance, a stochastic response to therapy is then 50 times, with the response rate for subjects with increased abundance varying along the x-axis. Median FDR-adjusted p-value of FAUST cluster annotated with the differentially abundant population, and median FDR-adjusted for FlowSOM clusters identified as the true clusters are reported across 50 iterations. This plot reports performance when data are transformed by the coordinate map $f(x)=x^2$, with different simulation settings.
Figure 29:
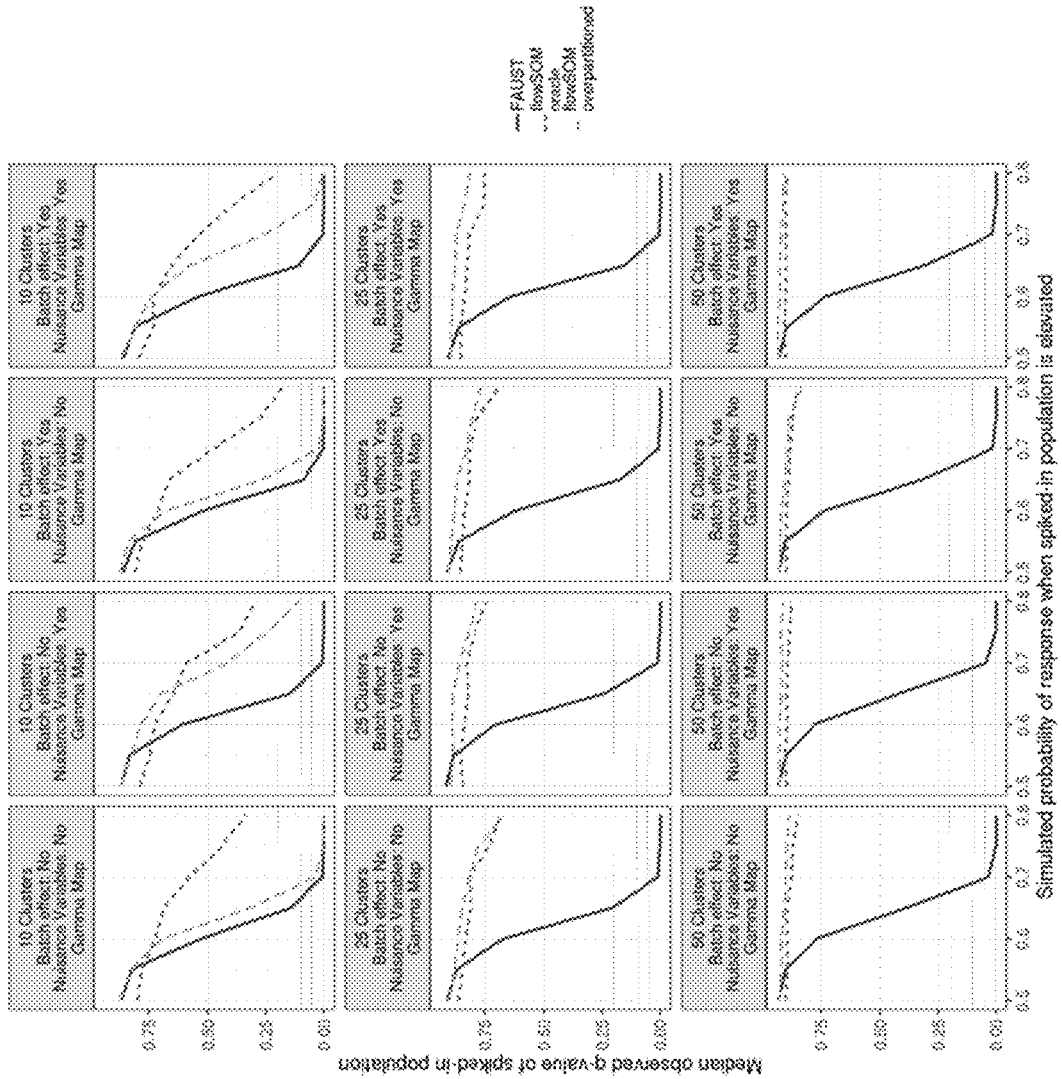
FIG. 29 illustrates in each simulation, a differentially abundant sub-population is always simulated: 50 subjects have increased abundance relative to the other 50 subjects. For subjects with increased abundance, a stochastic response to therapy is then 50 times, with the response rate for subjects with increased abundance varying along the x-axis. Median FDR-adjusted p-value of FAUST cluster annotated with the differentially abundant population, and median FDR-adjusted for FlowSOM clusters identified as the true clusters are reported across 50 iterations. This plot reports performance when data are transformed by the coordinate map $g(x)=\Gamma(1+x/4)$, with different simulation settings.

The simulated data sets always include a sub-population that is differentially abundant between 50% of the subjects. These results show that when a causal relationship of varying strength is simulated between this differential sub-population and a simulated response to therapy, FAUST discovers the differential sub-population, annotates it correctly, and often identifies that the differential population is associated with response to therapy (FIGS. 27-29).

In the present simulation, FlowSOM clusters were tested for differential abundance under the same causal regimes as FAUST. The results show that FlowSOM's ability to detect the causal association is adversely affected when the simulation departs from multivariate normality or when the simulated data contains 50 true clusters and batch effects and/or nuisance variables, even when FlowSOM is provided with the true number of clusters as a tuning parameter. This study confirms the empirical finding that FAUST is able to robustly detect signals in data that are not found by other discovery methods.

FAUST Methodology

FAUST assumes the following criteria are met in a cytometry experiment consisting of n experimental units $E_i$, $1 \leq i \leq n$.

Assumption 1. Each Sample in the Cytometry Experiment has been Pre-Gated to Remove Debris and Dead Cells.

If pre-gating has not been performed by an investigator, computational methods can be used before applying FAUST to cytometry data in order to guarantee this assumption is met.

Assumption 2. In Each Sample, Measurements on the Live Cells are Made Using a Common Set of p Transformed Protein Markers.

Let $n_i$ denote the number of events in the $i^{th}$ experimental unit. FAUST supposes each event $E_{i,j}$ in an experimental unit $E_i$, of dimension p (the number of markers), arises as a sample from a finite mixture model $$E_{i,j} \sim \sum_{m=1}^{M} \omega_m f_{m,i}(x), \quad (4.1)$$

for $1 \le j \le n_i$, with $M \in \mathbb{N}$, $0 \le \omega_m \le 1$ and $\sum_{m=1}^{M} \omega_m = 1$ for all $1 \le i \le n$. FAUST assumes the mixture components $f_{m,i}$ of an experimental unit in (4.1) belong to the class of densities on the space of protein measurements $$\mathcal{F}_i \equiv \{f_{m,i} \mid \exists \lambda_{m,i} \in \mathbb{R}, \quad (4.2)$$

$$\sigma_{m,i} \in \mathbb{R} \text{ such that } \frac{f_{m,i} + \lambda_{m,i}}{\sigma_{m,i}} \in \mathcal{F} \, \forall \, 1 \le m \le M \}$$

for each experimental unit i, with the common class F is defined as $$\mathcal{F} \equiv \{f_m | f \text{ is unimodal along all margins}\}. \quad (4.3)$$

(4.2) expresses the fundamental modeling assumption: each mixture (4.1) that generates an experimental unit consists of a common set of densities (4.3), with unit-specific changes to location (the translations $\lambda_{m,i}$) and scale (the scalar multiples $\sigma_{m,i}$) of the component densities. These unit-specific modifications represent technical and biological effects. FAUST only assumes marginal unimodality for the f in (4.3), but makes no assumptions about the joint-distribution of these densities.

FAUST Method: Schematic Overview

FAUST is designed to perform independent approximate modal clustering of each mixture in each experimental unit. Its approximation strategy is to use 1-dimensional densities to grow an exhaustive forest of gating strategies, from which it estimates a standardized set of annotation boundaries for all markers in a mixture, which exhibit 1-dimensional multimodality either marginally or across a large number of conditional 1-dimensional density estimates. Annotation boundaries are estimated by taking a weighted average of marginal and conditional 1-dimensional antimodes for a marker that FAUST selects, using a score that quantifies if the marker has persistent multimodality in the experimental unit. FAUST also uses the distribution of the depth score across units to select a subset of markers to use for cluster discovery and annotation.

FAUST defines a cluster as a subset of events in an experimental unit that fall inside either a conical or hyper-rectangular region bounded by the Cartesian product of the standardized set of annotation boundaries. FAUST discovers cluster phenotypes by growing a random forest of partition trees for each experimental unit (following a strategy related to growing the annotation forest), and locating a sub-collection of homogeneous leaf nodes in the forest relative to the standardized phenotypic boundaries. FAUST collects a list of phenotypes discovered in each experimental unit and counts how often each phenotype appears across the set of lists. If a phenotype exceeds a user-specified filtering threshold, FAUST will annotate that cluster in each experimental unit relative to the standardized annotation boundaries. Intuitively, an annotation is a pointer to a modal regions of each experimental unit's mixture distribution. FAUST concludes by deriving a count matrix, with each row corresponding to a sample in the experiment, each column an annotated cluster, and each entry the cell count corresponding the annotated cluster in the sample.

1.1 FAUST Method: Growing the Annotation Forest

For all markers in a sample, all cells for each marker are tested for unimodality using the dip test (John A Hartigan and P M Hartigan. The Dip Test of Unimodality. The Annals of Statistics, pages 70-84, 1985). The hypothesis of unimodality is rejected for any marker that has dip test p-values below 0.25. All markers which are deemed multimodal according to this dip criterion are then used to start gating strategies. Gate locations for each strategy are determined using the taut string density estimator (P Laurie Davies and Arne Kovac. Densities, spectral densities and modality. The Annals of Statistics, 32(3):1093-1136, 2004). The location of each gate is the mid-point of any anti-modal component of the taut string. Since the taut string makes no assumptions about the number of modes present in a density, in principle this approach can lead to estimating an arbitrary number of gates in a given strategy. In practice, FAUST only pursues strategies containing 4 or fewer gates under the assumption that marker expression of 5 expression categories does not reflect biological signal. Once the initial set of gates are computed for a given marker, events are divided into sub-collections relative to the gates for that marker and the procedure recurses and repeats along each sub-collection. Algorithm 1 gives an overview of the procedure. A gating strategy terminates when it meets any of the following stopping conditions. First, once a strategy involves any three combinations of markers, it terminates. This is because the space of gating strategies grows factorially with the number of markers. Due to this growth rate, nodes in the forest are penalized factorially relative to their depth in the gating strategy when FAUST subsequently computes the depth score. Second, if at any point in a strategy FAUST fails to reject the null hypothesis of unimodality for all tested markers, the strategy terminates regardless of depth. Finally, a gating strategy terminates along a branch if all nodes along the branch contain 25 or fewer cells.

Algorithm 1 Grow Annotation Forest

```
1:    function growAnnotationForest(currentCells, currentDepth, activeMarkers)
2:        if (length(currentCells) < 25) or (currentDepth > 3) then
3:            return strategy         ▷ Gating strategy stops due to depth, event constraints.
4:        else
```

| Algorithm 1 Grow Annotation Forest |
| --- |
| 5:   currentDepth ← currentDepth + 1
6:   multimodalList ← empty list
7:   for markerIndex ∈ (columns(expressionMatrix) activeMarkers) do
8:     if pValue(dipTest(expressionMatrix[currentCells,markerIndex])) < 0.25 then
9:       append(multimodalList, markerIndex)
10:  if length(multimodalList) = = 0 then
11:    return strategy            1> Gating strategy stops due to shape constraint.
12:  else
13:    for markerIndex in multimodalList do
14:      boundaryList ← empty list
15:      Compute taut string density estimate of expressionMatrix[currentCells,markerIndex]
16:      boundaryList ← mid-points of antimodal components of taut string
17:      remainingMarkers ← activeMarkers markerIndex
18:      for i in [1,length(boundaryList)] do
19:        lg ← boundaryList[(i−1)]
20:        ug ← boundaryList[i]
21:        newCells ← rows of expressionMatrix[currentCells,markerIndex] between lg and ug
22:        growAnnotationForest(newCells, currentDepth,remainingMarkers) |

FAUST Method: Depth Score Computation

Suppose there are p>1 active markers in a sample. To compute the depth score for any of the p markers, the annotation forest is first examined to determine the following quantities: $d_1$, the number of times different markers are gated in the root population; $d_2$, the number of times children of the root are gated; and $d_3$ the number of times grandchildren of the root are gated. For $i \in \{1,2,3\}$ define $$\delta_i = \frac{1}{d_i}.$$

For $1 \le m \le p$, let $$\mathcal{N}_m \equiv \{N_{m,1}, N_{m,2}, \ldots, N_{m,n}\}.$$

be the set of all n parent nodes in the annotation forest for which the null hypothesis of unimodality is rejected for marker m. For a parent node $1 \le j \le n$, let $1_R$ denote the indicator function that is 1 when $N_{m,j}$ is the root population. Similarly, let $1_C$ denotes an indicator of a child of the root, and $1_G$ a grandchild of the root. Define the scoring function $$Q(N_{m,j}) \equiv (1-\alpha_R)1_R(N_{m,j}) + (1-\alpha_R)(1-\alpha_C)1_C(N_{m,j}) + (1-\alpha_R)(1-\alpha_C)(1-\alpha_G)1_G(N_{m,j}),$$

defining $\alpha_R = \alpha_R(N_{m,j})$ = the dip test p-value in the root population of the gating strategy that led to $N_{m,j}$.

Define $\alpha_C$ and $\alpha_G$ similarly. The function Q can be interpreted as a measure of the quality of the gating strategy that led to node $N_{m,j}$. In the case of a grandchild node that had clear modal separation along all markers in the strategy, $Q(N_{m,j}) \approx 1$, while a grandchild node that had p-values of 0.25 at each ancestral node, $Q(N_{m,j}) \approx 27/64 = 0.75^3$.

Let $P_m$ be the population size for marker m in the root population. Next define $$P(N_{m,j}) \equiv \frac{\text{\# of cells in node } N_{m,j}}{\mathcal{P}_m}.$$

Finally, define $$D(N_{m,j}) \equiv \delta_1 \cdot 1_R(N_{m,j}) + \delta_2 \cdot 1_C(N_{m,j}) + \delta_3 \cdot 1_G(N_{m,j}).$$

The depth score is defined to be the normalized sum $$DS(\mathcal{N}_m) \equiv \frac{\sum_{i=1}^{n} Q(N_{m,i}) \cdot P(N_{m,i}) \cdot D(N_{m,i})}{\max_{1 \le q \le p} DS(N_q)} \equiv \frac{\sum_{i=1}^{n} \omega(N_{m,i})}{\max_{1 \le q \le p} DS(N_q)}. \quad (4.4.)$$

The depth score maps $\mathcal{N}_m$ into [0,1] with at least one marker in a gated sample achieving the maximal score of 1.

This is taken as a measure of separation quality: the best scoring marker according to the depth score is taken to be the best separated marker in that sample at the root population, and conditionally along all other gating strategies. Normalizing to the unit interval allows depth scores to be compared across experimental units for given markers. By using the factorial weights $\delta_i$, the depth score also explains why FAUST only explores gating strategies involving, at most, combinations of three markers in its scoring and marker selection phase. Adding more combinations of markers induces a factorial increase in computational cost. But any marker that enters a gating strategy at depth 4 (or beyond) will be dominated in depth score by those markers initially gated in the annotation forest at or near the root population. Consequently, after normalization in experiments with a large number of markers, such markers have depth score an above zero, and are effectively never selected by FAUST for discovery and annotation. Hence the restriction to 3-marker gating strategies.

FAUST Method: Phenotypic Boundary Estimation

The depth score is also used to estimate annotation boundaries. Recalling FAUST only explores gating strategies with 4 or fewer annotation boundaries, FAUST partitions the set $$\mathcal{N}_m = \mathcal{G}_1 \cup \mathcal{G}_2 \cup \mathcal{G}_3 \cup \mathcal{G}_4.$$

Define $\mathcal{G}_1 = \{N_{m,i} \in \mathcal{N}_m | N_{m,i}$ has a single gate determined by the taut string$\}$.

Define $\mathcal{G}_2$, $\mathcal{G}_3$, and $\mathcal{G}_4$ similarly. In other words, each $\mathcal{G}_i$ is the subset of nodes in the annotation forest for marker m with i gates. Recalling (4.4), the score can be partitioned as $$\sum_{i=1}^{n} \omega(N_{m,i}) = \sum_{j=1}^{4} \sum_{N \in \mathcal{G}_j} \omega(N).$$

FAUST selects the number of annotation boundaries for the marker m by choosing the set $\mathcal{G}_j$ with the maximal sum $$\sum_{N \in \mathcal{G}_j} \omega(N)$$

Letting $g_1(N_{m,j})$ denote the smallest gate location estimated by the taut string in node $N_{m,j}$ (which is the only gate location if FAUST selects $\mathcal{G}_1$), FAUST estimates the phenotypic boundary locations for the marker by taking the weighted average $$\frac{\sum_{N \in \mathcal{G}_j} \omega(N) g_1(N)}{\sum_{N \in \mathcal{G}_j} \omega(N)}$$

In the event FAUST selects $\mathcal{G}_j$, $j>1$ (i.e., multiple annotation boundaries), similar weighted averages are taken for $g_2(N_{m,j})$, etc.

FAUST Method: Marker Selection

Markers are selected by comparing the user-selected, empirical depth score quantile across experimental units to a user-selected threshold value. All markers whose empirical quantile exceeds the threshold are used for discovery and annotation.

FAUST Method: Boundary Standardization

FAUST standardizes the number of annotation boundaries for each marker by majority vote. The most frequently occurring number of annotation boundaries across experimental units is chosen as the standard number. This behavior can be over-ridden via the preference list tuning parameter in order to incorporate prior biological information into FAUST. Next, for a given marker, FAUST selects the set of samples where the number of annotation boundaries for that marker matches the standard. Then, by rank, FAUST computes the median absolute deviation of the location of each phenotypic boundary across experimental units. In the following, the median boundary locations are referred to as the standard boundaries. FAUST enforces standardization of annotation boundaries for non-conforming experimental units by imputation or deletion. Imputation in an experimental unit occurs when FAUST estimates fewer boundaries than the standard. In this case, each boundary in the non-conforming unit is matched to one of the standards by distance. Unmatched standards are used to impute the missing boundaries. Similar distance computations are done in the case of deletion, but FAUST deletes boundaries that are farthest from the standards. For both imputation and deletion, if multiple boundaries match the same standard, then the boundary minimizing the distance is kept, and the other boundaries are deleted. Should this result in standards that don't map to any boundaries, then those unmatched standards are used to impute the missing boundaries.

FAUST Method: Phenotype Discovery and Cluster Annotation

For each experimental unit, FAUST constructs a forest of partition trees (randomly sampled) and annotates selected leaves from this forest relative to the standardized annotation boundaries. Partition tree construction is similar to tree construction for the annotation forest, but they are not depth-constrained: a tree continues to grow following the previously described strategy until each leaf is unimodal according to the dip test (John A Hartigan and P M Hartigan. The Dip Test of Unimodality. The Annals of Statistics, pages 70-84, 1985) or contains fewer than 25 cells. Consequently, a single partition tree defines a clustering of an experimental unit. Clusterings from the forest of partition trees are combined into a single clustering in the following manner. To ensure cells are not assigned to multiple clusters, a subset of leaves of the partition forest are selected by scoring leaves according to shape criteria, and then selecting a subset of leaves across partition trees that share no cells to maximize their total shape score. Only the selected leaves are given phenotypic annotations. FAUST keeps a list of discovered phenotypes for each experimental unit, and concludes by returning exact counts of cells in each sample whose phenotypes exceed a user-specified occurrence frequency threshold. Details of the scoring and selection procedure are described in Greene et al. (Selective clustering annotated using modes of projections. arXiv preprint arXiv: 1807.10328, 2018, which is hereby incorporated by reference in its entirety).

FAUST Method: Tuning Parameters 1.1.1 Starting Cell Population

The name of the population in the manual gating strategy where FAUST conducts discovery and annotation.

1.1.2 Active Markers

A list of all markers in the experiment that can possibly be used for discovery and annotation in the starting cell population. FAUST will only compute the depth score for markers in this initial set.

1.1.3 Marker Boundary Matrix

A 2×n matrix of lower and upper protein expression bounds. By default, it is set for inf and inf for all markers in a flow experiment. When the manual gating strategy does not remove all debris or doublets from the starting cell population, samples can appear to have clusters of events along at very low or very high expression values for some markers. By setting boundaries for those markers to exclude these doublet or debris clusters, FAUST treats all events below the lower and above the upper bounds as default low or high, respectively. These events are not dropped from the experiment. However, they are ignored when testing for multimodality and subsequent density estimation. In the case of mass cytometry experiments, the default lower boundary is set to 0 for all markers in an experiment in order to accommodate the zero-inflation common to mass cytometry data. The number of events in a marker that fall between the lower and upper marker boundaries in the starting cell population define the effective sample size for that marker.

1.1.4 Depth-Score Selection Quantile

The empirical quantile of a marker's depth-score across all experimental units that is used to compare against a user-selected depth-score threshold. By default, this parameter is set to the median.

1.1.5 Depth-Score Selection Threshold

A value in [0, 1] used to select a subset of markers to be used in discovery and annotation based on their empirical depth score selection quantile. By default, this parameter is set to 0.01.

1.1.6 Supervised Boundary Estimation List

Allows the user to modify FAUST's default gate standardization methodology for each marker. This parameter is one way to incorporate prior (biological) knowledge in the FAUST procedure: if a marker is known to have a certain range of expression, such as low-dim-bright, this can be used to encourage or force FAUST to estimate the corresponding number of annotation boundaries from the data. Similarly, if FMO controls have been collected for a marker, this parameter can be used to set the phenotypic boundary according to the controls.

1.1.7 Phenotype Occurrence Threshold

An integer value used to include or exclude discovered phenotypes in the final count matrix returned by FAUST. If a phenotype appears at least Phenotype Occurrence Threshold times across experimental units, it is included in the final counts matrix. By default, all discovered phenotypes are included. Phenotypes exceeding the threshold are assumed to be biological signal while those that fall below it are assumed to be sample- or batch-specific effects. A consequence of this assumption is that all cells in a sample associated with any phenotype falling below the threshold are re-annotated with a common non-informative label indicating those phenotypes ought not be analyzed due to their rarity.

1.2 CITN-09 T Cell Panel Analysis

FAUST was applied to samples generated in this study. Between one and four samples were collected from 27 patients with stage IV and unresectable stage IIIB Merkel Cell Carcinoma (Nghiem et al., Durable tumor regression and overall survival in patients with advanced merkel cell carcinoma receiving pembrolizumab as first-line therapy. Journal of Clinical Oncology, 37(9):693-702, 2019. PMID: 30726175); Nghiem et al., New England Journal of Medicine, 374(26):2542-2552, 2016. PMID: 27093365) and spanning the course of treatment. All 27 patients had samples collected at baseline (cycle C01, before initiation of anti-PD-1 therapy); 16 at cycle C02 (3 weeks post-treatment of the second cycle of therapy); 22 at cycle C05 (12 weeks post-treatment of the fifth cycle of therapy); and 13 at end of trial (EOT, patient specific). 18 of 27 subjects responded to therapy for an observed response rate of 67%. Each sample was pre-gated to remove debris and identify live lymphocytes. The manual gating strategy is displayed herein:

Let $c_{i,k}$ denote the number of events in FAUST cluster k for sample i. Let $n_i$ denote the number of events in the $i^{th}$ subject's baseline sample. Similar to Nowicka et al., (Cytof workflow: differential discovery in high-throughput high-dimensional cytometry datasets. F1000Research, 6, 2017), it is assumed that $c_{i,k} \sim \text{Binomial}(n_i, \mu_{i,k})$. The model is $$\text{logit}^{-1}(\mu_{i,k}) = \beta_0 + \beta_1 \cdot \text{Responder} + \xi_{i,k}, \quad (4.5)$$

where Responder is an indicator variable equal to 1 when the subject exhibits complete or partial response to therapy, and 0 otherwise, and each $\xi_{i,k} \sim N(0, \sigma_{i,k}^2)$ is a subject-level random effect.

The R package lme4 was used to fit all GLMMs (Bates et al., Fitting linear mixed-effects models using lme4. arXiv preprint arXiv:1406.5823, 2014).

1.3 CITN-09 Myeloid Panel

Figure 16:
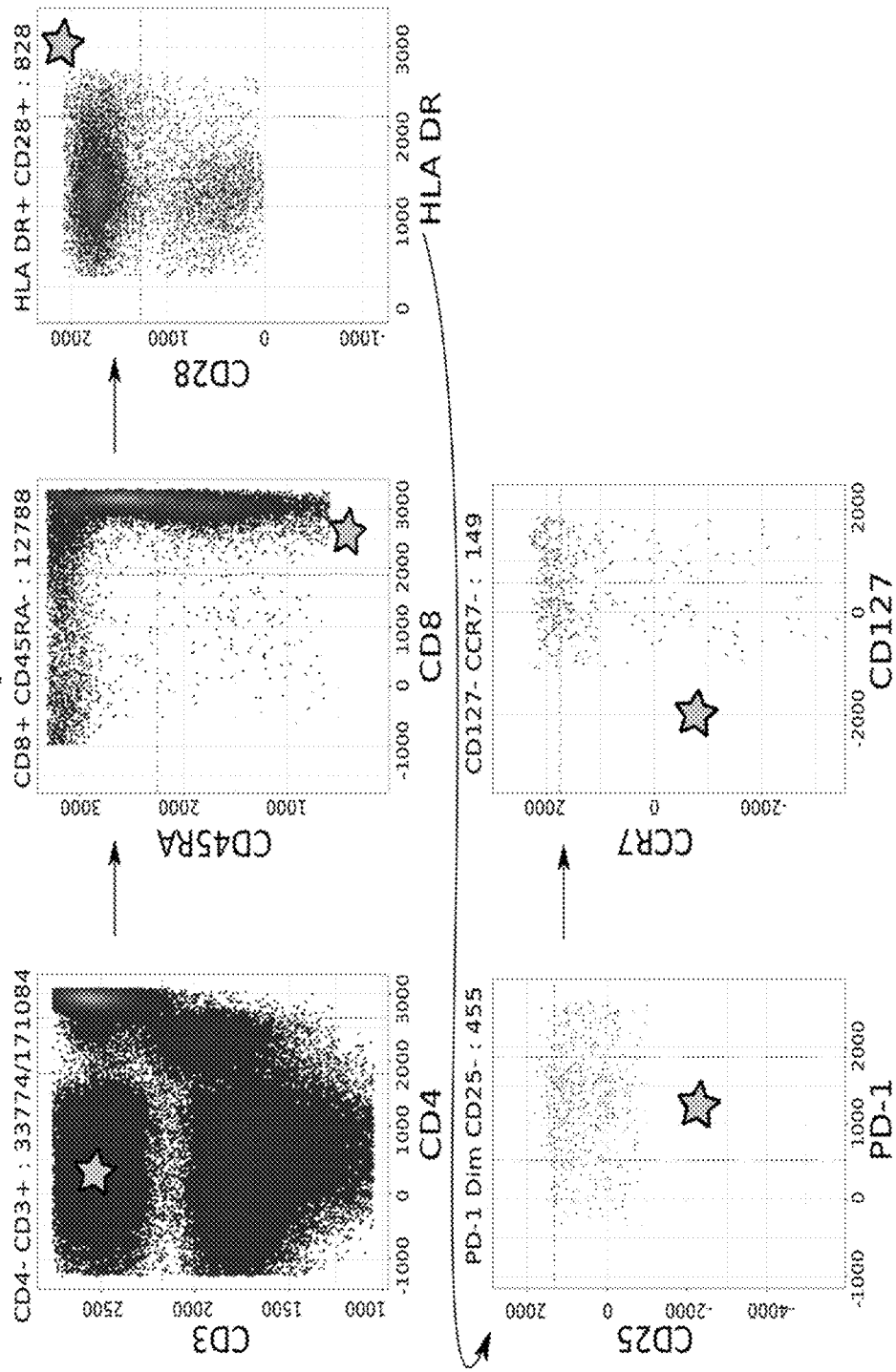
FIG. 16 provides an exemplary gating strategy for CD4− CD3+ CD8+ CD45RA− HLA-DR+ CD28+ PD-1 dim CD25− CD127− CCR7− in two baseline samples from CITN-09.
Figure 16:
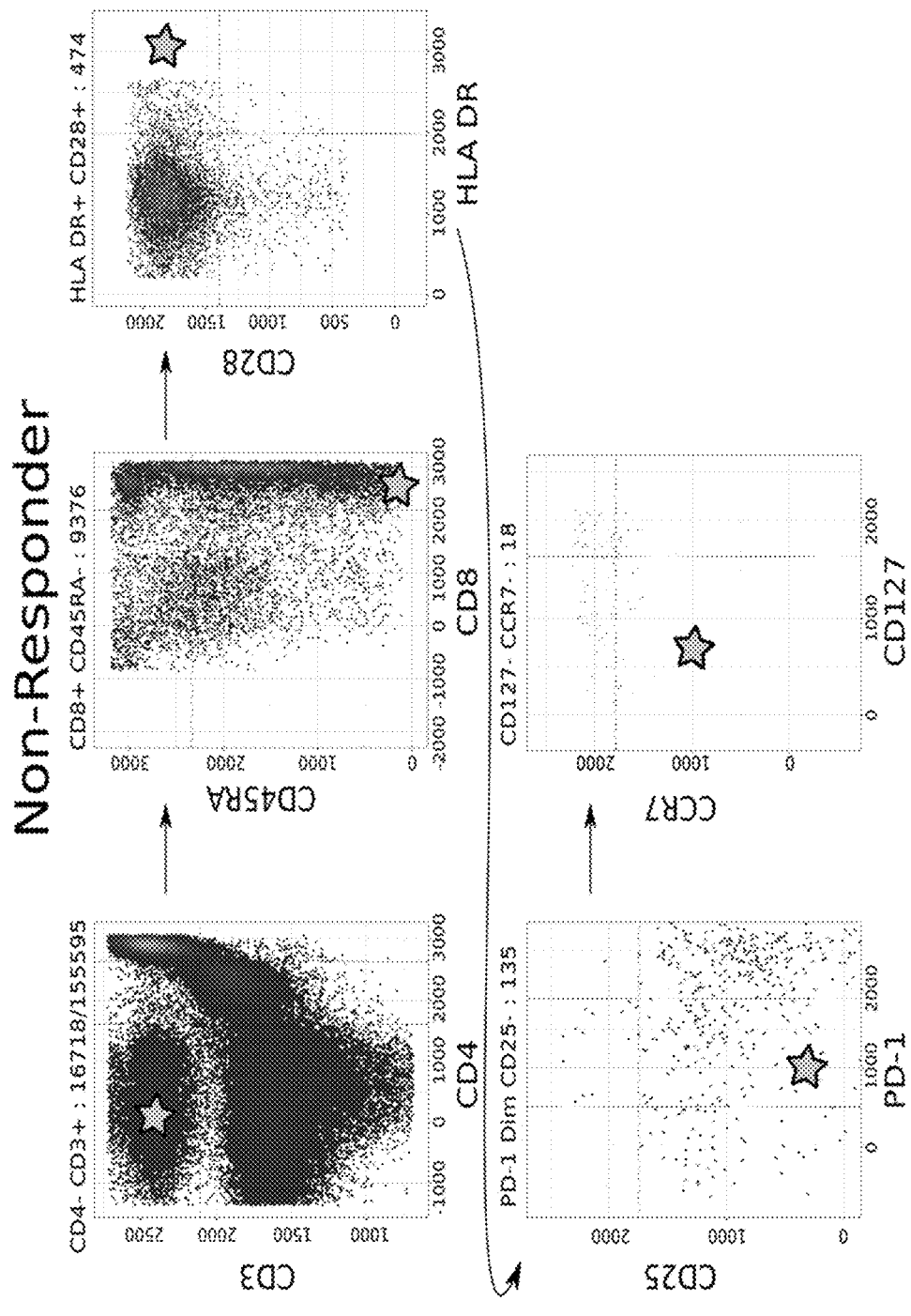

This data set consisted of 69 samples stained to investigate myeloid cells. An initial screen comparing the ratio of the number of events in the singlet gate to the number of events in the root population led us to remove 14 samples from analysis due to low quality. FAUST was applied to remaining 55 samples which consisted of 16 samples collected at cycle C01, before initiation of anti-PD-1 therapy; 15 at cycle C02; 15 at cycle C05; and 9 at EOT. Discovery and annotation was run at the individual sample level using cells in the "45+" node of the manual gating strategy. FIG. 16 provides an exemplary gating strategy for CD4− CD3+ CD8+ CD45RA− HLA-DR+ CD28+ PD-1 dim CD25− CD127− CCR7− in two baseline samples from CITN-09. FAUST selected 11 markers: CD33, CD16, CD15, HLA-DR, CD14, CD3, CD11B, CD20, CD19, CD56, CD11C.

CITN-07 Phenotyping Panel Analysis

Figure 19:
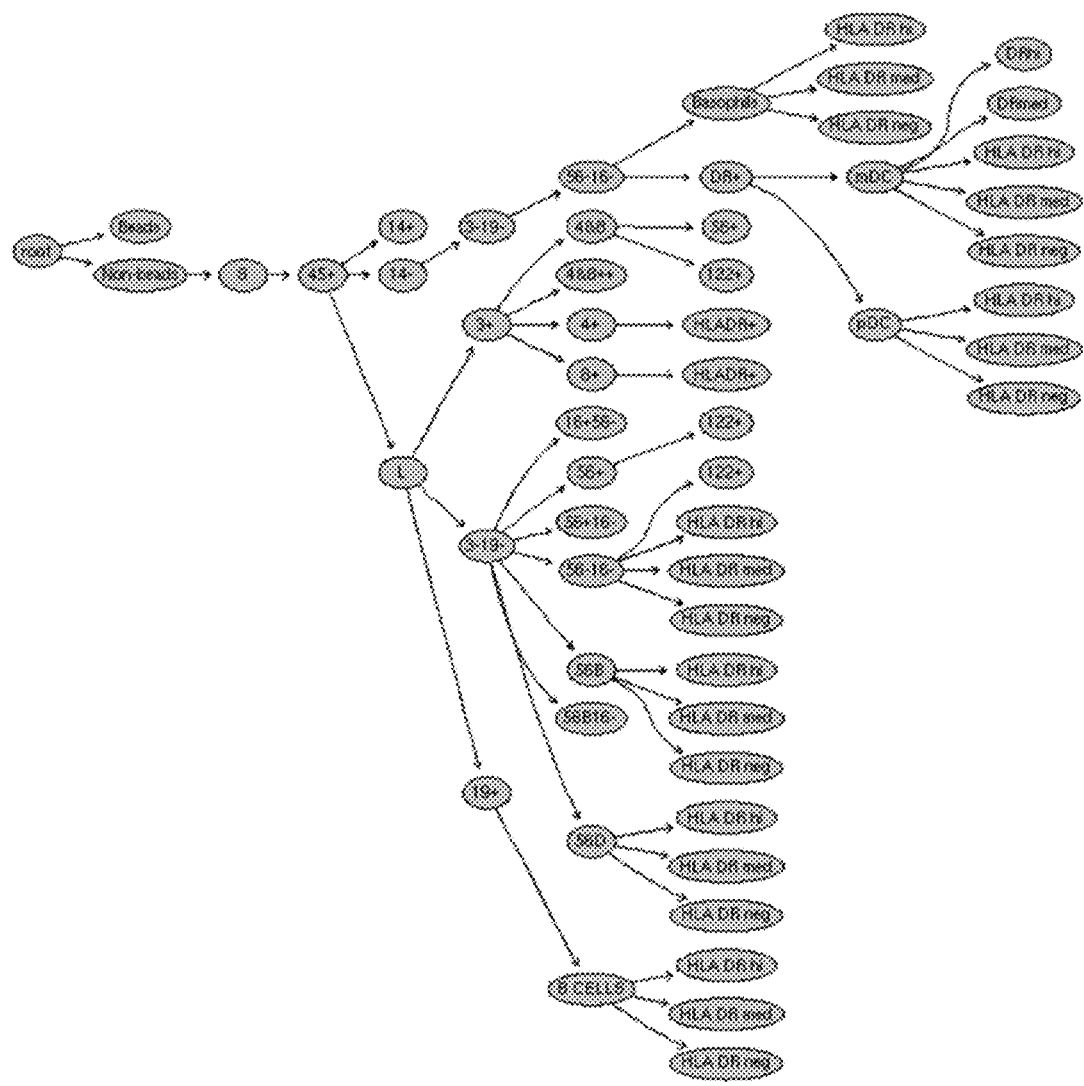
FIG. 19 provides a visualization of the manual gating strategy used in initial analysis of CITN-07 Phenotyping staining panel.

FAUST was applied to this data set comprising of a total of 358 longitudinal samples from 35 subjects in two cohorts (Cohort 1: with FLT-3 pre-treatment and Cohort 2: without pre-treatment), with between 4 and 12 samples per subject over four cycles of therapy and at end of trial. Subjects were given FLT-3 ligand seven days prior to the start of the first two of four treatment cycles. FLT-3 ligand was given to promote the expansion of myeloid and dendritic cell compartments in order to investigate whether expansion improved response to therapy. FAUST was configured to perform cell population discovery and annotation per sample in order to account for biological and technical heterogeneity. Debris, dead cells and non-lymphocytes were excluded by pre-gating (FIG. 19). Each cell populations discovered by FAUST was tested at the cohort-specific baseline for association with recurrence of disease (14 subjects had disease recur, 18 did not have disease recur). Similar to model (4.5), here the model adjusted for subject-to-subject variability using a random effect. Cohort status, recurrence, and NYESO-1 staining of the tumor by immunohistochemistry (measured as positive, negative, or undetermined) were modeled as population effects.

1.4 Analysis of CyTOF Data Published by Krieg et al.

FAUST was used to discover and annotate cell populations in the mass cytometry data sets stained to investigate myeloid cells as reported by Krieg et al. (High-dimensional single-cell analysis predicts response to anti-pd-1 immunotherapy. Nature medicine, 24(2):144, 2018). Following Krieg et al., samples with fewer than 50 cells were removed from the analysis. To account for batch effects and small sample sizes, all samples within a batch were concatenated and processed by FAUST. FAUST selected 11 markers for discovery and annotation: CD16, CD14, CD11b, CD11c, CD33, ICAM1, CD62L, PD-L1, CD7, CD56, and HLA-DR. The baseline model was similar to (4.5), but was modified by $$\text{logit}^{-1}(\mu_{i,k}) \beta_0 + \beta_1 \cdot \text{Responder} + \xi_{i,k} + \eta_{i,j},$$

where $j \in \{1, 2\}$, and $\eta_{i,j} \sim N(0, \sigma_j^2)$ is a random effect included to model the batch effects.

1.5 Analysis of FACS Data Published by Krieg et al.

Figure 15:
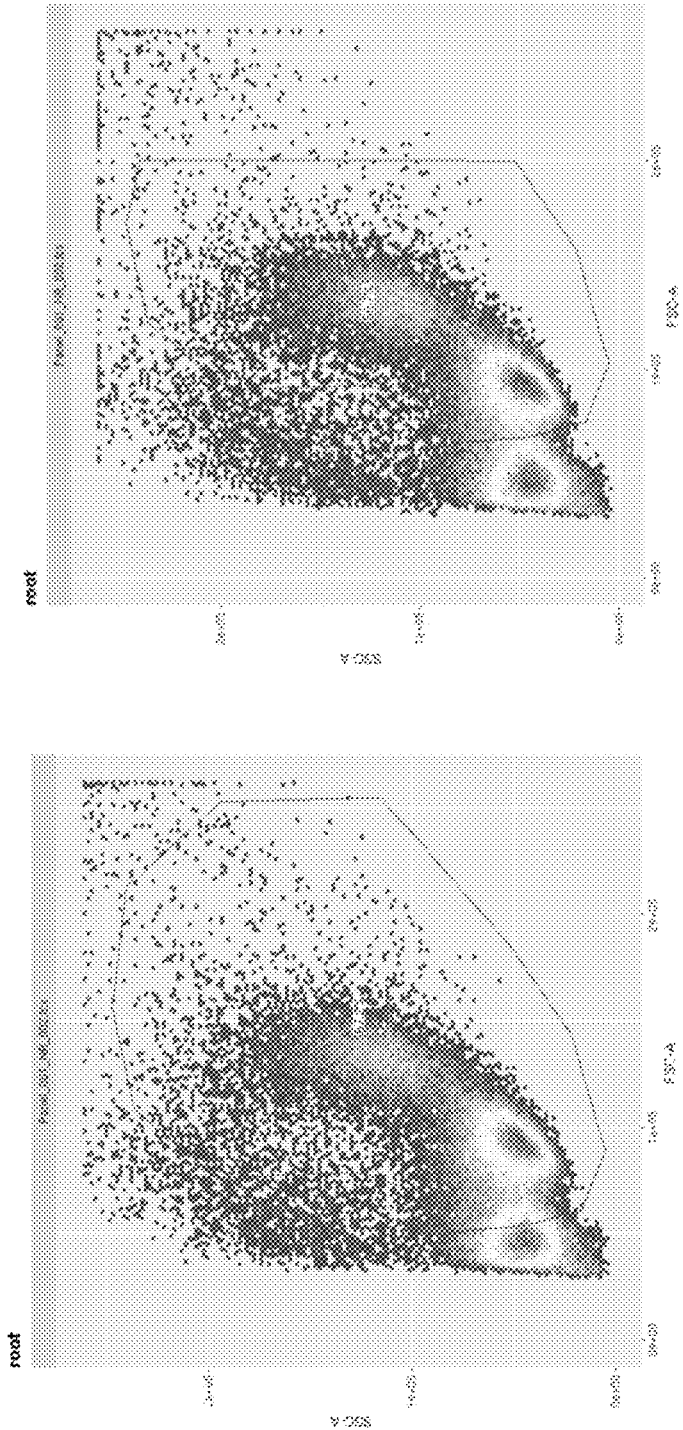
FIGS. 15A and 15B provide an example of modification to the manual gating strategy of the Krieg et al. FACS data.

FAUST processed 31 flow cytometry samples from responders and non-responders to therapy. FAUST was run at the individual sample level on live cells from the manual gating strategy used by Krieg et al. QC and review of the manual gating strategy let one make manual adjustments to the "Lymphocytes" gate of 7 samples in this data set. An example of this gate adjustment is shown in which FAUST selected 9 markers for discovery and annotation: CD3, CD4, HLA-DR, CD19, CD14, CD11b, CD56, CD16, and CD45RO. The statistical model used here is identical to (4.5), with $c_{i,k}$ now denoting the 40 clusters in the FACS data, and $n_i$ refers to the baseline FACS sample counts. FIGS. 15A and 15B provide an example of modification to the manual gating strategy of the Krieg et al. FACS data.

1.6 Compartment Multivariate Analysis

All FAUST clusters annotated as CD3−, CD56−, and CD19− and included in the univariate analysis were included in the multivariate analysis. Within this set, subpopulations annotated as HLA-DR− were further excluded. This defined the Myeloid compartment for CITN-07, CITN-09, and the Krieg et al. FACS data. Let k* denote the number of FAUST clusters within a given study. Let n denote the number of subjects at baseline, and $N = n \cdot k^*$. For $1 \le i \le N$, $1 \le j \le k^*$ the statistical model is $$\text{logit}^{-1}(\mu_{i,j}) = \beta_0 + \beta_R \cdot \text{Responder}_i + \Sigma_{j=1}^{k^*}{}_1(\beta_{c,j} \cdot \text{Cluster}_{i,j} + \beta_{i,j} \cdot \text{Cluster}_{i,j} \cdot \text{Responder}_i) + \eta_i, \quad (4.6)$$

where $\text{Cluster}_{i,j}$ is an indicator variable that is 1 when observation i is from cluster j and 0 otherwise, $\text{Responder}_i$ is an indicator variable when observation i is taken from a responding subject, and $\eta_i \sim N(0, \sigma_i^2)^i$ is an observation-level random effect. To test for differential abundance across a compartment, linear combination of the coefficients $\beta_{i,j}$ in (4.6) are tested for positivity. For example, the test for differential abundance across an entire compartment is specified $$H_0 : \beta_R + \frac{1}{k^*} \cdot \sum_{j=1}^{k^*} \beta_{i,j} \le 0,$$

$$H_1 : \beta_R + \frac{1}{k^*} \cdot \sum_{j=1}^{k^*} \beta_{i,j} > 0.$$

1.7 Compartment Aggregate Analysis

For the aggregate analysis, compartment definitions are the same as presented in section 4.15. Counts are derived by summing across FAUST clusters within each compartment. The model (4.5) is then used to test each derived compartment for differential abundance.

| A1 Effect Sizes and Confidence Intervals in CITN-09 | | | |
|---|---|---|---|
| Population | Effect Size | Lower 2.5% | Upper 97.5% |
| CD4− CD3+ CD8+ CD45RA− HLA-DR+ CD28+ PD-1+ CD25− CD127− CCR7− | 1.844 | 0.784 | 2.955 |
| CD4− CD3+ CD8+ CD45RA− HLA-DR+ CD28+ PD-1 dim CD25− CD127− CCR7− | 1.896 | 0.898 | 2.981 |
| CD4 bright CD3+ CD8− CD45RA− HLA-DR− CD28+ PD-1 dim CD25− CD127− CCR7− | 1.907 | 0.929 | 2.941 |
| CD4 bright CD3+ CD8− CD45RA+ HLA-DR− CD28− PD-1 dim CD25− CD127+ CCR7+ | 2.999 | 1.387 | 4.837 |

| A2 Alternative analysis of CITN-09 T cell panel | | | | | |
|---|---|---|---|---|---|
| Method | Num Clusters | Transformation | Input Data | Best FDR | Second FDR |
| DensityCut | 2599 | Biexp | Baseline | 0.09 | 1.00 |
| DensityCut | 2570 | Asinh | Baseline | 0.83 | 0.83 |
| DensityCut | 6389 | Biexp | All | 0.00 | 0.22 |
| DensityCut | 6166 | Asinh | All | 0.00 | 1.00 |
| FlowSOM | 100 | Asinh | Baseline | 0.62 | 0.62 |
| FlowSOM | 400 | Asinh | Baseline | 0.53 | 0.53 |
| FlowSOM | 100 | Biexp | Baseline | 0.49 | 0.71 |
| FlowSOM | 400 | Biexp | Baseline | 0.58 | 0.58 |
| FlowSOM | 100 | Asinh | All | 0.64 | 0.64 |
| FlowSOM | 400 | Asinh | All | 0.43 | 0.43 |
| FlowSOM | 100 | Biexp | All | 0.65 | 0.65 |
| FlowSOM | 400 | Biexp | All | 0.29 | 0.29 |
| Phenograph | 46 | Asinh | Baseline | 0.35 | 0.35 |
| Phenograph | 45 | Biexp | Baseline | 0.36 | 0.36 |
| Phenograph | 47 | Asinh | All | 0.31 | 0.31 |
| Phenograph | 49 | Biexp | All | 0.34 | 0.34 |
| FAUST | 267 | Biexp | Baseline | 0.03 | 0.03 |
| FAUST | 290 | Asinh | Baseline | 0.00 | 0.02 |
| FAUST | 238 | Biexp | All | 0.02 | 0.02 |
| FAUST | 239 | Asinh | All | 0.00 | 0.00 |

Table 3: Results of applying the clustering methods DensityCut, FAUST, FlowSOM, and Phenograph to flow cytometry data stained to investigate T cell activity from the MCC anti-PD-1 trial.
Tuning parameters for FlowSOM and Phenograph (including the number of clusters for FlowSOM) were set.
The supporting table "cytoa23030-sup-0001-suppinfo.xlsx" reports that Phenograph is run with k = 30 neighbors and using the Euclidean metric.
"FlowSOM pre" is reported as running with 100 and 400 clusters with "transform = FALSE" and "scale = FALSE".
Flow cytometry data are reported as being transformed by the hyperbolic arcsine transformation with cofactor 120.
Data is transformed using both the biexponential transformation (used by CITN on the "Biexp" rows) as well as the hyperbolic arcsine with cofactor 120 (The "Asinh" rows).
DensityCut was run totally unsupervised: the K parameter is set to its default value $\log_2(N)$.
Samples were concatenated before analysis by each method except FAUST, which was run at the sample level for all analyses.
Rows with "Input data" listing "Baseline" only combine patient samples from the baseline time point, while that list All" have samples from all time points combined prior to analysis.
The reported FAUST number of clusters is the number of clusters with "CD3+" annotations.
The tuning parameters for FAUST in the "Asinh" runs and the baseline "Biexp" run were taken from the FAUST "Biexp" all run, which is reported in the paper.
The channel bounds matrix was transformed to the "Asinh" runs by computing the empirical quantiles of the concatenated biexponentially transformed data corresponding to the bounds reported herein, and then computing those quantiles on the transformed concatenated data.
Similarly, the baseline phenotypic filtering threshold was scaled from the setting of 5 for the 78 all sample runs to the setting of 2 for the 27 baseline sample runs.

A3 Staining Panels Used in FAUST Analyses

Figure 17:
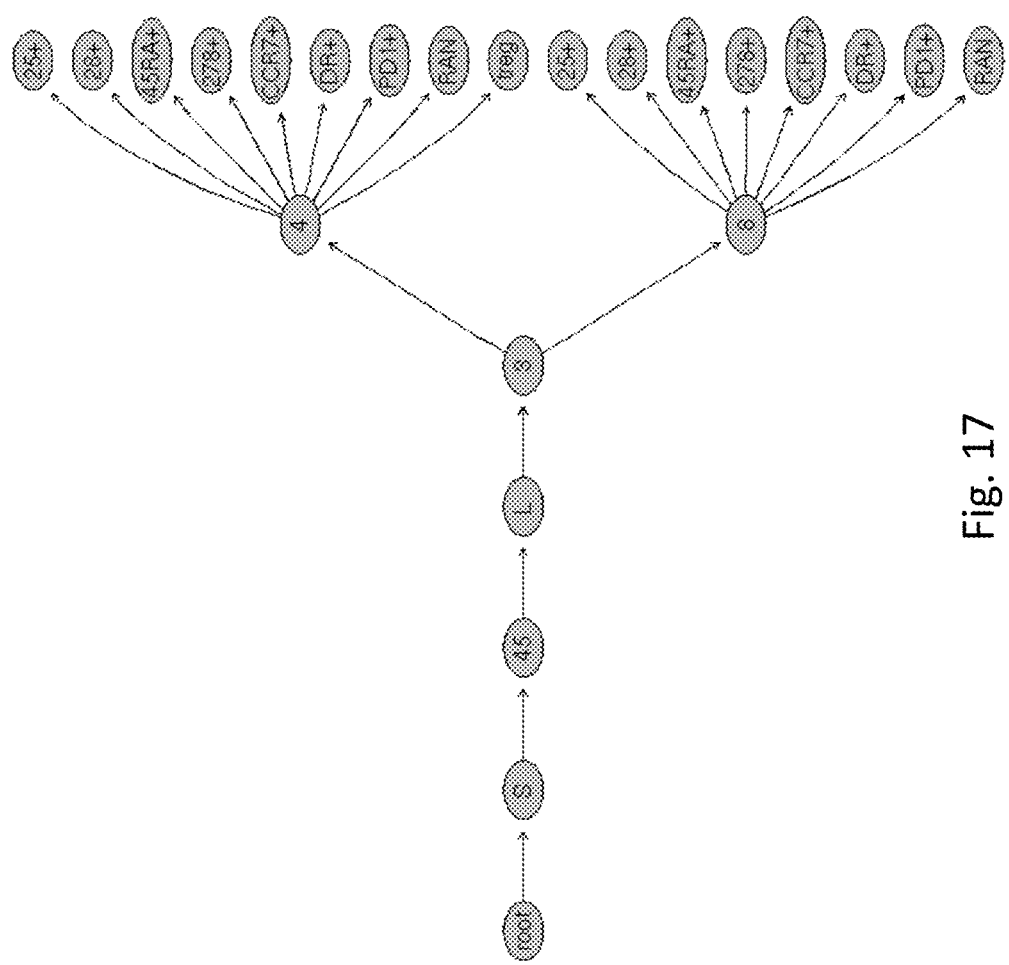
FIG. 17 provides a visualization of the manual gating strategy used in initial analysis of CITN-09 T cell staining panel.
Figure 18:
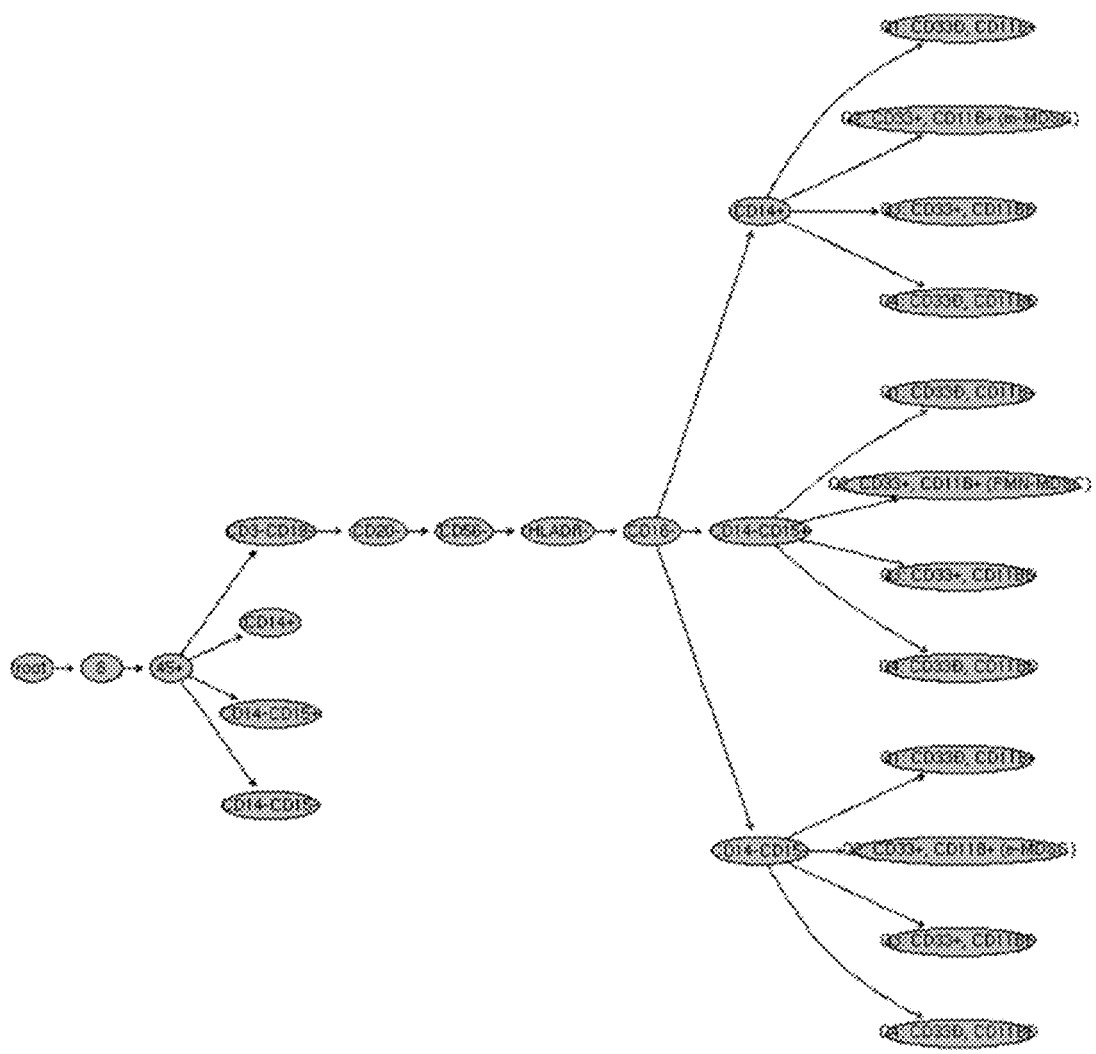
FIG. 18 provides a visualization of the manual gating strategy used in initial analysis of CITN-09 Myeloid staining panel.

Staining panels from the experiments used in FAUST analyses are provided herein, including described below. Additionally, FIGS. 17-19 provide visualization of the manual gating used in initial analysis of CITN-09 T cell staining panel, CITN-09 Myeloid staining panel and CITN-07 phenotyping staining panel.

A.3.1 CITN-09 T Cell Staining Panel

| name | desc |
|---|---|
| $P1 | FSC-A | |
| $P2 | FSC-H | |
| $P3 | SSC-A | |
| $P4 | SSC-H | |
| $P5 | <PE-A> | CD278 ICOS |
| $P6 | <FITC-A> | CD3 |
| $P7 | <BV 421-A> | CD127 |
| $P8 | <Alexa Fluor 700-A> | CD197 CCR7 |
| $P9 | <PE-Cy7-A> | CD279 PD-1 |
| $P10 | <PerCP-Cy5-5-A> | CD8 |
| $P11 | <APC-Cy7-A> | CD4 |
| $P12 | <ECD-A> | CD28 |
| $P13 | <APC-A> | CD25 |
| $P14 | PE-Cy5-A | |
| $P15 | <AmCyan-A> | CD45 |
| $P16 | <BV 605-A> | HLA DR |
| $P17 | <BV 650-A> | CD45RA |
| $P18 | Time | |

A.3.2 CITN-09 Myeloid Staining Panel

| name | desc |
|---|---|
| $P1 | FSC-A | |
| $P2 | FSC-H | |
| $P3 | SSC-A | |
| $P4 | SSC-H | |
| $P5 | <PE-A> | CD11B |
| $P6 | <FITC-A> | CD20 |
| $P7 | <BV 421-A> | CD14 |
| $P8 | <Alexa Fluor 700-A> | CD11C |
| $P9 | <PE-Cy7-A> | CD56 |
| $P10 | <PerCP-Cy5-5-A> | CD33 |
| $P11 | <APC-Cy7-A> | CD16 |
| $P12 | <ECD-A> | CD3 |
| $P13 | <APC-A> | CD15 |
| $P14 | <PE-Cy5-A> | CD19 |
| $P15 | <AmCyan-A> | CD45 |
| $P16 | <BV605-A> | HLA DR |
| $P17 | BV 650-A | |
| $P18 | Time | |

CITN-07 Phenotyping Staining Panel

| name | desc |
|---|---|
| $P1 | FSC-A | |
| $P2 | FSC-H | |
| $P3 | SSC-A | |
| $P4 | SSC-H | |
| $P5 | <PE-A> | CD123 |
| $P6 | <FITC-A> | CD4 |
| $P7 | <BV 421-A> | CD14 |
| $P8 | <Alexa Fluor 700-A> | CD11C |
| $P9 | <PE-Cy7-A> | CD56 |
| $P10 | <PerCP-Cy5-5-A> | CD8 |
| $P11 | <APC-Cy7-A> | CD16 |
| $P12 | <ECD-A> | CD3 |
| $P13 | <APC-A> | CD122 |
| $P14 | <PE-Cy5-A> | CD19 |
| $P15 | <AmCyan-A> | CD45 |
| $P16 | <BV 605-A> | HLA DR |
| $P17 | BV 650-A | |
| $P18 | Time | |

Myeloid CyTOF Panel

| name | desc |
|---|---|
| $P1 | Bi209Di | 209Bi_CD11b |
| $P2 | Dy162Di | 162Dy_CD11c |
| $P3 | Dy163Di | 163Dy_CD7 |
| $P4 | Er166Di | 166Er_CD209 |
| $P5 | Er167Di | 167Er_CD38 |
| $P6 | Eu151Di | 151Eu_CD123 |
| $P7 | Eu153Di | 153Eu_CD62L |
| $P8 | Gd152Di | 152Gd_CD66b |
| $P9 | Gd154Di | 154Gd_ICAM-1 |
| $P10 | Gd155Di | 155Gd_CD1c |
| $P11 | Gd156Di | 156Gd_CD86 |
| $P12 | Gd160Di | 160Gd_CD14 |
| $P13 | Ho165Di | 165Ho_CD16 |
| $P16 | Lu175Di | 175Lu_PD-L1 |
| $P18 | Nd146Di | 146Nd_CD64 |
| $P22 | Sm147Di | 147Sm_CD303 |
| $P23 | Sm148Di | 148Sm_CD34 |
| $P24 | Sm149Di | 149Sm_CD141 |
| $P25 | Sm150Di | 150Sm_CD61 |
| $P26 | Tm169Di | 169Tm_CD33 |
| $P27 | Y89Di | 89Y_CD45 |
| $P29 | Yb173Di | 173Yb_CD56 |
| $P30 | Yb174Di | 174Yb_HLA-DR |

FACS Panel

| name | desc |
|---|---|
| $P1 | FSC-A | |
| $P2 | FSC-H | |
| $P3 | FSC-W | |
| $P4 | SSC-A | |
| $P5 | SSC-H | |
| $P6 | SSC-W | |
| $P7 | Comp-Brilliant Violet 785-A | CD3 |
| $P8 | Comp-Brilliant Violet 711-A | CD4 |
| $P9 | Comp-Brilliant Violet 421-A | CD11b |
| $P10 | Comp-PerCP-Cy5-5-A | CD33 |
| $P11 | Comp-FITC-A | HLA-DR |
| $P12 | Comp-PE-Cy7-A | CD56 |
| $P13 | Comp-PE-Texas Red-A | CD45RO |
| $P14 | Comp-APC-Cy7-A | NIR |
| $P15 | Comp-Alexa Fluor 700-A | CD11c |
| $P16 | Comp-APC-A | CD16 |
| $P17 | Comp-PE-A | CD14 |
| $P18 | Comp-Brilliant Violet 605-A | CD19 |
| $P19 | Time | |

Simulation Study

A.1.1 Simulation Goals

The purpose of this simulation study is to assess the performance of the FAUST algorithm, both as a clustering tool and as a discovery tool, when experimental data are simulated from mixture models following the assumptions disclosed herein. The simulation measures how well FAUST recovers the underlying mixture under a variety of parametric scenarios. The simulation also measures how well FAUST is able to detect a sub-population, elevated in half the samples, that is simulated to have causal relationship with a subject's response to therapy. The performance of FAUST is compared to the performance of the flowSOM clustering algorithm (Gassen et al., Flowsom: Using self-organizing maps for visualization and interpretation of cytometry data. Cytometry Part A, 87(7):636-645, 2015).

A.1.2 Baseline Simulation Description

The basic simulation generates data from an experiment containing 100 independent samples of 10-dimensional data from a Gaussian mixture model with 10 components. A probability vector $$p \sim \text{Dirichlet}(\alpha \equiv (1,1,\ldots,1)) \quad (A.7)$$

of dimension equal to the number of mixture components is generated. In a given simulation iteration, sampling from the Dirichlet continues until all elements are greater or equal to 0.001.

There are four tuning parameters that modify this baseline setting. A complete description of how the simulation study works under default parameters is given, after which a description of how the tuning parameters modify the baseline study is given.

In the basic setting, the size of each of the 100 samples is $n_j = \max(5000, s)$, $1 \leq j \leq 100$, where $$s \sim T(\mu = 10000, \nu = 3)$$

is a sample from a non-central T distribution with 3 degrees of freedom and non-centrality parameter 10000. Each sample is meant to represent a sample taken from a subject in an immunology study and then interrogated via flow cytometry.

Before generating the samples, a fixed collection of mean vectors $$\mu_c, 1 \leq c \leq 10$$

is determined for the ten Gaussian mixture components that is used across all simulated samples. Each of the ten entries of $\mu_c$ are randomly selected from the columns of Table 4, and represent whether or not the measured variable exhibits a signal. When an entry of $\mu_c$ is from the "No Signal" row of Table 4, the corresponding variable is labeled "−". Similarly, when an entry of $\mu_c$ is from the "Signal" row of Table 4, the corresponding variable is labeled "+". In an example, the annotation "V1− V2− V3+ V4− V5+ V6− V7− V8− V9+ V10−" indicates the mean vector $\mu_c$ of the mixture component contains 0 for V1, V2, V4, V6, V7, V8, and V10, while it is 7 for V3, 6 for V5, and 4 for V9. Each mean vector is associated with an element of the probability vector (A.7). Covariance matrices $\Sigma_c$ are always constrained to have variances between 1 and 2, but otherwise are randomly generated sample by sample and component by component.

TABLE 4

Possible mean vector entries for the ten simulation variables.

| | V1 | V2 | V3 | V4 | V5 | V6 | V7 | V8 | V9 | V10 |
|---|---|---|---|---|---|---|---|---|---|---|
| No Signal | 0 | 0 | 0 | 0 | 0 | 0 | 0 | 0 | 0 | 0 |
| Signal | 8 | 8 | 7 | 7 | 6 | 6 | 5 | 5 | 4 | 4 |

Each simulation iteration, 50 of the 100 samples are randomly selected to have a mixture component elevated. Without loss of generality, suppose (A.7) is in sorted order, so that the first entry $p_1$ is the largest value, the tenth entry $p_{10}$ is the smallest value, and intermediate entries correspond to their order statistics. In the non-elevated samples, the mean-vector $\mu_c$ associated with the smallest element of the probability vector (A.7), $p_{10}$, is identified as the cluster component to elevate. In the samples randomly selected for elevation, the probability vector (A.7) is modified as follows. The numerical value $p_{target} \equiv p_7$ is fixed. Next, the intermediate probability vector $$p_{int} \equiv \left(p_1 + \frac{p_{10}}{9}, p_2 + \frac{p_{10}}{9}, \ldots p_9 + \frac{p_{10}}{9}, 0\right) \equiv (q_1, q_2, \ldots, q_9, 0) \quad (A.8)$$

is generated. Then (A.8) is modified so that $$p_{elevated} = (q_1 - q_1 \cdot p_{target}, q_2 - q_2 \cdot p_{target}, \ldots, q_9 - q_9 \cdot p_{target}, p_{target}) \equiv (r_1, r_2, \ldots, r_9, r_{10}) \quad (A.9).$$

The transformation from (A.7) to (A.9) causes the identified population to be, on average, the 7th largest mixture component in half the samples, and the smallest mixture component in the other half.

Figure 21A:
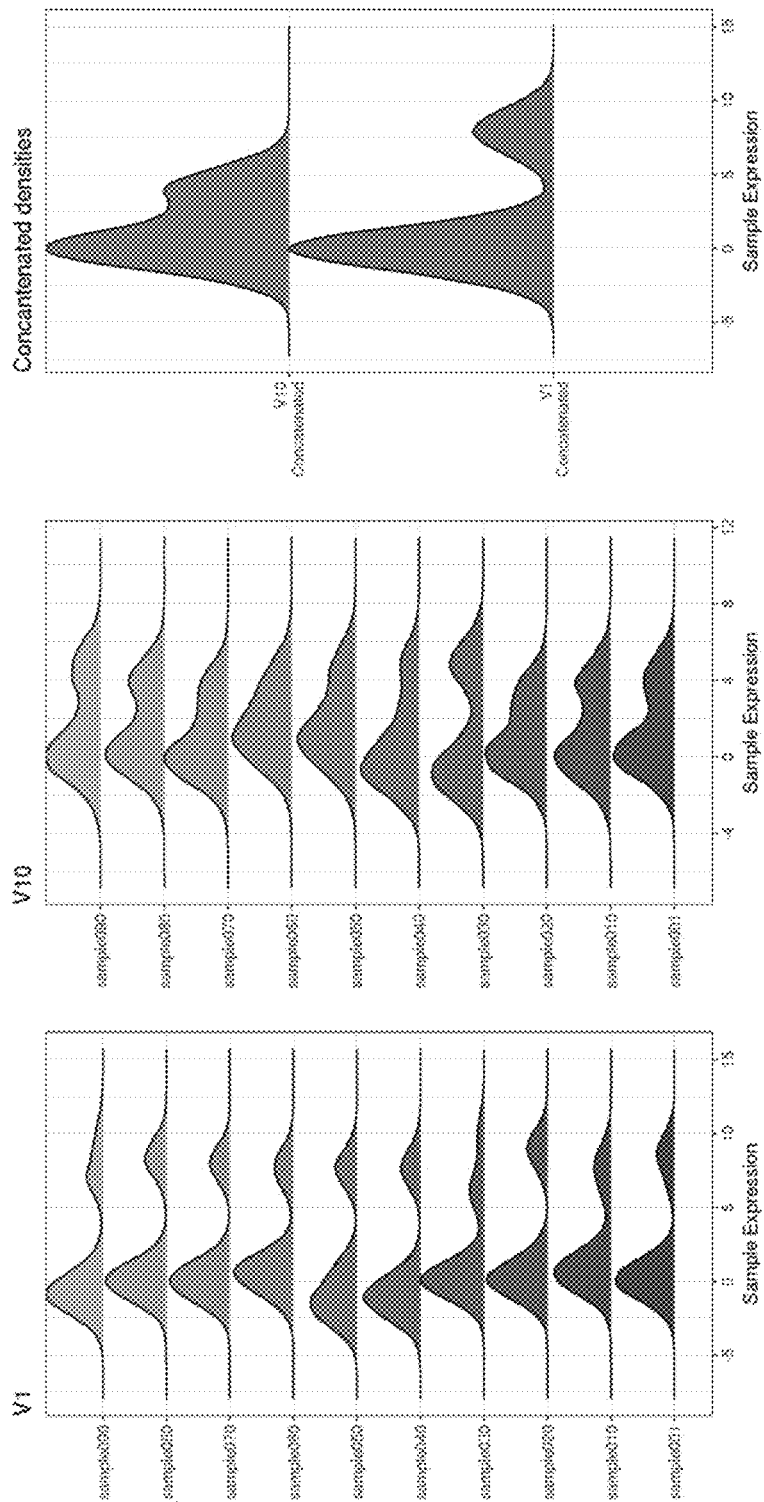
FIGS. 21A-21C provide visual summary of baseline simulation.
Figure 21C:
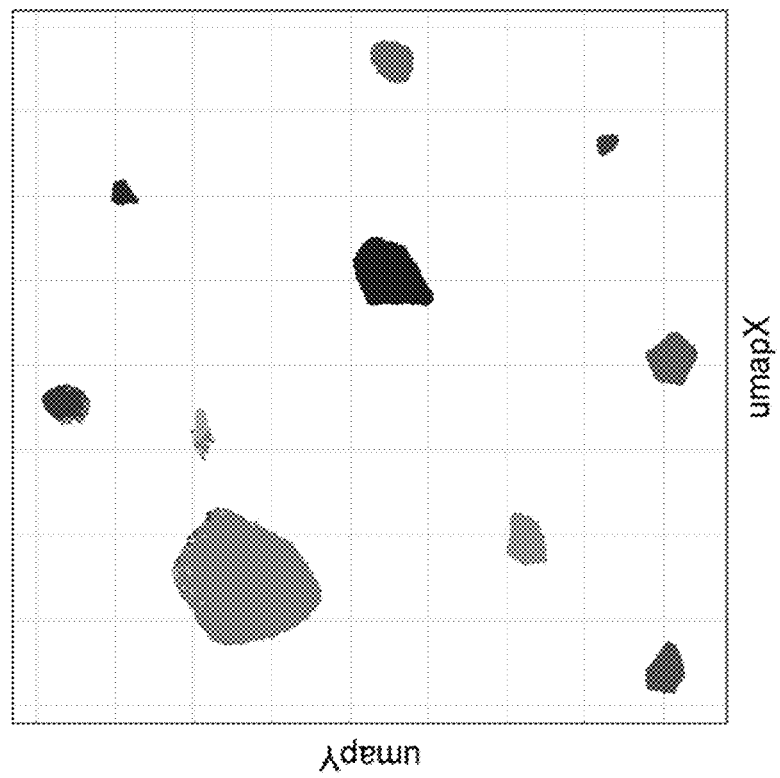
Figure 21B:
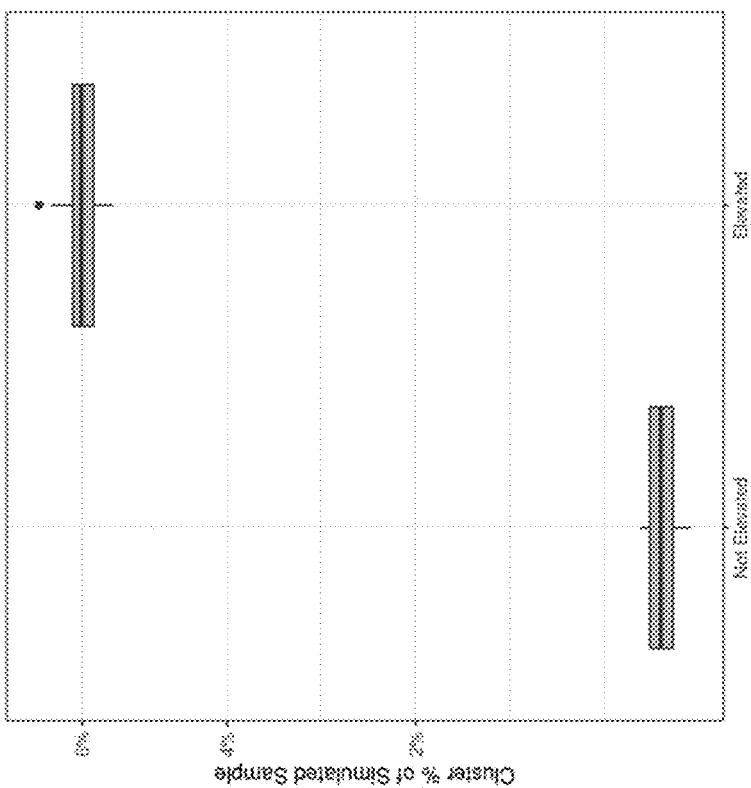

A sample of size $n_j$ with $1 \leq j \leq 100$ is generated by first determining the relative size of each mixture component within the sample. When the sample is selected as having the elevated population, the size of mixture components is determined by taking a sample from a multinomial distribution with $n_j$ trials and cell probabilities determined by (A.9). Otherwise, the size of mixture components is determined by taking a sample from a multinomial distribution with $n_j$ trials and cell probabilities determined by (A.7). In both cases, the resulting multinomial vector is then used to sample multivariate Gaussian samples of the corresponding size, with mean vectors $\mu_c + e_{c,j}$ and covariance matrices $\Sigma_c$, for $1 \leq c \leq 10$. The vector $e_{c,j} = (e_{c,j,1}, \ldots, e_{c,j,10})$ is determined by taking a 10 independent samples $\tilde{\epsilon}_{c,j,k} \sim N(0, \frac{1}{2})$, $1 \leq k \leq 10$, and then rounding $e_{c,j,k} = \text{round}(\tilde{\epsilon}_{c,j,k})$ to the nearest integer. The vector $e_{c,j}$ models sample-specific perturbations (corresponding to subject-level effects) without modifying (with high probability) the semantic interpretation of the annotations corresponding to $p_c$. A visualization of the baseline experiment is provided in FIGS. 21A-21C.

Once the experimental data is generated, it is processed by FAUST in a completely unsupervised setting. FAUST is set to use individual samples as the experimental unit. All simulated variables are taken as admissible and the channel boundaries are set to the entire real line for all markers. The depth score selection threshold is set to 0.01, the depth score selection quantile is set to the median, and the phenotype occurrence number is set to 25. The 100 samples are also concatenated and clustered by the flowSOM algorithm in two different ways. First, the flowSOM grid is set to 1 by the number of mixture components to simulate one best case scenario: an oracle provides flowSOM with the true number of clusters. Second, flowSOM over partitions the data by setting the grid to 5 by 5 (assuming 25 clusters when in truth there are 10).

To test how well each of the three methods discover sub-populations associated with differential abundance, a binary response is generated for each sample in the experiment. For samples where the identified population is elevated, a probability of response $p_{response}$ is varied from 0.50 to 0.80 in increments of 0.05. Each elevated sample is then associated with a response status by sampling from a Bernoulli ($p_{response}$). Similarly, samples where the identified population is not elevated are given a probability of response $q_{response} \equiv 1 - p_{response}$. Each non-elevated sample is then associated with a response status by sampling from a Bernoulli ($q_{response}$).

Once samples are associated with a binary outcome, the clusters produced by each of the three approaches are tested for differential abundance following the strategy described herein, including in section A equation (4.5). P-values are adjusted for FDR (q-values). In the event FAUST discovers the elevated population by exact annotation, the associate q-value is recorded. For flowSOM, the "best" q-value is defined as follows. Both the cluster containing the largest number of observations from the elevated population in terms of absolute counts, and the cluster containing proportionally the most observation from the elevated population are identified. The minimum q-value from the two clusters (when different) is recorded for both the oracle flowSOM and over partitioned flowSOM clusterings.

This modeling procedure is repeated 50 times for each setting of $p_{response}$. The median q-values across each of the 50 iterations is recorded in a single simulation iteration. After this, the entire experimental simulation is repeated 50 times, and the median of median q-values across those 50 simulation runs is reported. In addition, F-measures of the clusterings are computed, along with several other measures of the quality of the FAUST clusterings.

A.1.3 Simulation Tuning Parameters

The first simulation parameter that is variated is the underlying number of mixture components: this parameter is set to 25 components and 50 components, in addition to the baseline of 10. While the sample sizes are random, the underlying sampling scheme is fixed, which introduces rarer and rarer populations appear across simulations as the number of mixture components increase. In both the 25 and 50 component setting, the probability vector (A.7) is expanded accordingly; a continues to be set to 1 for each component. In all cases, sampling from the Dirichlet continues until all elements are greater or equal to 0.001. In the 25-component setting, the elevated population has $p_{target}$ set to $p_{18}$; in the 50 component setting, $p_{target}$ is set to $p_{35}$.

Figure 22A:
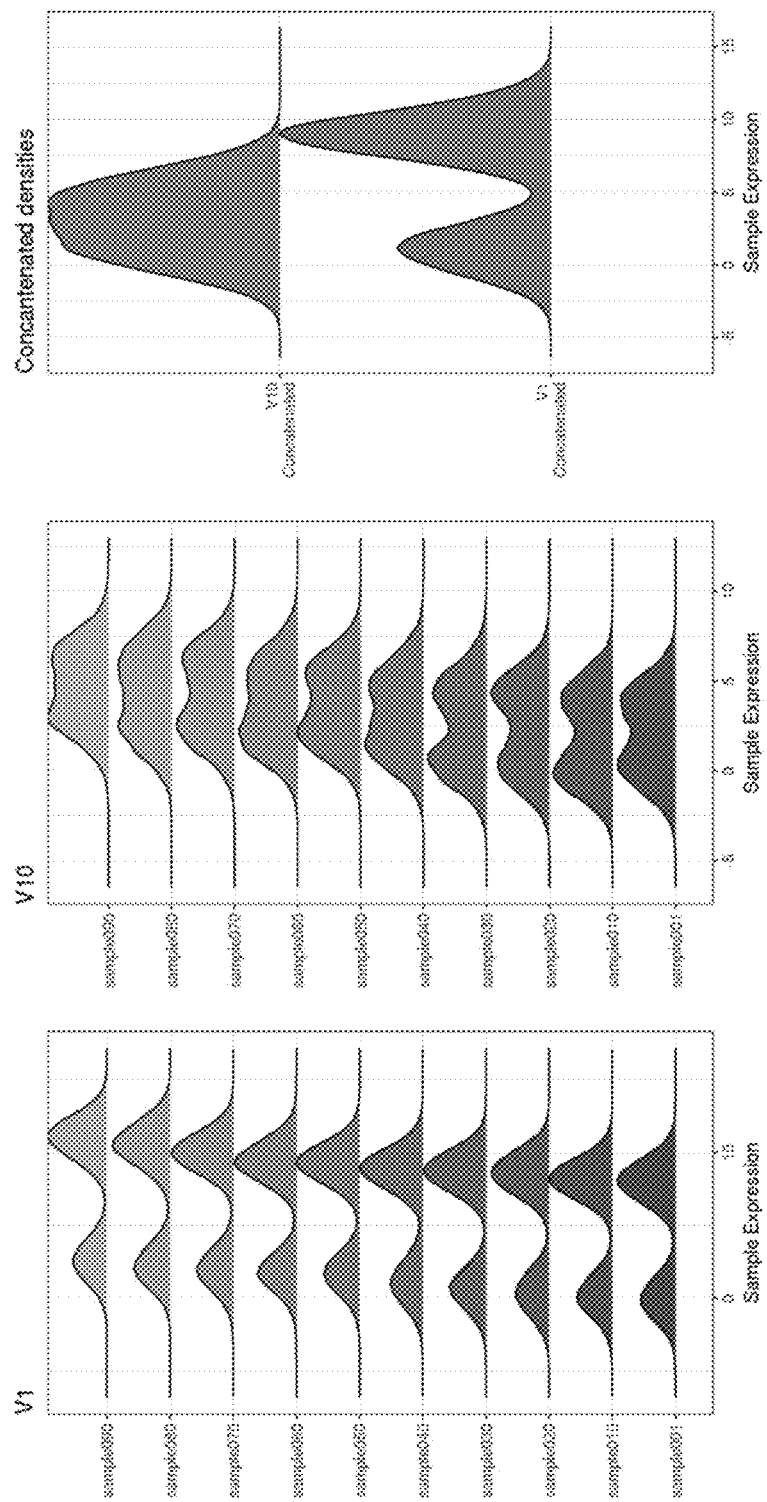
Figure 22B:
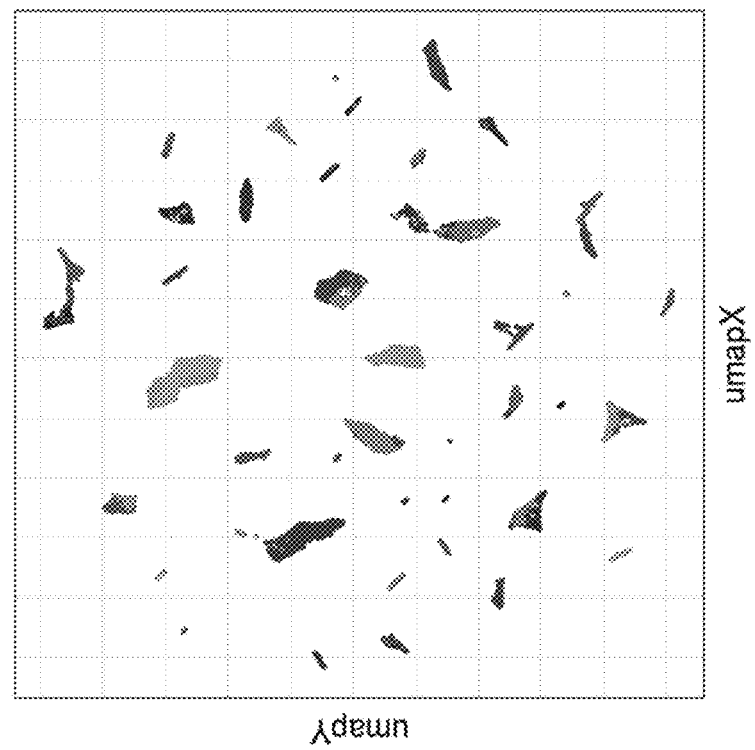
Figure 22C:
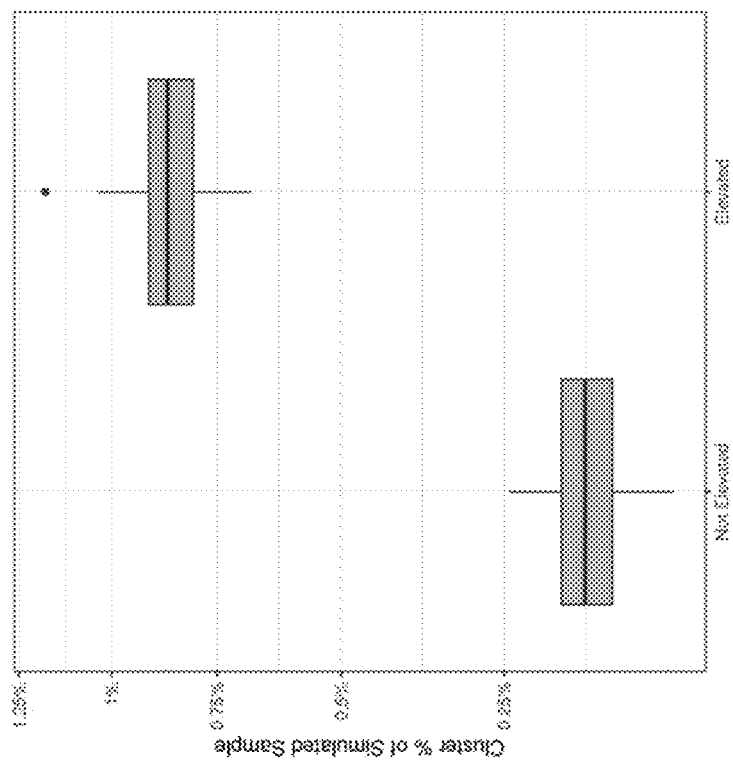

The second simulation parameter varied is used to add a batch effect to the simulation. The batch effect is modeled as a translation of the underlying mean vector. Batches are modeled as groups of 10 samples. After the initial 10 samples are generated, the mean vectors of the Gaussian mixture components (sampled from (S4)) are translated by a constant vector $\lambda_1=(1/3, 1/3, \ldots, 1/3)$. After the next 10 samples are generated, the translate increases to the constant vector $\lambda_2=(2/3, 2/3, \ldots, 2/3)$. This continues in groups of 10 until the final 10 samples are translated by $\lambda_9=(9/3, 9/3, \ldots, 9/3)$. FIGS. 22A-22C illustrate an example of a simulated experiment with 50 mixture components and the batch effect parameter turned on.

Figure 23A:
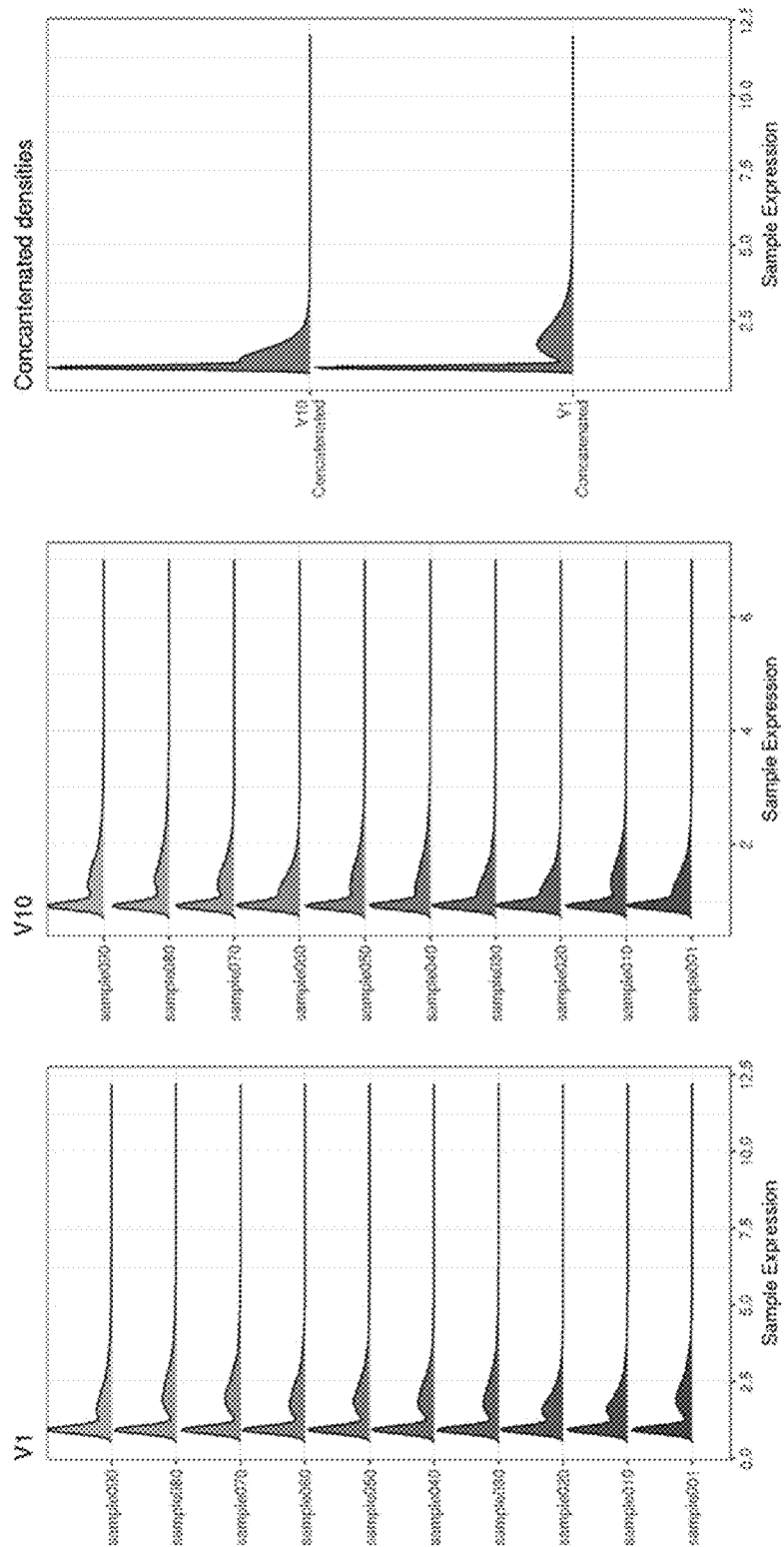
Figure 24:
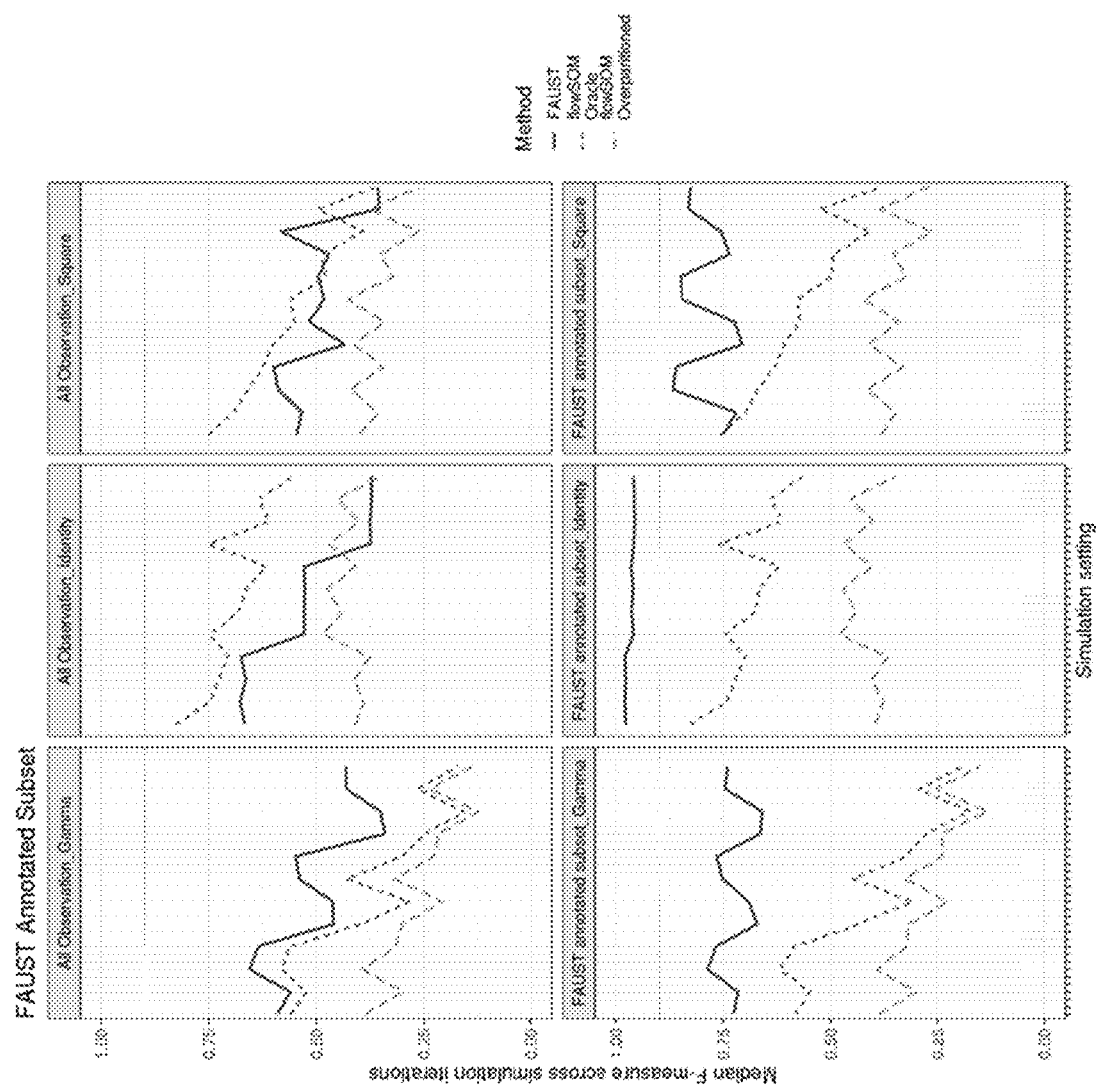
FIG. 24 provides the median F-measure across the 50 simulation iterations (with 3 exceptions). Results are stratified by transformation type: $h(x)=x$ (identity map); $f(x)=x2$ (square map); $g(x)=\Gamma(1+(x/4))$ (gamma map). F-measures are computed between each method's clustering and the entire simulated dataset (row 1). F-measures are also computed between each method and the subset of observations that FAUST annotates (row 2). The figures show FAUST improves markedly (in terms of F-measure) on the set of labeled observations it labels, while the F-measure of flowSOM with an oracle and flowSOM over partitioned perform similarly on the two sets. This figure provides a demonstration of the difficulty of comparing FAUST clusterings to computational methods in current use: classic measures of clustering performance, such as the F-measure, do not directly account for the biological information present in FAUST annotations. Similar trends were observed in other clustering metrics, such as the adjusted rand index. When the annotated subset is compared to associated subset of the ground truth, FAUST's performance improves markedly in terms of F-measure, while flowSOM shows no noticeable improvement on the subset. Similar difficulties emerge when attempting to benchmark FAUST on public datasets.

The third simulation parameter controls whether or not nuisance variables are added to the simulation. This parameter is meant to generate data under the scenario that several markers in the panel are uninformative because of staining issues. When this parameter is turned on the following occurs. Each time a sample of size $n_j$ is generate, an independent sample of size $n_j$ it taken from a Multivariate Gaussian distribution centered at $\mu_{nuisance}=(5, 5, 5, 5, 5)$, and $\Sigma_{nuisance}$ constrained to have variances between 1 and 2 but otherwise random. The independent Gaussian sample is then adjoined to the mixture of size $n_j$, producing a simulated data set in 15 dimensions. Since nuisance variables are independently generated, they do not affect the mixture structure of a given simulation. Consequently, the underlying annotations of observations by their cluster component mean vector are not changed when the nuisance variables are added to the simulation. The final simulation parameter is used to investigate departures from normality. Two settings are available: after generating each sample, the data are transformed coordinate-by-coordinate through the square map $f(x)=x^2$ or the gamma map $g(x)=\Gamma(1+(x/4))$. The square map was used to investigate a mild departure from Normality; the gamma map is used to transform the mixture into data that looked similar to CyTOF. Under the gamma map, the space possible Gaussian mean vectors are modified to those determined by Table 5. FIGS. 23A-23C illustrate an example of a simulated experiment with 25 mixture components, both the batch effect parameter and nuisance variable parameters turned on, and data are transformed by the Gamma map.

TABLE 5

Possible mean vector entries for the ten simulation variables when data subsequently transformed by the map $g(x) = \Gamma(1 + |(|x/4))$.

|  | V1 | V2 | V3 | V4 | V5 | V6 | V7 | V8 | V9 | V10 |
|---|---|---|---|---|---|---|---|---|---|---|
| No Signal | 0 | 0 | 0 | 0 | 0 | 0 | 0 | 0 | 0 | 0 |
| Signal | 8 | 8 | 8 | 7 | 7 | 7 | 7 | 6 | 6 | 6 |

A.1.1 Simulation Results

By adjusting the tuning parameters described in section A.14.3, 36 distinct scenarios are explored in silico. Each simulation setting is run 50 times, with three exceptions which are now reported. The scenario of 25 Clusters with no batch effect but with nuisance variables transformed by the gamma map completed 34 iterations. The scenario of 25 Clusters with batch effect but with no nuisance variables transformed by the gamma map completed 37 iterations. The scenario of 50 Clusters with batch effect and with nuisance untransformed (the identity map) completed 35 iterations. Based on their log files, these three scenarios did not complete 50 iterations in 7 days of compute time due to generating experiments in which the regression modeling took unusually long to fit to each cluster.

This simulation study shows that departures from multivariate-normality as well as batch-effects combined with large numbers of clusters impair FlowSOM's ability to define clusters that correlate with outcome. FAUST, on the other hand, performed robustly across simulation settings since its key methodological assumption is that some subset of the measured markers in a cytometry data set are marginally separated into modal groups. Plots of the observed expression data show the MCC anti-PD1 data set has non-Gaussian characteristics, and also has sample-to-sample variation which is common in most cytometry experiments (FIGS. 9A-9D). Hence, the non-Gaussian nature of the MCC anti-PD1 trial data combined with sample-to-sample variation both contribute to the discovery differences observed between FlowSOM and FAUST.

A.1.2 Additional Simulation Results

Additional simulation studies were conducted to compare the FAUST methodology to existing computational approaches. Disclosed herein are the results of two studies. In both, multivariate gaussian data was again simulated in a fashion analogous to that described in section "A.1.2 Baseline simulation description". Each simulation iteration, 50 samples were simulated independently, with each sample containing 75 clusters specified by the mean vector listed in Table 6, after transformation by the map $g(x)=\Gamma(1+|(|x/4))$.

In the first study, a fixed probability vector was sampled from the Dirichlet distribution with 75 components. Across simulation iterations, the mass of the 70th component was then incremented prior to generating 25 of the simulated samples. Samples that had the 70th mixture component elevated were called responders; samples with the 70th component unmodified were called non-responders. Different computational discovery methods were then applied to the samples. If a method produced a clustering of the simulated dataset, the resulting clusters were tested for association with responder status using a binomial GLMM. The frequency of the best-associated cluster was then used in logistic regression model to predict responder status and 5-fold cross-validated AUC were computed. For methods that did not produce a ranked clustering of the dataset, a derived best cluster was computed by combining all simulated observations in subsets deemed relevant by the method into a single derived cluster, which was then used in a logistic regression model to predict responder status.

Figure 31:
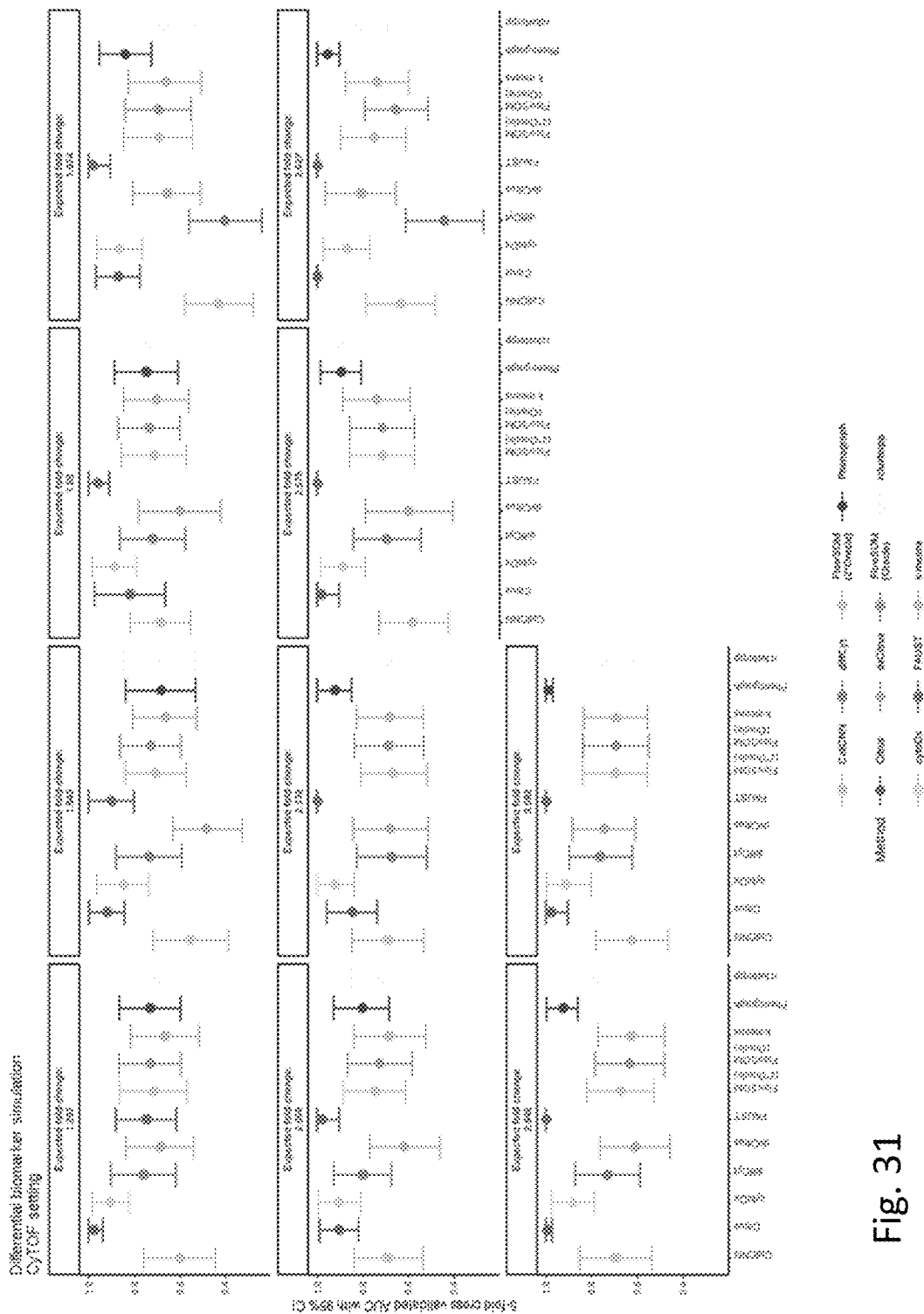
FIG. 31 shows five-fold cross-validated AUCs for computational methods applied to simulated datasets. Each simulation iteration, 50 samples were simulated independently, with each sample containing 75 clusters sampled from multivariate-Gaussian distributions with the mean vectors specified in table 5 and random covariance structure and then transformed by the map $g(x)=\Gamma(1+(|x/4|))$. A fixed probability vector was sampled from the Dirichlet distribution with 75 components. Across simulation iterations, the mass of the $70^{th}$ component was then incremented prior to generating 25 of the simulated samples. Samples that had the $70^{th}$ mixture component elevated were called responders; samples with the $70^{th}$ component unmodified were called non-responders. The reported computational discovery methods were then applied to the samples. If a method produced a clustering of the simulated dataset, the resulting clusters were tested for association with responder status using a binomial GLMM. The frequency of the best-associated cluster was then used in logistic regression model to predict responder status and 5-fold cross-validated AUC were computed. For methods that did not produce a ranked clustering of the dataset, a derived best cluster was computed by combining all simulated observations in subsets deemed relevant by the method into a single derived cluster, which was then used in a logistic regression model to predict responder status. All methods were run with default parameter settings where possible. The methods CITRUS, FlowSOM, k-means, and rclusterpp were provided information about the number of clusters in the experiment. The reported cross-validated AUC for the cytoDx method is based on fitting a predictive model to all 50 simulated samples, and then predicting responder status for those same samples based on the simulated datasets alone. The CITRUS method was also run without providing information about the number of clusters in the experiment—results are reported as dsCitrus (stating for default settings).

FIG. 31 contains the result of this study and demonstrates that the FAUST methodology is able to detect and use the simulated biomarker to correctly predict responder status when the simulated expected fold change of the biomarker in responders exceeds 1.5. All methods were run with default parameter settings where possible. The methods CITRUS, FlowSOM, k-means, and rclusterpp were provided information about the number of clusters in the experiment. The reported cross-validated AUC for the cytoDx method is based on fitting a predictive model to all 50 simulated samples, and then predicting responder status for those same samples based on the simulated datasets alone. The CITRUS method was also run without providing information about the number of clusters in the experiment—results are reported as dsCitrus (stating for default settings).

In the second study, datasets were again generated according to the scheme just described. However, the prevalence of responders in the population was set (in expectation) to 50%, but the strength of the association between samples with the elevated biomarker and responder status was varied. The goal of this study was to investigate the performance of methods when a relevant biomarker did not perfectly predict responder status, a situation which might arise in observed datasets should different pathways exist that produce a positive response to a therapy.

Consequently, for each simulated dataset, responder status was sampled 10 times for each tested strength of association. Clusters produced by each method were then tested for association with the simulated response status, and the best associated cluster was used to predict responder status in a logistic regression model. Model coefficients were recorded for 5 simulated datasets, and ultimately used to compute boot-strapped estimates of the log-odds of the association between the observed frequencies in the best cluster and responder status.

Figure 32:
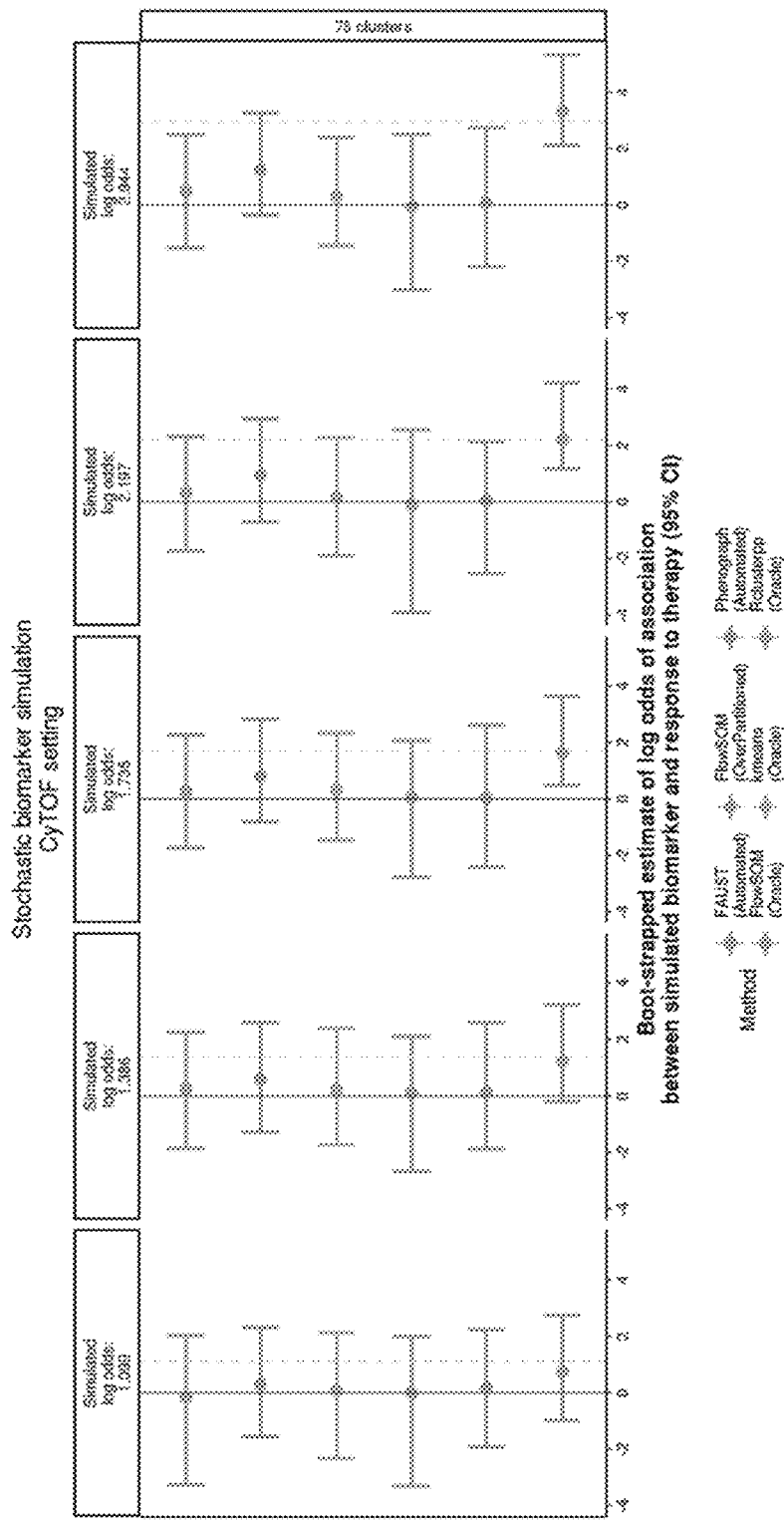
FIG. 32 shows estimates of effect size in simulation study Simulated datasets were generated according to a similar scheme as that used in FIG. 31. However, the prevalence of responders in the population was set (in expectation) to 50%, while the strength of the association between samples with the elevated biomarker and responder status was varied. For each simulated dataset, responder status was sampled 10 times for each tested strength of association. Clusters produced by each method were then tested for association with the simulated response status, and the best associated cluster was used to predict responder status in a logistic regression model. Model coefficients were recorded for 5 simulated datasets, and ultimately used to compute boot-strapped estimates of the log-odds of the association between the observed frequencies in the best cluster and responder status.

FIG. 32 contains the result of this study and demonstrates that, for log-odds larger than 1.7, FAUST is able to detect a statistically significant effect. In all examined simulation settings, no other method tested in this study was able to detect statistically significant associations between the simulated responder status and simulated biomarker, as their 95% boot-strapped confidence interval all include 0.

TABLE 6

Possible mean vector entries for the ten simulation variables.

|  | V1 | V2 | V3 | V4 | V5 | V6 | V7 | V8 | V9 | V10 |
|---|---|---|---|---|---|---|---|---|---|---|
| No Signal | 0 | 0 | 0 | 0 | 0 | 0 | 0 | 0 | 0 | 0 |
| Signal | 8 | 8 | 8 | 8 | 8 | 8 | 8 | 8 | 8 | 8 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for identifying a specific cell population comprising:
   a) providing single-cell flow or mass cytometry biomarker expression data from two or more cell samples, wherein the biomarkers are associated with a cell phenotype;
   b) growing an exhaustive annotation forest of partition trees of the biomarker expression data for each cell sample, the partition trees comprising 1-dimensional, depth-3 gating strategies, constrained by shape;
   c) estimating annotation boundaries for one or more biomarkers within each cell sample by averaging over gates drawn for each biomarker over the entire annotation forest;
   d) calculating a depth score for each biomarker to quantify how well-gated each biomarker is in each cell sample;
   e) selecting biomarkers having a high distribution of depth score across cell samples;
   f) standardizing a number of annotation boundaries for each selected biomarker and their associated cell phenotype;
   g) relaxing the depth-3 constrained shape for each cell sample;
   h) searching the 1-dimensional, relaxed depth-3 gating strategies to discover and select phenotypes present in each cell sample;
   i) assigning a phenotypic score to each selected phenotype that quantifies cell homogeneity in each cell sample with that phenotype;
   j) selecting one or more high-scoring phenotypes for annotation; and
   k) producing an annotated count matrix that displays the numbers of cells from each cell sample for each selected high-scoring phenotype.

2. The method of claim 1, wherein the cell sample is a patient sample.

3. The method of claim 2, wherein the patient sample is a blood sample.

4. The method of claim 1, wherein the method is used to identify biomarkers associated with a particular condition or disease.

5. The method of claim 1, wherein the method is used to diagnosis a subject with a particular condition or disease.

6. The method of claim 1, wherein the method is used to monitor the effectiveness of a particular treatment and/or monitor a subject's disease progression associated with a particular condition or disease.

7. The method of claim 1, wherein the method is used to predict a subject's response to treatment for a particular condition or disease.

8. The method of claim 4, wherein the particular condition or disease is Merkel cell carcinoma.

9. The method of claim 8, wherein Merkel cell carcinoma is of viral origin.

* * * * *